(12) United States Patent
Nishiguchi et al.

(10) Patent No.: US 9,505,844 B2
(45) Date of Patent: Nov. 29, 2016

(54) ANTI-HUMAN CCR7 ANTIBODY, HYBRIDOMA, NUCLEIC ACID, VECTOR, CELL, PHARMACEUTICAL COMPOSITION, AND ANTIBODY-IMMOBILIZED CARRIER

(71) Applicants: Sekisui Chemical Co., Ltd., Osaka (JP); NB HEALTH LABORATORY CO., LTD., Hokkaido (JP)

(72) Inventors: Naoki Nishiguchi, Ibaraki (JP); Akiyoshi Hirayama, Ibaraki (JP); Masahiro Furutani, Ibaraki (JP); Tatsuo Shimizu, Osaka (JP); Kiyoshi Takayama, Hokkaido (JP); Tomoko Shimizu, Hokkaido (JP); Kazuya Suzuki, Tokyo (JP)

(73) Assignees: SEKISUI CHEMICAL CO., LTD., Osaka (JP); NB HEALTH LABORATORY CO., LTD., Hokkaido (JP)

( * ) Notice: Subject to any disclaimer, the term of this patent is extended or adjusted under 35 U.S.C. 154(b) by 0 days.

(21) Appl. No.: 14/489,898

(22) Filed: Sep. 18, 2014

(65) Prior Publication Data

US 2015/0010998 A1  Jan. 8, 2015

Related U.S. Application Data

(62) Division of application No. 13/876,265, filed as application No. PCT/JP2011/072014 on Sep. 27, 2011, now Pat. No. 8,865,170.

(30) Foreign Application Priority Data

Sep. 28, 2010 (JP) ................................. 2010-217096

(51) Int. Cl.
  C07K 16/28 (2006.01)
  A61K 31/713 (2006.01)
  A61K 39/00 (2006.01)

(52) U.S. Cl.
  CPC ......... *C07K 16/2866* (2013.01); *A61K 31/713* (2013.01); *A61K 2039/505* (2013.01); *C07K 2317/70* (2013.01); *C07K 2317/76* (2013.01)

(58) Field of Classification Search
  None
  See application file for complete search history.

(56) References Cited

U.S. PATENT DOCUMENTS

| | | |
|---|---|---|
| 3,773,919 A | 11/1973 | Boswell et al. |
| 4,945,050 A | 7/1990 | Sanford et al. |
| 8,066,996 B2 | 11/2011 | Calleja et al. |
| 2002/0168358 A1 | 11/2002 | Gladue et al. |
| 2009/0041761 A1 | 2/2009 | Chiba et al. |
| 2010/0092457 A1 | 4/2010 | Aburatani et al. |
| 2010/0111852 A1 | 5/2010 | Yoshida |

FOREIGN PATENT DOCUMENTS

| | | |
|---|---|---|
| EP | 0 058 481 | 8/1982 |
| JP | 2003-28858 | 1/2003 |
| WO | 93/11161 | 6/1993 |
| WO | 93/17706 | 9/1993 |
| WO | 96/22373 | 7/1996 |
| WO | 2004/104574 | 12/2004 |
| WO | 2006/041157 | 4/2006 |
| WO | 2007/003426 | 1/2007 |
| WO | 2007/075592 | 7/2007 |
| WO | 2007/146172 | 12/2007 |
| WO | 2008/020586 | 2/2008 |
| WO | 2008/072723 | 6/2008 |

OTHER PUBLICATIONS

Vajdos et al. (J Mol Biol. Jul. 5, 2002;320(2):415-28 at 416).*
Brown et al. (J Immunol. May 1996;156(9):3285-91).*
International Preliminary Report on Patentability and Written Opinion issued Apr. 16, 2013 in International (PCT) Application No. PCT/JP2011/072014.
International Search Report issued Dec. 13, 2011 in International (PCT) Application No. PCT/JP2011/072014.
Japanese Office Action issued Jan. 4, 2013 in corresponding Japanese Patent Application No. 2012-536465, with English translation.
M. Alfonso-Pérez et al., "Anti-CCR7 monoclonal antibodies as a novel tool for the treatment of chronic lymphocyte leukemia", Journal of Leukocyte Biology, vol. 79, Jun. 2006, pp. 1157-1165.
J. Campbell et al., "CCR7 Expression and Memory T Cell Diversity in Humans", The Journal of Immunology, pp. 877-884, 2001.
M. Birkenbach et al., "Epstein-Barr Virus-Induced Genes: First Lymphocyte-Specific G Protein-Coupled Peptide Receptors", Journal of Virology, vol. 67, No. 4, pp. 2209-2220, Apr. 1993.

(Continued)

*Primary Examiner* — Brian J Gangle
*Assistant Examiner* — Andrea McCollum
(74) *Attorney, Agent, or Firm* — Wenderoth, Lind & Ponack, L.L.P.

(57) ABSTRACT

An anti-human-CC-motif-receptor-7 (anti-human-CCR7) antibody which is useful as a therapeutic agent for tissue fibrosis or cancer, and a pharmaceutical composition containing the anti-human CCR7 antibody, and the like is described. An anti-human CCR7 antibody specifically binding to an extracellular domain of human CCR7, having a heavy chain CDR3 containing an amino acid sequence represented by SEQ ID NO: 7, SEQ ID NO: 17, SEQ ID NO: 27, SEQ ID NO: 37, SEQ ID NO: 47, SEQ ID NO: 57, SEQ ID NO: 67, or SEQ ID NO: 77 is provided. Also provided is an anti-human CCR7 antibody having heavy chain CDRs 1-3 and light chain CDRs 1-3 containing amino acid sequences represented by SEQ ID NOs: 5-10, 15-20, 25-30, 35-40, 45-50, 55-60, 65-70, or 75-80. The anti-human CCR7 antibody of the present invention may be used as an active ingredient of a therapeutic agent for tissue fibrosis or cancer.

14 Claims, 16 Drawing Sheets

(56) References Cited

OTHER PUBLICATIONS

V. Schweickart et al., "Cloning of Human and Mouse EBI1, a Lymphoid-Specific G-Protein-Coupled Receptor Encoded on Human Chromosome 17q12-q21.2", Genomics, vol. 23, 643-650, 1994.
A. Viola et al., "Chemokines and Their Receptors: Drug Targets in Immunity and Inflammation", Annu. Rev. Pharmacol. Toxicol., vol. 48, pp. 171-197, 2008.
D. Pilling et al., "Identification of Markers that Distinguish Monocyte-Derived Fibrocytes from Monocytes, Macrophages, and Fibroblasts", PLoS ONE, vol. 4, Issue 10, e7475, pp. 1-18, Oct. 2009.
T. Wada et al., "Fibrocytes: a new insight into kidney fibrosis", Kidney International, vol. 72, International Society of Nephrology, pp. 269-273, 2007.
Abe et al., "Peripheral Blood Fibrocytes: Differentiation Pathway and Migration to Wound Sites", The Journal of Immunology, vol. 166, pp. 7556-7562, 2001.
S. Curnow et al., "Distinct Types of Fibrocyte Can Differentiate from Mononuclear Cells in the Presence and Absence of Serum", PLoS ONE, vol. 5, Issue 3, e9730, pp. 1-10, Mar. 2010.
Bowie et al., Science, vol. 247, pp. 1306-1310, 1990.
Burgess et al., J. Cell Biol. vol. 111, pp. 2129-2138, 1990.
Lazar et al., Mol. Cell. Biol., vol. 8, pp. 1247-1252, 1988.
Bork, Genome Research, vol. 10, pp. 398-400, 2000.
Supplemental European Search Report issued Apr. 15, 2014 in corresponding European Application No. 11 82 9086.
Pierce et al., "Therapeutic Targeting of CC Ligand 21 or CC Chemokine Receptor 7 Abrogates Pulmonary Fibrosis Induced by the Adoptive Transfer of Human Pulmonary Fibroblasts to Immunodeficient Mice", The American Journal of Pathology, 2007, vol. 170, No. 4, pp. 1152-1164.

\* cited by examiner

FIG. 1

(a) VH of R7-01 (SEQ ID NO: 2)

CDR1                        CDR2
EVQLQQSGPELVKPGTSVKMSCKGSGYTFTDYYINWVRQSHGKSLEWIGRVNPGNGGTSYNQRFKGKATLTVDKFLSTAFMQ

CDR3
LNSLTSEDSAVYFCARTGTYYNYDRGGFAYWGHGTLVTVSAAKTTPPS (b) VL of R7-01 (SEQ ID NO: 4)

CDR1                       CDR2
DVLLTQSPVSLPVSLGDQASISCRCSQNIVHINGNTYLEWFLQKPGQSPKLLIYKVSNRFSGVPDRFSGSGSGTDFTLKIRR

CDR3
VEAEDLGVYYCFQGSHVPHTFGSGTK

FIG. 2

(a) VH of R7-02 (SEQ ID NO: 12)

CDR1        CDR2
LHACRSTLEDLLVIWIQVQLQQSGAELERPGASVKLSCTASGFNIRDDYVHWVKQRPEQGLEWIGRIDPANGNTKYGPKFQA

CDR3
KATLTADTSSNTAYLQLGSLTSEDTAVYYCTRSFYDYDLFVPWGQGTLVTVSAAKTTPP (b) VL of R7-02 (SEQ ID NO: 14)

CDR1        CDR2
DAVVTQESALTTSPGETVTLTCRSSTGAVTKNNFANWVQEKPDHLFTGLIGGNNIRAPGVPARFSGSLIGDKAALSITGAQTE

CDR3
DEAIYFCALWYSNHWVFGGGTK

FIG. 3

(a) VH of R7-05 (SEQ ID NO: 22)

CDR1                     CDR2
IWIEVQLQQSGAELVRPGASVKLSCTASGFNIKDDYIHWVKQRPEQGLDWIGRVDPADGNTKYAPNFHDKATVTADTSSNTA

CDR3
YLQLSSLTSEDTAVYYCARSFYDYDLFASWGQGTLVTVSAAKTTPP (b) VL of R7-05 (SEQ ID NO: 24)

CDR1                 CDR2
DAVVTQESALTTSPGETVTLTCRSSTGAVTTSNFANWVQEKPDHLFTGLISSNNKRAPGVPARFSGSLIGDKAALSITGAQT

CDR3
EDEAIYFCALWYSNHWVFGGGTK

FIG. 4

(a) VH of R7-09 (SEQ ID NO: 32)

```
                          CDR1                    CDR2
IEVQLQQSGTELVRPGASVKLSCTASGFNIKDDYIHWVKQRPDQGLEWIGRIDPANGNTKYAPKFQDKATITSDTSSNTAYL

CDR3
QLSSLTSEDTAVYYCARSFYDYDLFASWGQGTLVSVSAAKTTPP
```

(b) VL of R7-09 (SEQ ID NO: 34)

```
                         CDR1                  CDR2
DAVVTQESALTTSPGGTVILTCRSSTGAVTTSNFANWVQEKPDHLFSGLISGNNKRAPGVPARFSGSLIGDKAALSITGAQT

CDR3
EDEAMYFCALWYNNHWVFGGGTK
```

FIG. 5

(a) VH of R7-11 (SEQ ID NO: 42)

CDR1                     CDR2
WIEVQLQQSGPDLVMPGASVRISCKASGYSFTAYYMHWVKQSHGLSLEWIGRVNPNNGGTSYNRKFKDKAILTVDRSSSTAF

CDR3
MELRSLTSEDSAVYYCARSESDHFYAMDSWGQGNSVSVSSAKTT (b) VL of R7-11 (SEQ ID NO: 44)

CDR1                  CDR2
DIVMTQTPLSLPVSLGDQVFISCRSSQSLVHSNGNTYLCWFLQKPGQSPKLLIYRVSNRFSGVPDRFSGSGSGTDFTLKISR

CDR3
VEAEDLGVYFCFQGSHVPHTFGSGTK

FIG. 6

(a) VH of R7-18 (SEQ ID NO: 52)

```
                                      CDR1                    CDR2
IWIEVQLQQSGPDLVKPGASVKISCKASGYSFTGYYMHWVKQSHGKSLEWIGRVNPNNGGTSYNKKFKVKAILTVDRSSSTA

CDR3
YMEFRSLTLEDSAVYYCARSESNNFYAMDYWGQGKSVTVSSAKTTPP
```

(b) VL of R7-18 (SEQ ID NO: 54)

```
                                    CDR1                   CDR2
DILMTQTPLSLPVSLGDQVSISCRSSQSLVHSNGNTYLCWYLQKPGQSPKLLIYRVSNRFSGVPDRFSGSGSGTDFTLKISR

CDR3
VEAEDLGVYFCFQGSHVPHTFGSGTK
```

FIG. 7

(a) VH of R7-25 (SEQ ID NO: 62)

```
                              CDR1                    CDR2
IWIEVMVVESGPGLMKPSQSLSLTCAVTGYSITSGYDWHWIRHFPGNILEWMGYINYSGSTNYKPSLKSRISITLDTSKNHF

CDR3
FLKLSSVTTEDTATYYCARGSYYSYEFAYWGQGTLVTVSAAKTTPPS
```

(b) VL of R7-25 (SEQ ID NO: 64)

```
                              CDR1                    CDR2
DIVMSQSPSSLAVSVGEKVTMSCKSSQRLLYYSTQKNYLAWYQQKPGQSPKLLIFWASTRESGVPNRFTGSGSGTDFTLTIN

CDR3
SVKAEDLAVYYCQQYYTYPTFGGGTK
```

FIG. 8

(a) VH of R7-47 (SEQ ID NO: 72)

CDR1                        CDR2
EVQLQQSGPDLVKPGTSVKISCKASGYKFTDFNMDWVRQRHGKSLEWIGDVNPQNGEIFYNQKFRGKATLTVVKSSSTTYLE

CDR3
LRSLTSEDTAVYFCTRLEFDYTGSNGFAYWGQGTLVTVSAAKTTPPS (b) VL of R7-47 (SEQ ID NO: 74)

CDR1                        CDR2
DILMTQTPLSLPVSLGDQASISCRSSQTLVHRNGNTYLEWYLQKPGQSPKLLIYKVSNRFSGVPDRFSGRGSGTDFTLKISR

CDR3
VEAEDQGIYYCFQGSHDPWTFGGGTK

ANTI-HUMAN CCR7 ANTIBODY, HYBRIDOMA, NUCLEIC ACID, VECTOR, CELL, PHARMACEUTICAL COMPOSITION, AND ANTIBODY-IMMOBILIZED CARRIER

TECHNICAL FIELD

The present invention relates to an anti-human CCR7 antibody, a hybridoma, a nucleic acid, a vector, a cell, a pharmaceutical composition, and an antibody-immobilized carrier, and more specifically, to an anti-human CCR7 antibody specifically binding to an extracellular domain of human CCR7, a hybridoma producing the antibody, a nucleic acid encoding a heavy chain variable region or a light chain variable region of the antibody, a vector having the nucleic acid, a cell having the vector, a pharmaceutical composition containing the antibody, and an antibody-immobilized carrier to which the antibody is immobilized.

BACKGROUND ART

A chemokine is a cytokine that modulates migration and cell function of various cells. Functional abnormality of a chemokine and its receptor causes various diseases such as autoimmune disease, acute and chronic inflammation, and cancer. Up to now, drugs that control the activities of a chemokine and its receptor have been developed and clinically applied, but it is hard to say that the problems are satisfactorily solved.

In order that a specific chemokine elicits its activity such as modulation of cell migration or cell function, it is necessary that the chemokine binds to a chemokine-selective cell membrane receptor. About 20 kinds of chemokine receptors have been found, and any of these chemokine receptors is a seven transmembrane type protein (GPCR) that binds to a trimeric G protein. When a chemokine binds to a receptor, it induces dissociation of the Gα unit of a trimeric G protein. As a result, it causes a increase in intracellular Ca concentration, or activates phosphatidylinositol 3-kinase (PI3K), or the small Rho GTPases pathway, or other pathways to lead expression of function. Chemokine receptors are activated by a relatively selective chemokine, but they share very similar primary structures of protein and intracellular activation mechanisms. Therefore, it is not easy to selectively interfere with the function of a specific chemokine receptor. Eliciting of function of respective chemokine and chemokine receptor in physiological and pathological conditions is controlled by each protein expressed during a specific period of time (during inflammation) in a specific cell or tissue (Non-Patent Document 1).

Human CC motif receptor 7 (CC MOTIF, RECEPTOR 7; also called: EBI1, CMKBR7; hereinafter referred to as "CCR7") is originally found as a GPCR that is expressed in a lymphocyte-selective manner by EPSTEIN-BARR virus infection (Non-Patent Document 2). Afterwards, CCR7 was proved to be a selective chemokine receptor for CCL19 (also called ELC) and CCL21 (also called SLC, EXODUS 2). Under physiological conditions, CCR7 is expressed in cells such as CD4-positive T cells (Th1, Th2, Treg cells), mature dendritic cells, and B cells relatively selectively. It is known that such cells are led to a lesion such as an inflamed site via CCR7 to increase the inflammatory reaction and the immunization reaction. Abnormal activation of CCR7 causes various diseases such as autoimmune disease, fibrosis following acute and chronic inflammation, and cancer metastasis.

The amino acid sequence of human CCR7 and the nucleotide sequence of human CCR7 gene have been already known (for example, GenBank: EAW60669.1).

Inflammation is a defense reaction against injury to tissue and infection. Following an increase in expression of inflammatory molecules (chemokines and cytokines) in response to various inflammatory stimulations, invasion of neutrophil and monocyte is promoted. As the inflammatory reaction further increases, T and B lymphocytes flow in and the pathosis becomes chronic. On the other hand, in a resolution stage of inflammation, apoptosis of excess leukocytes and phagocytosis by tissue macrophages occur, and repair of the injured tissue by interstitial cells (e.g., fibroblast) is observed.

Excessive proliferation and differentiation of interstitial cells are deeply related with exacerbation of various fibrosis (hepatic fibrosis, renal fibrosis, pulmonary fibrosis, skin fibrosis, cardiovascular fibrosis, gastrointestinal fibrosis, and other fibrous diseases). Chronic pulmonary fibrosis is caused by formation of scars throughout the lungs, and is a poor-prognosis disease. Pirfenidone, corticosteroids (for example, prednisone) having an antifibrotic activity and/or other drugs that suppress the immune system in the body are prescribed for suppressing the process leading to fibrosis. However, at present, it is hard to say that a satisfactory therapeutic outcome is achieved.

On the other hand, in recent years, the molecular mechanism of fibrosis in the repair process after inflammatory reaction is being clarified. In such a repair mechanism, local resting fibroblasts migrate to the injured region and generate an extracellular matrix protein to promote contraction of the injury and fibrogenesis (scar). Also it has been suggested that circulating fibroblast precursor cells and fibroblasts (they are present in blood) migrate to the site of injury or fibrogenesis, where they differentiate to mediate repair of tissues or other fibrous reactions.

Fibroblast precursor cells in blood differentiate from a CD14+ peripheral blood mononuclear cell group invading the inflamed site, into stromal cell-like cells (collagen type I and type III and fibronectin) locally (Non-Patent Document 3). These cells secrete an inflammatory cytokines, and also secrete an extracellular matrix proteins and other cytokines which may lead fibrogenesis. Although it is expected that fibrosis can be minimized if excess invasion of the fibroblast precursor cells in blood into the inflamed site can be selectively suppressed, such a measure has not reached clinical application.

Recently, the aforementioned CCR7 has attracted attention as a chemokine receptor that is expressed in a fibroblast precursor cell (Patent Document 1). It has been demonstrated that fibrosis is not developed even when such stimulation that leads development of pulmonary fibrosis or renal fibrosis is added to a CCR7-deficient transgenic animal (Non-Patent Document 4). Accordingly, it is expected that various fibrosis can be suppressed if the function of CCR7 can be inhibited by a low molecular-weight compound, monoclonal antibody, RNAi or the like. However, since chemokine receptors share very similar primary structures of protein and intracellular activation mechanisms, a substance capable of inhibiting CCR7 more selectively is desired. Although substances (monoclonal antibody or RNAi) that inhibit the function of CCR7 have been studied, there is still no case that has reached clinical application.

On the other hand, in a cancer therapy, it is important to suppress proliferation of primary cancer and to prevent recurrence accompanying distant metastasis. In addition to conventional surgical therapies and chemical therapies, molecular target drugs (for example, kinase inhibitor) and antibody pharmaceutical therapies have improved therapeutic outcomes. However, recurrent cancer accompanied by distant metastasis is poor in prognosis, so that development of a novel therapeutic drug is desired. As a mechanism of distal metastasis, the primary cancer travels blood vessels or travels lymphoid tissues. Although an extracellular matrix protease inhibitor (MMP inhibitor) has been developed as a metastasis preventive drug, there is still no case that has reached clinical application.

Various studies have revealed that CCR7 is expressed in various tumor cells such as B cell chronic lymphocytic leukemia, non-Hodgkin's lymphoma, breast cancer cell and malignant mammary tumor. Further it is becoming clear that CCR7 plays a role in lymph node metastasis of various cancers such as gastric cancer, melanoma, non-small cell lung cancer and T cell leukemia cell (Non-Patent Document 1). Since CCL19 and CCL21 which are ligands for CCR7 are highly expressed in lymph nodes, it is expected that selective inhibition of CCR7 function will suppress lymphatic metastasis of cancer cells.

A principal mechanism of action of an antibody drug against a membrane protein (receptor) is generally such that a cell expressing the protein is recognized by an antibody, and then removed based on complement-dependent cell lysis action (CDC) and antibody-dependent cell-mediated cytotoxicity (ADCC). However, CDC and ADCC are associated with activation of inflammatory cells such as macrophages, and are not necessarily appropriate for therapy of fibrosis. Therefore, when a monoclonal antibody capable of selectively inhibiting CCR7 is applied in therapy of fibrosis, it is preferable that the monoclonal antibody is a functional antibody capable of inhibiting CCR7 without relying on CDC or ADCC. That is, an antibody that selectively interferes with CCL19- or CCL21-dependent intracellular signal transduction of CCR7 is desired. However, it is generally difficult to acquire a functional antibody against GPCR efficiently.

Patent Document 1: JP 2009-528977 T
Non-Patent Document 1: Viola A, Luster AD "Chemokines and their receptors: drug targets in immunity and inflammation", Annu Rev Pharmacol Toxicol. 2008; 48:171-97
Non-Patent Document 2: Birkenbach, M., Josefsen, K., Yalamanchili, R., Lenoir, G., Kieff, E., "Epstein-Barr virus-induced genes: first lymphocyte-specific G protein-coupled peptide receptors", J. Virol. 67: 2209-2220, 1993.
Non-Patent Document 3: Pilling D, Fan T, Huang D, Kaul B, Gomer R H. "Identification of markers that distinguish monocyte-derived fibrocytes from monocytes, macrophages, and fibroblasts", PLoS One. 2009 Oct. 16; 4(10): e7475
Non-Patent Document 4: Wada T, Sakai N, Matsushima K, Kaneko S. "Fibrocytes: a new insight into kidney fibrosis", Kidney Int. 2007 August; 72(3):269-73.

SUMMARY OF THE INVENTION

Problems to be Solved by the Invention

It is an object of the present invention to provide a novel anti-human CCR7 antibody that is useful as a therapeutic drug for fibrosis or cancer, a pharmaceutical composition containing the anti-human CCR7 antibody and the like.

Solutions to the Problems

One aspect of the present invention for solving the aforementioned problem is an anti-human CCR7 antibody specifically binding to an extracellular domain of human CCR7, including a heavy chain complementarity determining region 3 (heavy chain CDR3) containing an amino acid sequence represented by SEQ ID NO: 7, SEQ ID NO: 17, SEQ ID NO: 27, SEQ ID NO: 37, SEQ ID NO: 47, SEQ ID NO: 57, SEQ ID NO: 67, or SEQ ID NO: 77.

Another aspect of the present invention for solving such a problem is an anti-human CCR7 antibody specifically binding to an extracellular domain of human CCR7, wherein the antibody includes complementarity determining regions 1 to 3 (CDRs 1-3) that consist of any one of amino acid sequences as the following (A1) to (A8):

(A1) having a heavy chain CDR1 containing an amino acid sequence represented by SEQ ID NO: 5, a heavy chain CDR2 containing an amino acid sequence represented by SEQ ID NO: 6, and a heavy chain CDR3 containing an amino acid sequence represented by SEQ ID NO: 7, (A2) having a heavy chain CDR1 containing an amino acid sequence represented by SEQ ID NO: 15, a heavy chain CDR2 containing an amino acid sequence represented by SEQ ID NO: 16, and a heavy chain CDR3 containing an amino acid sequence represented by SEQ ID NO: 17, (A3) having a heavy chain CDR1 containing an amino acid sequence represented by SEQ ID NO: 25, a heavy chain CDR2 containing an amino acid sequence represented by SEQ ID NO: 26, and a heavy chain CDR3 containing an amino acid sequence represented by SEQ ID NO: 27, (A4) having a heavy chain CDR1 containing an amino acid sequence represented by SEQ ID NO: 35, a heavy chain CDR2 containing an amino acid sequence represented by SEQ ID NO: 36, and a heavy chain CDR3 containing an amino acid sequence represented by SEQ ID NO: 37, (A5) having a heavy chain CDR1 containing an amino acid sequence represented by SEQ ID NO: 45, a heavy chain CDR2 containing an amino acid sequence represented by SEQ ID NO: 46, and a heavy chain CDR3 containing an amino acid sequence represented by SEQ ID NO: 47, (A6) having a heavy chain CDR1 containing an amino acid sequence represented by SEQ ID NO: 55, a heavy chain CDR2 containing an amino acid sequence represented by SEQ ID NO: 56, and a heavy chain CDR3 containing an amino acid sequence represented by SEQ ID NO: 57, (A7) having a heavy chain CDR1 containing an amino acid sequence represented by SEQ ID NO: 65, a heavy chain CDR2 containing an amino acid sequence represented by SEQ ID NO: 66, and a heavy chain CDR3 containing an amino acid sequence represented by SEQ ID NO: 67, and (A8) having a heavy chain CDR1 containing an amino acid sequence represented by SEQ ID NO: 75, a heavy chain CDR2 containing an amino acid sequence represented by SEQ ID NO: 76, and a heavy chain CDR3 containing an amino acid sequence represented by SEQ ID NO: 77.

Another aspect of the present invention for solving such a problem is an anti-human CCR7 antibody specifically binding to an extracellular domain of human CCR7, wherein the antibody includes complementarity determining regions 1 to 3 (CDRs 1-3) that consist of any one of amino acid sequences as the following (B1) to (B8):

(B1) having a heavy chain CDR1 containing an amino acid sequence represented by SEQ ID NO: 5, a heavy chain CDR2 containing an amino acid sequence represented by SEQ ID NO: 6, a heavy chain CDR3 containing an amino acid sequence represented by SEQ ID NO: 7, a light chain CDR1 containing an amino acid sequence represented by SEQ ID NO: 8, a light chain CDR2 containing an amino acid sequence represented by SEQ ID NO: 9, and a light chain CDR3 containing an amino acid sequence represented by SEQ ID NO: 10, (B2) having a heavy chain CDR1 containing an amino acid sequence represented by SEQ ID NO: 15, a heavy chain CDR2 containing an amino acid sequence represented by SEQ ID NO: 16, a heavy chain CDR3 containing an amino acid sequence represented by SEQ ID NO: 17, a light chain CDR1 containing an amino acid sequence represented by SEQ ID NO: 18, a light chain CDR2 containing an amino acid sequence represented by SEQ ID NO: 19, and a light chain CDR3 containing an amino acid sequence represented by SEQ ID NO: 20, (B3) having a heavy chain CDR1 containing an amino acid sequence represented by SEQ ID NO: 25, a heavy chain CDR2 containing an amino acid sequence represented by SEQ ID NO: 26, a heavy chain CDR3 containing an amino acid sequence represented by SEQ ID NO: 27, a light chain CDR1 containing an amino acid sequence represented by SEQ ID NO: 28, a light chain CDR2 containing an amino acid sequence represented by SEQ ID NO: 29, and a light chain CDR3 containing an amino acid sequence represented by SEQ ID NO: 30, (B4) having a heavy chain CDR1 containing an amino acid sequence represented by SEQ ID NO: 35, a heavy chain CDR2 containing an amino acid sequence represented by SEQ ID NO: 36, a heavy chain CDR3 containing an amino acid sequence represented by SEQ ID NO: 37, a light chain CDR1 containing an amino acid sequence represented by SEQ ID NO: 38, a light chain CDR2 containing an amino acid sequence represented by SEQ ID NO: 39, and a light chain CDR3 containing an amino acid sequence represented by SEQ ID NO: 40, (B5) having a heavy chain CDR1 containing an amino acid sequence represented by SEQ ID NO: 45, a heavy chain CDR2 containing an amino acid sequence represented by SEQ ID NO: 46, a heavy chain CDR3 containing an amino acid sequence represented by SEQ ID NO: 47, a light chain CDR1 containing an amino acid sequence represented by SEQ ID NO: 48, a light chain CDR2 containing an amino acid sequence represented by SEQ ID NO: 49, and a light chain CDR3 containing an amino acid sequence represented by SEQ ID NO: 50, (B6) having a heavy chain CDR1 containing an amino acid sequence represented by SEQ ID NO: 55, a heavy chain CDR2 containing an amino acid sequence represented by SEQ ID NO: 56, a heavy chain CDR3 containing an amino acid sequence represented by SEQ ID NO: 57, a light chain CDR1 containing an amino acid sequence represented by SEQ ID NO: 58, a light chain CDR2 containing an amino acid sequence represented by SEQ ID NO: 59, and a light chain CDR3 containing an amino acid sequence represented by SEQ ID NO: 60, (B7) having a heavy chain CDR1 containing an amino acid sequence represented by SEQ ID NO: 65, a heavy chain CDR2 containing an amino acid sequence represented by SEQ ID NO: 66, a heavy chain CDR3 containing an amino acid sequence represented by SEQ ID NO: 67, a light chain CDR1 containing an amino acid sequence represented by SEQ ID NO: 68, a light chain CDR2 containing an amino acid sequence represented by SEQ ID NO: 69, and a light chain CDR3 containing an amino acid sequence represented by SEQ ID NO: 70, and (B8) having a heavy chain CDR1 containing an amino acid sequence represented by SEQ ID NO: 75, a heavy chain CDR2 containing an amino acid sequence represented by SEQ ID NO: 76, a heavy chain CDR3 containing an amino acid sequence represented by SEQ ID NO: 77, a light chain CDR1 containing an amino acid sequence represented by SEQ ID NO: 78, a light chain CDR2 containing an amino acid sequence represented by SEQ ID NO: 79, and a light chain CDR3 containing an amino acid sequence represented by SEQ ID NO: 80.

Another aspect of the present invention for solving such a problem is an anti-human CCR7 antibody specifically binding to an extracellular domain of human CCR7, wherein the antibody includes a heavy chain variable region and a light chain variable region that consist of any one of amino acid sequences as the following (C1) to (C8):

(C1) having a heavy chain variable region containing an amino acid sequence represented by SEQ ID NO: 2, and a light chain variable region containing an amino acid sequence represented by SEQ ID NO: 4, (C2) having a heavy chain variable region containing an amino acid sequence represented by SEQ ID NO: 12, and a light chain variable region containing an amino acid sequence represented by SEQ ID NO: 14, (C3) having a heavy chain variable region containing an amino acid sequence represented by SEQ ID NO: 22, and a light chain variable region containing an amino acid sequence represented by SEQ ID NO: 24, (C4) having a heavy chain variable region containing an amino acid sequence represented by SEQ ID NO: 32, and a light chain variable region containing an amino acid sequence represented by SEQ ID NO: 34, (C5) having a heavy chain variable region containing an amino acid sequence represented by SEQ ID NO: 42, and a light chain variable region containing an amino acid sequence represented by SEQ ID NO: 44, (C6) having a heavy chain variable region containing an amino acid sequence represented by SEQ ID NO: 52, and a light chain variable region containing an amino acid sequence represented by SEQ ID NO: 54, (C7) having a heavy chain variable region containing an amino acid sequence represented by SEQ ID NO: 62, and a light chain variable region containing an amino acid sequence represented by SEQ ID NO: 64, and (C8) having a heavy chain variable region containing an amino acid sequence represented by SEQ ID NO: 72, and a light chain variable region containing an amino acid sequence represented by SEQ ID NO: 74.

Preferably, it has an activity of interfering with a CCR7-dependent intracellular signal transduction mechanism caused by CCR7 ligand stimulation.

Preferably, it is a humanized antibody or a chimeric antibody.

Preferably, it is an antibody fragment, a single-chain antibody, or a diabody.

Another aspect of the present invention is an anti-human CCR7 antibody specifically binding to an extracellular domain of human CCR7, which is produced by R7-01 (FERM BP-11369), R7-02 (FERM BP-11404), R7-05 (FERM BP-11371), R7-09 (FERM BP-11372), R7-11 (FERM BP-11373), R7-18 (FERM BP-11374), R7-25 (FERM BP-11375), or R7-47 (FERM BP-11376).

Another aspect of the present invention is an anti-human CCR7 antibody that binds to the same epitope as that of the above-described anti-human CCR7 antibody.

Still another aspect of the present invention is a hybridoma which is R7-01 (FERM BP-11369), R7-02 (FERM BP-11404), R7-05 (FERM BP-11371), R7-09 (FERM BP-11372), R7-11 (FERM BP-11373), R7-18 (FERM BP-11374), R7-25 (FERM BP-11375), or R7-47 (FERM BP-11376).

Still another aspect of the present invention is a nucleic acid encoding a heavy chain variable region or a light chain variable region of the anti-human CCR7 antibody of the present invention.

Preferably, it has a nucleotide sequence represented by SEQ ID NO: 1, SEQ ID NO: 3, SEQ ID NO: 11, SEQ ID NO: 13, SEQ ID NO: 21, SEQ ID NO: 23, SEQ ID NO: 31, SEQ ID NO: 33, SEQ ID NO: 41, SEQ ID NO: 43, SEQ ID NO: 51, SEQ ID NO: 53, SEQ ID NO: 61, SEQ ID NO: 63, SEQ ID NO: 71, or SEQ ID NO: 73.

Still another aspect of the present invention is a vector including the nucleic acid.

Still another aspect of the present invention is a cell into which the vector is introduced.

Still another aspect of the present invention is a pharmaceutical composition including the anti-human CCR7 antibody of the present invention and a pharmaceutically acceptable agent.

Preferably, it interferes with a CCR7-dependent intracellular signal transduction mechanism caused by a CCR7 ligand.

Preferably, it is used for therapy of tissue fibrosis.

Preferably, the tissue fibrosis is fibrosis selected from the group consisting of hepatic fibrosis, renal fibrosis, pulmonary fibrosis, skin fibrosis, cardiovascular fibrosis, gastrointestinal fibrosis and other fibrous diseases.

Preferably, the hepatic fibrosis is selected from the group consisting of hepatic cirrhosis, ischemic reperfusion, post-hepatic transplant disorder, necrotic hepatitis, hepatitis B, hepatitis C, primary biliary cirrhosis, and primary sclerosing cholangitis.

Preferably, the hepatic cirrhosis is caused by at least one selected from the group consisting of induction by alcohol, induction by a drug, and induction by chemical induction.

Preferably, the renal fibrosis is selected from the group consisting of proliferative glomerulonephritis, sclerotic glomerulonephritis, nephrogenic fibrosing dermopathy, diabetic nephropathy, renal tubule interstitial fibrosis, and focal segmental glomerulosclerosis.

Preferably, the pulmonary fibrosis is selected from the group consisting of pulmonary interstitial fibrosis, drug-induced sarcoidosis, pulmonary fibrosis, idiopathic pulmonary fibrosis, asthma, chronic obstructive pulmonary disease, diffuse pulmonary alveolar injury disease, pulmonary hypertension, and neonatal bronchopulmonary dysplasia.

Preferably, the skin fibrosis is selected from the group consisting of scleroderma, keloid scarring, psoriasis, hypertrophic scarring, and pseudo scleroderma.

Preferably, the cardiovascular fibrosis is selected from the group consisting of atherosclerosis, coronary restenosis, congestive cardiomyopathy, heart failure, cardiac transplantation, and myocardial fibrosis.

Preferably, the gastrointestinal fibrosis is selected from the group consisting of collagenous colitis, villous atrophy, crypt hyperplasia, polyp formation, fibrosis of Crohn's disease, gastric ulcer healing, and post-abdominal adhesion surgery scar.

Preferably, the fibrosis has a condition arising from bone-related fibrosing disease and is rheumatoid pannus formation.

Preferably, it is used for therapy of cancer metastasis.

Preferably, the cancer is selected from the group consisting of pharyngeal cancer, chondrosarcoma, colon cancer, pancreatic cancer, leukemia, and breast cancer.

Still another aspect of the present invention is an antibody-immobilized carrier including the anti-human CCR7 antibody of the present invention immobilized to a carrier.

Preferably, it is used for removing a CCR7-expressing cell from a bodily fluid by contact with blood containing the CCR7-expressing cell.

Advantages of the Invention

According to the anti-human CCR7 antibody of the present invention, it is possible to provide a novel pharmaceutical product against fibrosis, lymphocytic cancer metastasis and the like that are difficult to be cured.

The same applies to the hybridoma of the present invention, and it allows production of an anti-human CCR7 antibody which is to be an active ingredient of a novel pharmaceutical product against fibrosis, lymphocytic cancer metastasis and the like that are difficult to be cured.

According to the nucleic acid of the present invention, it is possible to produce the antibody of the present invention by recombination techniques. It is also applicable to a gene therapy.

The same applies to the vector of the present invention, and the antibody of the present invention can be produced by recombination techniques. It is also applicable to a gene therapy.

The same applies to the cell of the present invention, it is possible to produce the antibody of the present invention by recombination techniques.

According to the pharmaceutical composition of the present invention, it is possible to provide a novel pharmaceutical product against fibrosis, lymphocytic cancer metastasis and the like that are difficult to be cured.

According to the antibody-immobilized carrier of the present invention, it is possible to selectively remove CCR7-expressing cells from blood of a patient suffering from fibrosis, cancer or the like.

BRIEF DESCRIPTION OF THE DRAWINGS

FIG. 1 Explanatory views showing amino acid sequences of variable regions of R7-01 and positions of CDRs 1-3, wherein (a) represents a heavy chain variable region, and (b) represents a light chain variable region.

FIG. 2 Explanatory views showing amino acid sequences of variable regions of R7-02 and positions of CDRs 1-3, wherein (a) represents a heavy chain variable region, and (b) represents a light chain variable region.

FIG. 3 Explanatory views showing amino acid sequences of variable regions of R7-05 and positions of CDRs 1-3, wherein (a) represents a heavy chain variable region, and (b) represents a light chain variable region.

FIG. 4 Explanatory views showing amino acid sequences of variable regions of R7-09 and positions of CDRs 1-3, wherein (a) represents a heavy chain variable region, and (b) represents a light chain variable region.

FIG. 5 Explanatory views showing amino acid sequences of variable regions of R7-11 and positions of CDRs 1-3, wherein (a) represents a heavy chain variable region, and (b) represents a light chain variable region.

FIG. 6 Explanatory views showing amino acid sequences of variable regions of R7-18 and positions of CDRs 1-3, wherein (a) represents a heavy chain variable region, and (b) represents a light chain variable region.

FIG. 7 Explanatory views showing amino acid sequences of variable regions of R7-25 and positions of CDRs 1-3, wherein (a) represents a heavy chain variable region, and (b) represents a light chain variable region.

FIG. 8 Explanatory views showing amino acid sequences of variable regions of R7-47 and positions of CDRs 1-3, wherein (a) represents a heavy chain variable region, and (b) represents a light chain variable region.

MODE FOR CARRYING OUT THE INVENTION

Figure 9:
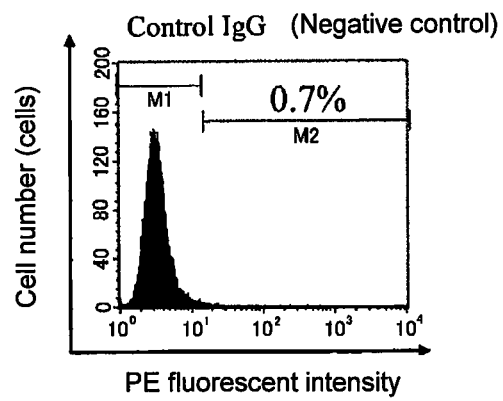
FIG. 9 A histogram showing an analytical result of interaction between human CCR7 gene-introduced cells and mouse control IgG.

First, description will be given for human CCR7 that is specifically recognized by the antibody of the present invention mainly focusing on its structure. As described above, CCR7 is one kind of G protein-coupled receptors (GPCR), and is present in the condition that it penetrates the cell membrane seven times, with its N-terminal being outside the cell and its C-terminal being inside the cell. A gene (cDNA) encoding human CCR7 is already isolated, and the amino acid sequence of human CCR7 is already known. The sequence information may be obtained, for example, from database of GenBank or the like (for example, GenBank: EAW60669.1). As one example, a nucleotide sequence of a human CCR7 gene and an amino acid sequence corresponding to the nucleotide sequence are shown in SEQ ID NO: 81, and only the amino acid sequence is shown in SEQ ID NO: 82.

Respective domains in human CCR7 are considered to correspond to the following parts in the amino acid sequence shown in SEQ ID NO: 82. Amino acid numbers are shown on the left, and respective domains are shown on the right. Some variation may arise with respect to borders between respective domains.

1 to 24: Membrane translocation signal peptide sequence (cut and removed after expression)
25 to 59: N-terminal domain
87 to 95: Intracellular first loop domain
117 to 130: Extracellular first loop domain
153 to 170: Intracellular second loop domain
192 to 219: Extracellular second loop domain
248 to 263: Intracellular third loop domain
290 to 313: Extracellular third loop domain
332 to 378: C-terminal domain Various variants such as amino acid substituted variants are known for human CCR7 besides one shown in SEQ ID NO: 82. "Human CCR7" in the present invention includes the aforementioned variants as far as it has an extracellular domain and the function of CCR7.

The anti-human CCR7 antibody of the present invention (hereinafter, also may be simply abbreviated as "antibody of the present invention") specifically binds to an extracellular domain of human CCR7. In one aspect (first aspect), the antibody of the present invention has a heavy chain complementarity determining region 3 (heavy chain CDR3) containing an amino acid sequence represented by SEQ ID NO: 7, SEQ ID NO: 17, SEQ ID NO: 27, SEQ ID NO: 37, SEQ ID NO: 47, SEQ ID NO: 57, SEQ ID NO: 67, or SEQ ID NO: 77.

In another aspect (second aspect), the antibody of the present invention includes complementarity determining regions 1 to 3 (CDRs 1-3) that consist of any one of amino acid sequences as the following (A1) to (A8):

(A1) having a heavy chain CDR1 containing an amino acid sequence represented by SEQ ID NO: 5, a heavy chain CDR2 containing an amino acid sequence represented by SEQ ID NO: 6, and a heavy chain CDR3 containing an amino acid sequence represented by SEQ ID NO: 7, (A2) having a heavy chain CDR1 containing an amino acid sequence represented by SEQ ID NO: 15, a heavy chain CDR2 containing an amino acid sequence represented by SEQ ID NO: 16, and a heavy chain CDR3 containing an amino acid sequence represented by SEQ ID NO: 17, (A3) having a heavy chain CDR1 containing an amino acid sequence represented by SEQ ID NO: 25, a heavy chain CDR2 containing an amino acid sequence represented by SEQ ID NO: 26, and a heavy chain CDR3 containing an amino acid sequence represented by SEQ ID NO: 27, (A4) having a heavy chain CDR1 containing an amino acid sequence represented by SEQ ID NO: 35, a heavy chain CDR2 containing an amino acid sequence represented by SEQ ID NO: 36, and a heavy chain CDR3 containing an amino acid sequence represented by SEQ ID NO: 37, (A5) having a heavy chain CDR1 containing an amino acid sequence represented by SEQ ID NO: 45, a heavy chain CDR2 containing an amino acid sequence represented by SEQ ID NO: 46, and a heavy chain CDR3 containing an amino acid sequence represented by SEQ ID NO: 47, (A6) having a heavy chain CDR1 containing an amino acid sequence represented by SEQ ID NO: 55, a heavy chain CDR2 containing an amino acid sequence represented by SEQ ID NO: 56, and a heavy chain CDR3 containing an amino acid sequence represented by SEQ ID NO: 57, (A7) having a heavy chain CDR1 containing an amino acid sequence represented by SEQ ID NO: 65, a heavy chain CDR2 containing an amino acid sequence represented by SEQ ID NO: 66, and a heavy chain CDR3 containing an amino acid sequence represented by SEQ ID NO: 67, and (A8) having a heavy chain CDR1 containing an amino acid sequence represented by SEQ ID NO: 75, a heavy chain CDR2 containing an amino acid sequence represented by SEQ ID NO: 76, and a heavy chain CDR3 containing an amino acid sequence represented by SEQ ID NO: 77.

In another aspect (third aspect), the antibody of the present invention includes complementarity determining regions 1 to 3 (CDRs 1-3) that consist of any one of amino acid sequences as the following (B1) to (B8):

(B1) having a heavy chain CDR1 containing an amino acid sequence represented by SEQ ID NO: 5, a heavy chain CDR2 containing an amino acid sequence represented by SEQ ID NO: 6, a heavy chain CDR3 containing an amino acid sequence represented by SEQ ID NO: 7, a light chain CDR1 containing an amino acid sequence represented by SEQ ID NO: 8, a light chain CDR2 containing an amino acid sequence represented by SEQ ID NO: 9, and a light chain CDR3 containing an amino acid sequence represented by SEQ ID NO: 10, (B2) having a heavy chain CDR1 containing an amino acid sequence represented by SEQ ID NO: 15, a heavy chain CDR2 containing an amino acid sequence represented by SEQ ID NO: 16, a heavy chain CDR3 containing an amino acid sequence represented by SEQ ID NO: 17, a light chain CDR1 containing an amino acid sequence represented by SEQ ID NO: 18, a light chain CDR2 containing an amino acid sequence represented by SEQ ID NO: 19, and a light chain CDR3 containing an amino acid sequence represented by SEQ ID NO: 20, (B3) having a heavy chain CDR1 containing an amino acid sequence represented by SEQ ID NO: 25, a heavy chain CDR2 containing an amino acid sequence represented by SEQ ID NO: 26, a heavy chain CDR3 containing an amino acid sequence represented by SEQ ID NO: 27, a light chain CDR1 containing an amino acid sequence represented by SEQ ID NO: 28, a light chain CDR2 containing an amino acid sequence represented by SEQ ID NO: 29, and a light chain CDR3 containing an amino acid sequence represented by SEQ ID NO: 30, (B4) having a heavy chain CDR1 containing an amino acid sequence represented by SEQ ID NO: 35, a heavy chain CDR2 containing an amino acid sequence represented by SEQ ID NO: 36, a heavy chain CDR3 containing an amino acid sequence represented by SEQ ID NO: 37, a light chain CDR1 containing an amino acid sequence represented by SEQ ID NO: 38, a light chain CDR2 containing an amino acid sequence represented by SEQ ID NO: 39, and a light chain CDR3 containing an amino acid sequence represented by SEQ ID NO: 40, (B5) having a heavy chain CDR1 containing an amino acid sequence represented by SEQ ID NO: 45, a heavy chain CDR2 containing an amino acid sequence represented by SEQ ID NO: 46, a heavy chain CDR3 containing an amino acid sequence represented by SEQ ID NO: 47, a light chain CDR1 containing an amino acid sequence represented by SEQ ID NO: 48, a light chain CDR2 containing an amino acid sequence represented by SEQ ID NO: 49, and a light chain CDR3 containing an amino acid sequence represented by SEQ ID NO: 50, (B6) having a heavy chain CDR1 containing an amino acid sequence represented by SEQ ID NO: 55, a heavy chain CDR2 containing an amino acid sequence represented by SEQ ID NO: 56, a heavy chain CDR3 containing an amino acid sequence represented by SEQ ID NO: 57, a light chain CDR1 containing an amino acid sequence represented by SEQ ID NO: 58, a light chain CDR2 containing an amino acid sequence represented by SEQ ID NO: 59, and a light chain CDR3 containing an amino acid sequence represented by SEQ ID NO: 60, (B7) having a heavy chain CDR1 containing an amino acid sequence represented by SEQ ID NO: 65, a heavy chain CDR2 containing an amino acid sequence represented by SEQ ID NO: 66, a heavy chain CDR3 containing an amino acid sequence represented by SEQ ID NO: 67, a light chain CDR1 containing an amino acid sequence represented by SEQ ID NO: 68, a light chain CDR2 containing an amino acid sequence represented by SEQ ID NO: 69, and a light chain CDR3 containing an amino acid sequence represented by SEQ ID NO: 70, and (B8) having a heavy chain CDR1 containing an amino acid sequence represented by SEQ ID NO: 75, a heavy chain CDR2 containing an amino acid sequence represented by SEQ ID NO: 76, a heavy chain CDR3 containing an amino acid sequence represented by SEQ ID NO: 77, a light chain CDR1 containing an amino acid sequence represented by SEQ ID NO: 78, a light chain CDR2 containing an amino acid sequence represented by SEQ ID NO: 79, and a light chain CDR3 containing an amino acid sequence represented by SEQ ID NO: 80.

In another aspect (fourth aspect), the antibody of the present invention includes a heavy chain variable region (hereinafter, may be abbreviated as "VH") and a light chain variable region (hereinafter, may be abbreviated as "VL") that consist of any one of amino acid sequences as the following (C1) to (C8):

(C1) having a heavy chain variable region containing an amino acid sequence represented by SEQ ID NO: 2, and a light chain variable region containing an amino acid sequence represented by SEQ ID NO: 4, (C2) having a heavy chain variable region containing an amino acid sequence represented by SEQ ID NO: 12, and a light chain variable region containing an amino acid sequence represented by SEQ ID NO: 14, (C3) having a heavy chain variable region containing an amino acid sequence represented by SEQ ID NO: 22, and a light chain variable region containing an amino acid sequence represented by SEQ ID NO: 24, (C4) having a heavy chain variable region containing an amino acid sequence represented by SEQ ID NO: 32, and a light chain variable region containing an amino acid sequence represented by SEQ ID NO: 34, (C5) having a heavy chain variable region containing an amino acid sequence represented by SEQ ID NO: 42, and a light chain variable region containing an amino acid sequence represented by SEQ ID NO: 44, (C6) having a heavy chain variable region containing an amino acid sequence represented by SEQ ID NO: 52, and a light chain variable region containing an amino acid sequence represented by SEQ ID NO: 54, (C7) having a heavy chain variable region containing an amino acid sequence represented by SEQ ID NO: 62, and a light chain variable region containing an amino acid sequence represented by SEQ ID NO: 64, and (C8) having a heavy chain variable region containing an amino acid sequence represented by SEQ ID NO: 72, and a light chain variable region containing an amino acid sequence represented by SEQ ID NO: 74.

SEQ ID NO: 5 (heavy chain CDR1), SEQ ID NO: 6 (heavy chain CDR2), and SEQ ID NO: 7 (heavy chain CDR3) respectively correspond to the parts of amino acid numbers 27 to 35, 50 to 66, and 97 to 112 in SEQ ID NO: 2 (VH) (FIG. 1(a)).

SEQ ID NO: 8 (light chain CDR1), SEQ ID NO: 9 (light chain CDR2), and SEQ ID NO: 10 (light chain CDR3) respectively correspond to the parts of amino acid numbers 24 to 39, 55 to 68, and 94 to 102 in SEQ ID NO: 4 (VL) (FIG. 1(b)).

SEQ ID NO: 15 (heavy chain CDR1), SEQ ID NO: 16 (heavy chain CDR2), and SEQ ID NO: 17 (heavy chain CDR3) respectively correspond to the parts of amino acid numbers 43 to 51, 66 to 82, and 113 to 124 in SEQ ID NO: 12 (VH) (FIG. 2(a)).

SEQ ID NO: 18 (light chain CDR1), SEQ ID NO: 19 (light chain CDR2), and SEQ ID NO: 20 (light chain CDR3) respectively correspond to the parts of amino acid numbers 24 to 37, 53 to 59, and 87 to 99 in SEQ ID NO: 14 (VL) (FIG. 2(b)).

SEQ ID NO: 25 (heavy chain CDR1), SEQ ID NO: 26 (heavy chain CDR2), and SEQ ID NO: 27 (heavy chain CDR3) respectively correspond to the parts of amino acid numbers 30 to 38, 53 to 68, and 100 to 111 in SEQ ID NO: 22 (VH) (FIG. 3(a)).

SEQ ID NO: 28 (light chain CDR1), SEQ ID NO: 29 (light chain CDR2), and SEQ ID NO: 30 (light chain CDR3) respectively correspond to the parts of amino acid numbers 23 to 36, 52 to 58, and 91 to 99 in SEQ ID NO: 24 (VL) (FIG. 3(b)).

SEQ ID NO: 35 (heavy chain CDR1), SEQ ID NO: 36 (heavy chain CDR2), and SEQ ID NO: 37 (heavy chain CDR3) respectively correspond to the parts of amino acid numbers 28 to 36, 51 to 67, and 98 to 109 in SEQ ID NO: 32 (VH) (FIG. 4(a)).

SEQ ID NO: 38 (light chain CDR1), SEQ ID NO: 39 (light chain CDR2), and SEQ ID NO: 40 (light chain CDR3) respectively correspond to the parts of amino acid numbers 23 to 36, 52 to 58, and 91 to 99 in SEQ ID NO: 34 (VL) (FIG. 4(b)).

SEQ ID NO: 45 (heavy chain CDR1), SEQ ID NO: 46 (heavy chain CDR2), and SEQ ID NO: 47 (heavy chain CDR3) respectively correspond to the parts of amino acid numbers 29 to 37, 52 to 68, and 98 to 110 in SEQ ID NO: 42 (VH) (FIG. 5(a)).

SEQ ID NO: 48 (light chain CDR1), SEQ ID NO: 49 (light chain CDR2), and SEQ ID NO: 50 (light chain CDR3) respectively correspond to the parts of amino acid numbers 24 to 39, 55 to 61, and 94 to 102 in SEQ ID NO: 44 (VL) (FIG. 5(b)).

SEQ ID NO: 55 (heavy chain CDR1), SEQ ID NO: 56 (heavy chain CDR2), and SEQ ID NO: 57 (heavy chain CDR3) respectively correspond to the parts of amino acid numbers 30 to 37, 53 to 69, and 99 to 111 in SEQ ID NO: 52 (VH) (FIG. 6(a)).

SEQ ID NO: 58 (light chain CDR1), SEQ ID NO: 59 (light chain CDR2), and SEQ ID NO: 60 (light chain CDR3) respectively correspond to the parts of amino acid numbers 24 to 39, 55 to 61, and 94 to 102 in SEQ ID NO: 54 (VL) (FIG. 6(b)).

SEQ ID NO: 65 (heavy chain CDR1), SEQ ID NO: 66 (heavy chain CDR2), and SEQ ID NO: 67 (heavy chain CDR3) respectively correspond to the parts of amino acid numbers 30 to 41, 54 to 69, and 100 to 111 in SEQ ID NO: 62 (VH) (FIG. 7(a)).

SEQ ID NO: 68 (light chain CDR1), SEQ ID NO: 69 (light chain CDR2), and SEQ ID NO: 70 (light chain CDR3) respectively correspond to the parts of amino acid numbers 24 to 39, 56 to 62, and 95 to 102 in SEQ ID NO: 64 (VL) (FIG. 7(b)).

SEQ ID NO: 75 (heavy chain CDR1), SEQ ID NO: 76 (heavy chain CDR2), and SEQ ID NO: 77 (heavy chain CDR3) respectively correspond to the parts of amino acid numbers 27 to 35, 50 to 66, and 96 to 109 in SEQ ID NO: 72 (VH) (FIG. 8(a)).

SEQ ID NO: 78 (light chain CDR1), SEQ ID NO: 79 (light chain CDR2), and SEQ ID NO: 80 (light chain CDR3) respectively correspond to the parts of amino acid numbers 24 to 39, 55 to 61, and 94 to 102 in SEQ ID NO: 74 (VL) (FIG. 8(b)).

In the present invention, the wording "antibody" may be replaced with "immunoglobulin".

The antibody in the present invention includes a functional fragment thereof. Here, "functional fragment of antibody" refers to a partial fragment of antibody (namely, immunoglobulin) having at least one action on an antigen. Examples of such partial fragments include F(ab')$_2$, Fab, Fv, disulfide-bonded Fv, single chain antibody (scFv, VH-VL), VH, and polymer thereof, and a fused body of them and a heavy chain CH3 region. Also examples thereof include CDRs such as CDR1, CDR2 and CDR3, a connected body of these CDRs, and a fused body of the CDRs or CDR connected body and a heavy chain CH3 region. That is, the antibody of the present invention includes the partial fragments of the antibody as described above as far as they specifically bind to an extracellular domain of human CCR7. A partial fragment of the antibody may be also called "antibody fragment".

Further, the antibody of the present invention may be a multi-specific antibody. An example thereof includes a diabody which is one kind of double-specific antibody (WO 93/11161 etc.).

When the antibody of the present invention is a functional fragment, for example, the effect as will be described later is achieved. That is, when a full-length antibody such as type IgG is used in application of the anti-human CCR7 antibody of the present invention in medical application as will be described later, the target tissue is damaged in addition to signal inhibition of the target receptor, and this may lead a side effect. In such a case, by employing the "functional fragment of an antibody" using only a variable region, it becomes easy to avoid the side effect as described above.

The class (isotype) of the antibody of the present invention is not particularly limited. For example, it may be of any classes including IgG, IgM, IgA, IgD, IgE and the like. Further, the subclass of the antibody of the present invention is not particularly limited, and it may be of any subclasses including IgG1, IgG2, IgG3 and the like, as far as it is IgG.

In a preferred embodiment, the antibody has an activity of interfering with a CCR7-dependent intracellular signal transduction mechanism caused by CCR7 ligand stimulation.

Still another aspect (fifth aspect) in the antibody of the present invention is an anti-human CCR7 antibody produced by R7-01 (FERN BP-11369), R7-02 (FERN BP-11404), R7-05 (FERN BP-11371), R7-09 (FERN BP-11372), R7-11 (FERN BP-11373), R7-18 (FERN BP-11374), R7-25 (FERN BP-11375), or R7-47 (FERN BP-11376). The antibodies produced by these eight kinds of hybridomas specifically bind to an extracellular domain of human CCR7.

As will be described in detail in the later-described example, each of eight kinds of antibodies produced by these hybridomas has a heavy chain variable region (VH), a light chain variable region (VL), and each CDR having the specific amino acid sequences described above. Table 1 collectively shows the relationship between SEQ ID NOs of amino acid sequences of VH, VL and each CDR, and a corresponding clone.

TABLE 1

| Name of clone | VH or VL | SEQ ID NO: | CDR | SEQ ID NO: |
|---|---|---|---|---|
| R7-01 | VH | 2 | CDR1 | 5 |
|  |  |  | CDR2 | 6 |
|  |  |  | CDR3 | 7 |
|  | VL | 4 | CDR1 | 8 |
|  |  |  | CDR2 | 9 |
|  |  |  | CDR3 | 10 |
| R7-02 | VH | 12 | CDR1 | 15 |
|  |  |  | CDR2 | 16 |
|  |  |  | CDR3 | 17 |
|  | VL | 14 | CDR1 | 18 |
|  |  |  | CDR2 | 19 |
|  |  |  | CDR3 | 20 |
| R7-05 | VH | 22 | CDR1 | 25 |
|  |  |  | CDR2 | 26 |
|  |  |  | CDR3 | 27 |
|  | VL | 24 | CDR1 | 28 |
|  |  |  | CDR2 | 29 |
|  |  |  | CDR3 | 30 |
| R7-09 | VH | 32 | CDR1 | 35 |
|  |  |  | CDR2 | 36 |
|  |  |  | CDR3 | 37 |
|  | VL | 34 | CDR1 | 38 |
|  |  |  | CDR2 | 39 |
|  |  |  | CDR3 | 40 |
| R7-11 | VH | 42 | CDR1 | 45 |
|  |  |  | CDR2 | 46 |
|  |  |  | CDR3 | 47 |
|  | VL | 44 | CDR1 | 48 |
|  |  |  | CDR2 | 49 |
|  |  |  | CDR3 | 50 |
| R7-18 | VH | 52 | CDR1 | 55 |
|  |  |  | CDR2 | 56 |
|  |  |  | CDR3 | 57 |
|  | VL | 54 | CDR1 | 58 |
|  |  |  | CDR2 | 59 |
|  |  |  | CDR3 | 60 |
| R7-25 | VH | 62 | CDR1 | 65 |
|  |  |  | CDR2 | 66 |
|  |  |  | CDR3 | 67 |
|  | VL | 64 | CDR1 | 68 |
|  |  |  | CDR2 | 69 |
|  |  |  | CDR3 | 70 |
| R7-47 | VH | 72 | CDR1 | 75 |
|  |  |  | CDR2 | 76 |
|  |  |  | CDR3 | 77 |
|  | VL | 74 | CDR1 | 78 |
|  |  |  | CDR2 | 79 |
|  |  |  | CDR3 | 80 |

The foregoing eight kinds of hybridomas that produce the antibodies of the present invention are deposited onto the National Institute of Advanced Industrial Science and Technology, International Patent Organism Depositary (IPOD, Address: Central 6, 1-1, Higashi 1-chome, Tsukuba-shi, Ibaraki-ken, Japan). The details of deposit are as follows.

Indication: R7-01
Accession number: FERM BP-11369
Date of accession: Jul. 28, 2010
(transferred from FERM-21988 deposited on Jul. 28, 2010)
Indication: R7-02
Accession number: FERM BP-11404
Date of accession: Jul. 28, 2010
(transferred from FERM-21989 deposited on Jul. 28, 2010)
Indication: R7-05
Accession number: FERM BP-11371
Date of accession: Jul. 28, 2010
(transferred from FERM-21990 deposited on Jul. 28, 2010)
Indication: R7-09
Accession number: FERM BP-11372
Date of accession: Jul. 28, 2010
(transferred from FERM-21991 deposited on Jul. 28, 2010)
Indication: R7-11
Accession number: FERM BP-11373
Date of accession: Jul. 28, 2010
(transferred from FERM-21992 deposited on Jul. 28, 2010)
Indication: R7-18
Accession number: FERM BP-11374
Date of accession: Jul. 28, 2010
(transferred from FERM-21993 deposited on Jul. 28, 2010)
Indication: R7-25
Accession number: FERM BP-11375
Date of accession: Jul. 28, 2010
(transferred from FERM-21994 deposited on Jul. 28, 2010)
Indication: R7-47
Accession number: FERM BP-11376
Date of accession: Jul. 28, 2010
(transferred from FERM-21995 deposited on Jul. 28, 2010)

The extracellular domain of human CCR7 to which the antibody of the present invention specifically binds may be any one of N-terminal domain, extracellular first loop domain, extracellular second loop domain, and extracellular third loop domain. The antibody of the present invention may bind to either one or two or more of these extracellular domains.

The antibody of the present invention also includes anti-human CCR7 antibodies that bind to the same epitope as that of the anti-human CCR7 antibodies according to the first to fifth aspects as described above. In other words, the antibody of the present invention includes anti-human CCR7 antibodies having a CDR that is "functionally equivalent" to the CDRs of the anti-human CCR7 antibodies according to the first to fifth aspects. For example, epitopes of eight kinds of anti-human CCR7 antibodies that will be concretely described in the later-described examples may be analyzed by an epitope mapping method using partial peptide of human CCR7 or the like. Then, using a synthetic peptide containing the identified epitope as an antigen, anti-human CCR7 antibodies that bind to the same epitope as that of the aforementioned eight kinds of anti-human CCR7 antibodies may be obtained. Further, amino acid sequences of the heavy chain variable region and the light chain variable region of the obtained anti-human CCR7 antibody may be determined, and then amino acid sequences of the heavy chain CDRs 1-3 and the light chain CDRs 1-3 may be identified.

Examples of the amino acid sequences of "functionally equivalent" CDR in the anti-human CCR7 antibody include amino acid sequences in which one or several, preferably one to five, more preferably one to three, further preferably one amino acid is deleted, substituted or added from/to the original amino acid sequences (SEQ ID NOs: 5-10, 15-20, 25-30, 35-40, 45-50, 55-60, 65-70, 75-80), and having the equivalent function as CDR. Other examples include amino acid sequences having a homology of 80% or higher, preferably 90% or higher, and more preferably 95% or higher with the original amino acid sequences as described above, and having the equivalent function as CDR.

As a method for examining whether two antibodies recognize the same epitope, a method based on a competition experiment can be recited. For example, when binding between the eight kinds of anti-human CCR7 antibodies which are the first antibody and the receptors is competitively inhibited by the second antibody which is an objective to be tested, it can be determined that the second antibody binds to the same epitope as that of the first antibody.

The nucleic acid of the present invention encodes a heavy chain variable region (VH) or a light chain variable region (VL) in the antibody of the present invention. That is, The nucleic acid of the present invention includes a nucleic acid that encodes VH or VL of the anti-human CCR7 antibody having a heavy chain CDR3 containing an amino acid sequence represented by SEQ ID NO: 7, SEQ ID NO: 17, SEQ ID NO: 27, SEQ ID NO: 37, SEQ ID NO: 47, SEQ ID NO: 57, SEQ ID NO: 67, or SEQ ID NO: 77 according to the first aspect. Further, a nucleic acid encoding VH or VL satisfying any one of the above (A1) to (A8) according to the second aspect is included in the nucleic acid of the present invention. Further, a nucleic acid encoding VH or VL satisfying any one of the above (B1) to (B8) according to the third aspect is included in the nucleic acid of the present invention. Further, a nucleic acid encoding VH or VL satisfying any one of the above (C1) to (C8) according to the fourth aspect is included in the nucleic acid of the present invention. Concrete examples of these nucleic acids include nucleic acids having a nucleotide sequence represented by SEQ ID NO: 1, SEQ ID NO: 3, SEQ ID NO: 11, SEQ ID NO: 13, SEQ ID NO: 21, SEQ ID NO: 23, SEQ ID NO: 31, SEQ ID NO: 33, SEQ ID NO: 41, SEQ ID NO: 43, SEQ ID NO: 51, SEQ ID NO: 53, SEQ ID NO: 61, SEQ ID NO: 63, SEQ ID NO: 71, or SEQ ID NO: 73.

The nucleic acid of the present invention may be acquired from the above eight kinds of hybridomas using PCR or the like.

The vector of the present invention contains the nucleic acid of the present invention. The kind of the vector is not particularly limited, and may be appropriately selected depending on the kind or the like of the host cell into which the vector is to be introduced thereafter. The vector of the present invention includes a vector for a gene therapy. In this case, the vector itself may be directly administered into a living body.

The cell of the present invention has the vector of the present invention introduced therein. The kind of the cell is not particularly limited insofar as the introduced vector functions therein. Examples thereof include animal cells (COS cell, CHO cell and the like), yeast, bacteria (*Escherichia coli* and the like), plant cells and insect cells.

The antibody of the present invention may be produced, for example, in the following manner.

(Production by Hybridoma)

One of the foregoing eight kinds of hybridomas is cultured, and the antibody of the present invention may be produced from the culture. As a culturing method, a method commonly used as a method for culturing a hybridoma may be directly applied. For example, the hybridoma is cultured in a culture medium for an animal cell such as DMEM or RPMI1640, and the antibody of the present invention may be obtained from the supernatant of the culture. When the hybridoma is cultured in an abdominal cavity of an animal, the antibody of the present invention may be obtained from ascites sampled from the animal.

(Production by Gene Recombination Technique)

The antibody of the present invention may be produced by using gene recombination techniques. In particular, when a chimeric antibody, a humanized antibody, a functional fragment of antibody or the like is produced, it is general to produce it by gene recombination techniques.

First, a method for producing an antibody having a heavy chain variable region and a light chain variable region including any one of the above (C1) to (C8) according to the fourth aspect will be described while taking production of a chimeric antibody as an example. Here, the "chimeric antibody" refers to an antibody having a heavy chain variable region (VH) and a light chain variable region (VL) derived from an animal other than human, and other regions such as a heavy chain constant region (CH) and a light chain constant region (CL) derived from human.

First, DNA encoding an amino acid sequence (VH) represented by SEQ ID NO: 2, SEQ ID NO: 12, SEQ ID NO: 22, SEQ ID NO: 32, SEQ ID NO: 42, SEQ ID NO: 52, SEQ ID NO: 62, or SEQ ID NO: 72 is prepared. Likewise, DNA encoding an amino acid sequence (VL) represented by SEQ ID NO: 4, SEQ ID NO: 14, SEQ ID NO: 24, SEQ ID NO: 34, SEQ ID NO: 44, SEQ ID NO: 54, SEQ ID NO: 64, or SEQ ID NO: 74 is prepared. Examples of such DNA include one represented by SEQ ID NO: 1, SEQ ID NO: 3, SEQ ID NO: 11, SEQ ID NO: 13, SEQ ID NO: 21, SEQ ID NO: 23, SEQ ID NO: 31, SEQ ID NO: 33, SEQ ID NO: 41, SEQ ID NO: 43, SEQ ID NO: 51, SEQ ID NO: 53, SEQ ID NO: 61, SEQ ID NO: 63, SEQ ID NO: 71, or SEQ ID NO: 73; however, those having other nucleotide sequences may be used. DNA may be prepared by known methods such as PCR. The DNA may be prepared by chemical synthesis.

The obtained DNA encoding VH or VL is inserted into a vector having a sequence encoding CH or CL of human antibody, to construct a chimeric antibody expression vector. The vector having a sequence encoding CH or CL of a human antibody is commercially available. By introducing the constructed expression vector into a host cell, a recombinant cell that expresses a chimeric antibody is obtained. Then the recombinant cell is cultured, and a desired chimeric antibody is acquired from the culture.

The host cell is not particular limited as far as the expression vector is able to function therein. The aforementioned animal cells (COS cell, CHO cell and the like), yeast, bacteria (*Escherichia coli* and the like), plant cells, insect cells and the like may be appropriately employed.

Next, a method for producing an antibody having a specific CDR including any one of the above (B1) to (B8) according to the third aspect will be described while taking production of a humanized antibody as an example. Here, the "humanized antibody" is an antibody having a CDR derived from an animal other than human, and other regions (framework region, constant region and the like) derived from human.

First, as DNAs encoding heavy chain CDRs 1-3 and light chain CDRs 1-3, DNAs encoding amino acid sequences represented by SEQ ID NOs: 5-10, SEQ ID NOs: 15-20, SEQ ID NOs: 25-30, SEQ ID NOs: 35-40, SEQ ID NOs: 45-50, SEQ ID NOs: 55-60, SEQ ID NOs: 65-70, or SEQ ID NOs: 75-80 are prepared. As the DNA, the sequence corresponding to each CDR in the nucleotide sequence represented by SEQ ID NO: 1, SEQ ID NO: 3, SEQ ID NO: 11, SEQ ID NO: 13, SEQ ID NO: 21, SEQ ID NO: 23, SEQ ID NO: 31, SEQ ID NO: 33, SEQ ID NO: 41, SEQ ID NO: 43, SEQ ID NO: 51, SEQ ID NO: 53, SEQ ID NO: 61, SEQ ID NO: 63, SEQ ID NO: 71, or SEQ ID NO: 73 is exemplified; however, those having other nucleotide sequences may be used. DNA may be prepared by known methods such as PCR. The DNA may be prepared by chemical synthesis.

Next, using these DNAs, DNA encoding a variable region in which heavy chain CDRs 1-3 are grafted to the framework region (FR) of VH in a certain human antibody is prepared. Likewise, DNA encoding a variable region in which light chain CDRs 1-3 are grafted to the FR of VL in a certain human antibody is prepared. The prepared DNA is inserted into a vector having a sequence encoding CH or CL of human antibody, to construct a humanized antibody expression vector. By introducing the constructed expression vector into a host cell, a recombinant cell that expresses a humanized antibody is obtained. Then the recombinant cell is cultured, and a desired humanized antibody is acquired from the culture.

Also an antibody having a specific CDR satisfying any one of the above (A1) to (A8) according to the second aspect may be produced in a similar procedure.

Also an anti-human CCR7 antibody having a heavy chain CDR3 containing an amino acid sequence represented by SEQ ID NO: 7, SEQ ID NO: 17, SEQ ID NO: 27, SEQ ID NO: 37, SEQ ID NO: 47, SEQ ID NO: 57, SEQ ID NO: 67, or SEQ ID NO: 77 according to the first aspect may be produced in a similar procedure.

A method for purifying the antibody of the present invention is not particularly limited, and known techniques may be employed. For example, a culture supernatant of the aforementioned hybridoma or the aforementioned recombinant cell may be collected, and the antibody of the present invention may be purified by a combination of known techniques such as various kinds of chromatography, salt precipitation, dialysis, membrane separation and the like. When the isotype of the antibody is IgG, the antibody may be conveniently purified by affinity chromatography using protein A.

Here, the hybridoma of the present invention is screened and acquired by using a known hybridoma preparation technique as will be described in detail in the later-described examples. Here, in immunizing an animal (for example, mouse) with an antigen, purified human CCR7 may be used as an antigen; however, a gene immunization technique may be used. In particular, by using a fusion gene in which a CCR7 gene is coupled with a gene of GroEL which is *Escherichia coli* chaperonin as an immunogen, preparation of the antibody may be facilitated. The detail of the gene immunization technique is described in WO 2006/041157.

The antibody of the present invention is useful as an active ingredient of a pharmaceutical composition (therapeutic agent). The pharmaceutical composition of the present invention includes the anti-human CCR7 antibody of the present invention and a pharmaceutically acceptable agent. Preferably, the pharmaceutical composition interferes with a CCR7-dependent intracellular signal transduction mechanism caused by a CCR7 ligand.

In a preferred embodiment, the pharmaceutical composition of the present invention is used for therapy of tissue fibrosis. An example of the tissue fibrosis includes fibrosis selected from the group consisting of hepatic fibrosis, renal fibrosis, pulmonary fibrosis, skin fibrosis, cardiovascular fibrosis, gastrointestinal fibrosis and other fibrous diseases.

An example of the hepatic fibrosis includes hepatic fibrosis selected from the group consisting of hepatic cirrhosis, ischemic reperfusion, post-hepatic transplant disorder, necrotic hepatitis, hepatitis B, hepatitis C, primary biliary cirrhosis, and primary sclerosing cholangitis. As to the hepatic cirrhosis, one caused by at least one selected from the group consisting of induction by alcohol, induction by a drug, and induction by chemical induction is recited. An example of the renal fibrosis includes renal fibrosis selected from the group consisting of proliferative glomerulonephritis, sclerotic glomerulonephritis, nephrogenic fibrosing dermopathy, diabetic nephropathy, renal tubule interstitial fibrosis, and focal segmental glomerulosclerosis. An example of the pulmonary fibrosis includes pulmonary fibrosis selected from the group consisting of pulmonary interstitial fibrosis, drug-induced sarcoidosis, pulmonary fibrosis, idiopathic pulmonary fibrosis, asthma, chronic obstructive pulmonary disease, diffuse pulmonary alveolar injury disease, pulmonary hypertension, and neonatal bronchopulmonary dysplasia.

An example of the skin fibrosis includes skin fibrosis selected from the group consisting of scleroderma, keloid scarring, psoriasis, hypertrophic scarring, and pseudo scleroderma. An example of the cardiovascular fibrosis includes cardiovascular fibrosis selected from the group consisting of atherosclerosis, coronary restenosis, congestive cardiomyopathy, heart failure, cardiac transplantation, and myocardial fibrosis. An example of the gastrointestinal fibrosis includes gastrointestinal fibrosis selected from the group consisting of collagenous colitis, villous atrophy, crypt hyperplasia, polyp formation, fibrosis of Crohn's disease, gastric ulcer healing, and post-abdominal adhesion surgery scar.

The fibrosis may have a condition arising from bone-related fibrosing disease and may be rheumatoid pannus formation.

The pharmaceutical composition of the present invention may be used for therapy of cancer metastasis. An example of the cancer includes cancer selected from the group consisting of pharyngeal cancer, chondrosarcoma, colon cancer, pancreatic cancer, leukemia, and breast cancer.

The pharmaceutical composition of the present invention may be administered systemically or topically, in an oral route or a parenteral route. As a dosage form, an injection form, a nasal dosage form, a pulmonary dosage form, a transdermal dosage form and the like are recited. In the case of an injection form, it may be systemically or topically administered, for example, by intravenous injection, intramuscular injection, intraperitoneal injection, subcutaneous injection or the like. The administration method may be appropriately selected depending on the age and the symptom of a patient. As a dose of the antibody of the present invention, for example, it may be selected within the range of 0.0001 mg to 1000 mg per 1 kg of body weight per one dosage. Alternatively, for example, the dose may be selected so that the amount of the antibody is within the range of 0.001 to 100000 mg/body per a patient. However, the dose of the antibody of the present invention is not limited to these ranges.

The pharmaceutical composition containing the antibody of the present invention may be formulated according to a routine procedure (for example, Remington's Pharmaceutical Science, latest edition, Mark Publishing Company, Easton, U.S.A). The pharmaceutical composition of the present invention contains a pharmaceutically acceptable agent or an additive. Examples of the agent or the additive include, but are not limited thereto, surfactants (e.g., PEG, TWEEN), excipients, antioxidants (e.g., ascorbic acid), coloring agents, flavoring agents, preservatives, stabilizers, buffers (e.g., phosphoric acid, citric acid, other organic acid), chelators (e.g., EDTA), suspending agents, tonicity agents, binders, disintegrating agents, lubricants, fluidic accelerating agents, and flavoring substances, and other commonly used carriers and the like may be appropriately used. Concrete examples thereof include light anhydrous silicic acid, lactose, crystalline cellulose, mannitol, starch, carmellose calcium, carmellose sodium, hydroxypropyl cellulose, hydroxypropylmethyl cellulose, polyvinylacetaldiethylamino acetate, polyvinylpyrrolidone, gelatin, medium-chain triglyceride, polyoxyethylene hardened castor oil 60, sucrose, carboxymethylcellulose, cornstarch, and inorganic salts. It may also contain other low molecular-weight polypeptides, proteins such as serum albumin, gelatin and immunoglobulin, and amino acid such as glycine, glutamine, asparagine, arginine and lysine.

Examples of an aqueous solution for injection include saline, an isotonic solution containing glucose or other adjuvants, for example, D-sorbitol, D-mannose, D-mannitol, and sodium chloride, and an appropriate solubilizing agent, for example, alcohol (e.g., ethanol), polyalcohol (e.g., propyleneglycol, PEG), a nonionic surfactant (polysorbate 80, HCO-50) or the like may be used together. The antibody of the present invention may be encapsulated in a microcapsule (e.g., microcapsule of hydroxymethyl cellulose, gelatin, poly(methyl methacrylate)), or formulated in a colloid drug delivery system (e.g., liposome, albumin microsphere, microemulsion, nanoparticle and nanocapsule) as is necessary (see "Remington's Pharmaceutical Science 16th edition", Oslo Ed. (1980) or the like).

Also, a technique for sustained-release of a drug is known, and such a technique is applicable to the pharmaceutical composition of the present invention (Langer et al., J. Biomed. Master. Res. 15:167-277 (1981); Langer, Chem. Tech. 12:98-105 (1982); U.S. Pat. No. 3,773,919; EP Patent Application Publication No. 58,481; Sidman et al., Biopolymers 22: 547-556 (1983); EP Patent Application Publication No. 133,988).

Further, there is known a technique for improving the therapeutic effect by directly fusing other drugs (e.g., anti-fibrotic agent, low molecular-weight anticancer agent, and cytokine) to the antibody, and such a technique is applicable to the pharmaceutical composition of the present invention.

It is also conceivable to incorporate a gene encoding the antibody of the present invention into a vector for a gene therapy, to prepare a gene therapeutic agent. As an administration method of the gene therapeutic agent (recombinant vector), besides direct administration by a naked plasmid, a method of packaging it in liposome or the like for administration, a method of incorporating it into various viral vectors such as retroviral vector, adenoviral vector, vaccinia virus vector, poxvirus vector, adeno-associated virus vector, or HVJ vector for administration (see Adolph "Viral Genomic Methods", CRC Press, Florid (1996)), and a method of coating a bead carrier such as a colloidal gold particle (WO 93/17706) with the agent for administration and the like are recited. That is, the gene therapeutic agent may be administered in any method as far as the antibody of the present invention is expressed in a living body, and is able to exert its action. Preferably, a sufficient amount is administered by appropriate parenteral routes (injection or infusion via intravenous, intraperitoneal, subcutaneous, intradermal, intra-adipose tissue, intra-mammary gland tissue, inhalation or intramuscular route, or a gas-induced particle bombardment method (by an electron gun or the like), a method via a mucosal route such as a nasal formulation, and the like). Further, the gene therapeutic agent may be administered to an animal by giving it to a cell by ex vivo liposome transfection, a particle bombardment method (U.S. Pat. No. 4,945,050), or by viral infection, and reintroducing the cell into the animal.

Also, the present invention includes a therapeutic method and a therapeutic agent for a disease or illness of a mammalian suffering from the disease or illness developed by an abnormal increase in CCR7 signal.

Here, the "therapy" means inhibiting or alleviating progression and aggravation of condition of a disease in an mammal that is susceptible to be or has been suffering from the disease, and is used in the meaning of a therapeutic treatment that is intended to inhibit or alleviate the progression and aggravation of symptoms and the like of the disease.

Further, the "disease" means a general disease developing due to an abnormal increase in CCR7 signal, and is the concept including, but is not limited to, hepatic fibrosis, renal fibrosis, pulmonary fibrosis, skin fibrosis, cardiovascular fibrosis, gastrointestinal fibrosis and other fibrous diseases, for example. It is also the concept including cancer metastasis from pharyngeal cancer, chondrosarcoma, colon cancer, pancreatic cancer, leukemia, or breast cancer as primary cancer. The "mammal" which is an objective of therapy means any animal classified into mammalia, and examples thereof include, but are not limited to, companion animals such as dog, cat and rabbit, and domestic animals such as cattle, pig, sheep and horse, besides human. A particularly preferred "mammal" is human.

The antibody-immobilized carrier of the present invention includes the anti-human CCR7 antibody of the present invention immobilized to a carrier. In a preferred embodiment, the antibody-immobilized carrier of the present invention is used for removing CCR7 expressing cells from a bodily fluid by contact with blood containing the CCR7-expressing cells. The anti-human CCR7 antibody immobilized to the carrier may be one or two or more kinds.

Examples of a concrete form of the antibody-immobilized carrier of the present invention include forms in which a water-insoluble carrier to which the antibody of the present invention is immobilized and packed in a container. Here, as the water-insoluble carrier, any material may be used, and those preferred from the viewpoints of moldability, sterilizability and low cell toxicity are synthetic polymers such as polyethylene, polypropylene, polystyrene, acrylic resin, nylon, polyester, polycarbonate, polyacrylamide and polyurethane, natural polymers such as agarose, cellulose, cellulose acetate, chitin, chitosan and alginate, inorganic materials such as hydroxyapatite, glass, alumina and titania, and metal materials such as stainless-steel and titanium.

As a form of the carrier, while a granular form, a cotton form, woven fabric, nonwoven fabric, a sponge-like porous body, a sheet-like form and the like are recited. From the viewpoint of large surface area per volume, a granular form, a cotton form, woven fabric, nonwoven fabric, and a sponge-like porous body are preferred. For example, peripheral blood may be passed through a porous filter in which a water-insoluble carrier to which the antibody is immobilized is packed in advance in a container, and thus the CCR7 expressing cells related with the disease can be efficiently removed.

A kit for removing CCR7 expressing cells may be fabricated by combining the antibody-immobilized carrier of the present invention and other constituents. As the other constituent, an anticoagulant agent, an extracorporeal circulation circuit and the like are recited.

The present invention embraces anti-human CCR7 antibodies of the following (1) to (5).

(1) An anti-human CCR7 antibody specifically binding to an extracellular domain of human CCR7, including a heavy chain complementarity determining region 3 (heavy chain CDR3) containing an amino acid sequence represented by SEQ ID NO: 7, SEQ ID NO: 17, SEQ ID NO: 27, SEQ ID NO: 37, SEQ ID NO: 47, SEQ ID NO: 57, SEQ ID NO: 67, or SEQ ID NO: 77.

(2) The anti-human CCR7 antibody according to the above (1), wherein the antibody includes complementarity determining regions 1 to 3 (CDRs 1-3) that consist of any one of amino acid sequences as the following (A1) to (A8):

(A1) having a heavy chain CDR1 containing an amino acid sequence represented by SEQ ID NO: 5, a heavy chain CDR2 containing an amino acid sequence represented by SEQ ID NO: 6, and a heavy chain CDR3 containing an amino acid sequence represented by SEQ ID NO: 7, (A2) having a heavy chain CDR1 containing an amino acid sequence represented by SEQ ID NO: 15, a heavy chain CDR2 containing an amino acid sequence represented by SEQ ID NO: 16, and a heavy chain CDR3 containing an amino acid sequence represented by SEQ ID NO: 17, (A3) having a heavy chain CDR1 containing an amino acid sequence represented by SEQ ID NO: 25, a heavy chain CDR2 containing an amino acid sequence represented by SEQ ID NO: 26, and a heavy chain CDR3 containing an amino acid sequence represented by SEQ ID NO: 27, (A4) having a heavy chain CDR1 containing an amino acid sequence represented by SEQ ID NO: 35, a heavy chain CDR2 containing an amino acid sequence represented by SEQ ID NO: 36, and a heavy chain CDR3 containing an amino acid sequence represented by SEQ ID NO: 37, (A5) having a heavy chain CDR1 containing an amino acid sequence represented by SEQ ID NO: 45, a heavy chain CDR2 containing an amino acid sequence represented by SEQ ID NO: 46, and a heavy chain CDR3 containing an amino acid sequence represented by SEQ ID NO: 47, (A6) having a heavy chain CDR1 containing an amino acid sequence represented by SEQ ID NO: 55, a heavy chain CDR2 containing an amino acid sequence represented by SEQ ID NO: 56, and a heavy chain CDR3 containing an amino acid sequence represented by SEQ ID NO: 57, (A7) having a heavy chain CDR1 containing an amino acid sequence represented by SEQ ID NO: 65, a heavy chain CDR2 containing an amino acid sequence represented by SEQ ID NO: 66, and a heavy chain CDR3 containing an amino acid sequence represented by SEQ ID NO: 67, and (A8) having a heavy chain CDR1 containing an amino acid sequence represented by SEQ ID NO: 75, a heavy chain CDR2 containing an amino acid sequence represented by SEQ ID NO: 76, and a heavy chain CDR3 containing an amino acid sequence represented by SEQ ID NO: 77.

(3) The anti-human CCR7 antibody according to the above (1) or (2), wherein the antibody includes complementarity determining regions 1 to 3 (CDRs 1-3) that consist of any one of amino acid sequences as the following (B1) to (B8):

(B1) having a heavy chain CDR1 containing an amino acid sequence represented by SEQ ID NO: 5, a heavy chain CDR2 containing an amino acid sequence represented by SEQ ID NO: 6, a heavy chain CDR3 containing an amino acid sequence represented by SEQ ID NO: 7, a light chain CDR1 containing an amino acid sequence represented by SEQ ID NO: 8, a light chain CDR2 containing an amino acid sequence represented by SEQ ID NO: 9, and a light chain CDR3 containing an amino acid sequence represented by SEQ ID NO: 10, (B2) having a heavy chain CDR1 containing an amino acid sequence represented by SEQ ID NO: 15, a heavy chain CDR2 containing an amino acid sequence represented by SEQ ID NO: 16, a heavy chain CDR3 containing an amino acid sequence represented by SEQ ID NO: 17, a light chain CDR1 containing an amino acid sequence represented by SEQ ID NO: 18, a light chain CDR2 containing an amino acid sequence represented by SEQ ID NO: 19, and a light chain CDR3 containing an amino acid sequence represented by SEQ ID NO: 20, (B3) having a heavy chain CDR1 containing an amino acid sequence represented by SEQ ID NO: 25, a heavy chain CDR2 containing an amino acid sequence represented by SEQ ID NO: 26, a heavy chain CDR3 containing an amino acid sequence represented by SEQ ID NO: 27, a light chain CDR1 containing an amino acid sequence represented by SEQ ID NO: 28, a light chain CDR2 containing an amino acid sequence represented by SEQ ID NO: 29, and a light chain CDR3 containing an amino acid sequence represented by SEQ ID NO: 30, (B4) having a heavy chain CDR1 containing an amino acid sequence represented by SEQ ID NO: 35, a heavy chain CDR2 containing an amino acid sequence represented by SEQ ID NO: 36, a heavy chain CDR3 containing an amino acid sequence represented by SEQ ID NO: 37, a light chain CDR1 containing an amino acid sequence represented by SEQ ID NO: 38, a light chain CDR2 containing an amino acid sequence represented by SEQ ID NO: 39, and a light chain CDR3 containing an amino acid sequence represented by SEQ ID NO: 40, (B5) having a heavy chain CDR1 containing an amino acid sequence represented by SEQ ID NO: 45, a heavy chain CDR2 containing an amino acid sequence represented by SEQ ID NO: 46, a heavy chain CDR3 containing an amino acid sequence represented by SEQ ID NO: 47, a light chain CDR1 containing an amino acid sequence represented by SEQ ID NO: 48, a light chain CDR2 containing an amino acid sequence represented by SEQ ID NO: 49, and a light chain CDR3 containing an amino acid sequence represented by SEQ ID NO: 50, (B6) having a heavy chain CDR1 containing an amino acid sequence represented by SEQ ID NO: 55, a heavy chain CDR2 containing an amino acid sequence represented by SEQ ID NO: 56, a heavy chain CDR3 containing an amino acid sequence represented by SEQ ID NO: 57, a light chain CDR1 containing an amino acid sequence represented by SEQ ID NO: 58, a light chain CDR2 containing an amino acid sequence represented by SEQ ID NO: 59, and a light chain CDR3 containing an amino acid sequence represented by SEQ ID NO: 60, (B7) having a heavy chain CDR1 containing an amino acid sequence represented by SEQ ID NO: 65, a heavy chain CDR2 containing an amino acid sequence represented by SEQ ID NO: 66, a heavy chain CDR3 containing an amino acid sequence represented by SEQ ID NO: 67, a light chain CDR1 containing an amino acid sequence represented by SEQ ID NO: 68, a light chain CDR2 containing an amino acid sequence represented by SEQ ID NO: 69, and a light chain CDR3 containing an amino acid sequence represented by SEQ ID NO: 70, and (B8) having a heavy chain CDR1 containing an amino acid sequence represented by SEQ ID NO: 75, a heavy chain CDR2 containing an amino acid sequence represented by SEQ ID NO: 76, a heavy chain CDR3 containing an amino acid sequence represented by SEQ ID NO: 77, a light chain CDR1 containing an amino acid sequence represented by SEQ ID NO: 78, a light chain CDR2 containing an amino acid sequence represented by SEQ ID NO: 79, and a light chain CDR3 containing an amino acid sequence represented by SEQ ID NO: 80.

(4) The anti-human CCR7 antibody according to any one of the above (1) to (3), wherein the antibody includes a heavy chain variable region and a light chain variable region that consist of any one of amino acid sequences as the following (C1) to (C8):

(C1) having a heavy chain variable region containing an amino acid sequence represented by SEQ ID NO: 2, and a light chain variable region containing an amino acid sequence represented by SEQ ID NO: 4, (C2) having a heavy chain variable region containing an amino acid sequence represented by SEQ ID NO: 12, and a light chain variable region containing an amino acid sequence represented by SEQ ID NO: 14,
(C3) having a heavy chain variable region containing an amino acid sequence represented by SEQ ID NO: 22, and a light chain variable region containing an amino acid sequence represented by SEQ ID NO: 24,
(C4) having a heavy chain variable region containing an amino acid sequence represented by SEQ ID NO: 32, and a light chain variable region containing an amino acid sequence represented by SEQ ID NO: 34,
(C5) having a heavy chain variable region containing an amino acid sequence represented by SEQ ID NO: 42, and a light chain variable region containing an amino acid sequence represented by SEQ ID NO: 44,
(C6) having a heavy chain variable region containing an amino acid sequence represented by SEQ ID NO: 52, and a light chain variable region containing an amino acid sequence represented by SEQ ID NO: 54,
(C7) having a heavy chain variable region containing an amino acid sequence represented by SEQ ID NO: 62, and a light chain variable region containing an amino acid sequence represented by SEQ ID NO: 64, and
(C8) having a heavy chain variable region containing an amino acid sequence represented by SEQ ID NO: 72, and a light chain variable region containing an amino acid sequence represented by SEQ ID NO: 74.
(5) The anti-human CCR7 antibody according to any one of the above (1) to (4), which is produced by R7-01 (FERM BP-11369), R7-02 (FERN BP-11404), R7-05 (FERN BP-11371), R7-09 (FERN BP-11372), R7-11 (FERN BP-11373), R7-18 (FERN BP-11374), R7-25 (FERN BP-11375), or R7-47 (FERN BP-11376).

The present invention embraces a method for treating tissue fibrosis or metastasis of cancer by administering an effective amount of the anti-human CCR7 antibody. Concrete examples of the tissue fibrosis and the cancer are as described above.

The present invention embraces use of the anti-human CCR7 antibody for the manufacture of a medicament for the treatment of tissue fibrosis or metastasis of cancer. Also, the present invention embraces the anti-human CCR7 antibody for use in treating tissue fibrosis or metastasis of cancer. Concrete examples of the tissue fibrosis and the cancer are as described above.

Examples

In the following, the present invention will be described more concretely by way of examples; however, the present invention is not limited to these examples.

(1) Preparation of Human CCR7 (hCCR7) Gene

An artificially synthesized gene having a GCTAGC sequence added to 5' end of a human CCR7 gene sequence (NM_001838, SEQ ID NO: 81) registered to Genebank and a GTCGACTAGGAATTC sequence (SEQ ID NO: 83) added to 3' end of the same was prepared by a DNA synthesizer. The gene was introduced into a pUC57 cloning vector to prepare a human CCR7 gene clone. Hereinafter, a gene fragment prepared by cutting the obtained vector at NheI and SalI sites is called "DNA fragment A", and a gene fragment prepared by cutting at NheI and EcoRI sites is called "DNA fragment B".

(2) Isolation of GroEL Subunit Gene

Genomic DNA was extracted and purified from an *Escherichia coli* HMS174 (DE3) strain (Novagen). Then, PCR was conducted using the purified genomic DNA as a template and oligonucleotides having nucleotide sequences shown in SEQ ID NOs: 84 and 85 as a primer set, to amplify a DNA fragment containing a GroEL subunit gene having a nucleotide sequence shown in SEQ ID NO: 86 (hereinafter, called "DNA fragment C"). Originating from the primers, an SalI site was introduced at 5' end, and a sequence encoding two stop codons (TAATAG) and an NotI site were introduced at 3' end in the DNA fragment C.

(3) Construction of Gene Immunization Vector Expressing Fusion Protein of Human CCR7 and GroEL Subunit.

A mammalian expression vector pCI Mammalian Expression Vector (Promega) was digested with restriction enzymes NheI and SalI, and subjected to a terminal dephosphorylation treatment by bacterial alkaline phosphatase (BAP). Then, the DNA fragment A prepared in the above (1) was inserted into the vector. Further, this expression vector was digested with SalI and NotI, and subjected to a terminal dephosphorylation treatment by BAP. Then, the DNA fragment C prepared in the above (2) was inserted into the vector to construct vector pCI-hCCR7.GroEL. That is, vector pCI-hCCR7.GroEL has a fusion gene of a gene encoding human CCR7 and a gene encoding GroEL subunit.

(4) Preparation of Human CCR7 Gene-Introduced Stable Expression Cell

The DNA fragment B prepared in the above (1) was introduced into the NheI-EcoRI site of pCIneo (Promega) to construct pCIneo-hCCR7.

A lipofectamin solution (37.5 μL), an OPTI-MEMI culture medium (625 μL), and an OPTI-MEMI culture medium containing 20 μg of pCIneo-hCCR7 (625 μL) were mixed. Using this mixture, pCIneo-hCCR7 was introduced into $2\times10^3$ cells of CHO-K1 cells (Dainippon Pharmaceutical Co., Ltd.). As a control, only pCIneo was introduced into CHO-K1 cells. CHO-K1 cells into which a gene was introduced were cultured in a Ham's F12K+10% FBS culture medium (ICN) for 30 hours. Further, the cells were separated and suspended, and $5\times10^3$ cells were cultured on a 100 mm dish. The cells were subjected to a drug treatment in a Ham's F12K+10% FBS culture medium containing antibiotic G418 (Promega) in a concentration of 0.8 mg/mL for two weeks. After the drug treatment, G418 resistant cells were cloned by a limiting dilution method. Further, for increasing the Ca signal response, pCEP-Gα16 (Molecular Devices) was introduced into the cloned cells. A drug treatment was conducted in a similar manner in the presence of antibiotic hygromycin in a concentration of 0.2 mg/mL, and then cloning of hygromycin resistant cells were further conducted. Through these operations, a human CCR7 gene-introduced stable expression cell was prepared. Then, for confirming the CCR7 function activity in the cells, the following evaluation was conducted. The cells were cultured all day and night in an initial cell concentration of $2\times10^4$ cells/100 μL in a 96-well microtiter plate. After completion of the culture, each cell was stimulated with CCL21 (R&D systems) in a concentration ranging from $10^{-6}$ to $10^{-12}$ M. As a result, a transient increase in intracellular $Ca^{2+}$ concentration was observed. The $Ca^{2+}$ concentration was measured by using a $Ca^{2+}$ signal analyzer (FLIPR; Molecular Devices) and an intracellular $Ca^{2+}$ staining kit (Ca3 kit; Molecular Devices). From this result, it was found that active human CCR7 was normally and stably expressed on the CHO-K1 cell membrane.

(5) Gene Immunization

Vector pCI-hCCR7.GroEL was dissolved in saline in a concentration of 250 μg/mL to prepare an immunizing composition. Eight-week old mice BALB/c (male) were immunized by injection of each 0.12 mL of this immunizing composition to femoral muscle of both legs (at day 0). As a result, each 30 µg of pCI-hCCR7.GroEL was administered into both legs, namely, 60 µg per one dose per one animal was administered. The animal was then immunized repeatedly in a similar manner on day 7, day 21, and day 28. Then blood was sampled on day 0, day 7, day 14, day 21, day 28, day 35, and day 42 to prepare sera. As a control, a mouse was immunized with vector pCI-hCCR7 that expresses human CCR7 singly.

(6) Evaluation of Binding of Antibody to Active Human CCR7 in Serum by Flow Cytometry CHO-K1 cells in which introduction and stable expression of pCIneo-hCCR7 were confirmed (hereinafter, referred to as "hCCR7 gene-introduced cell") and CHO-K1 cells (control cell) into which pCIneo was introduced were washed with PBS. The serum on day 56 after immunization was diluted 500 folds, and incubated with the respective cells. Further, the respective cells were washed with PBS, and added with a phycoerythrin-labeled anti-mouse IgG antibody (Beckman Coulter) as a secondary antibody. Then interactions between each of the respective cells and the anti-human CCR7 antibody in the serum were analyzed by using a flow cytometer FACScalibur (Becton, Dickinson).

As a result, phycoerythrin was little detected in the serum before gene immunization when hCCR7 gene-introduced cells were used, but was detected in the serum after gene immunization. This revealed that the anti-human CCR7 antibody in the serum after immunization bound to the hCCR7 gene-introduced cells. In contrast, also when the control cells were used, phycoerythrin was not detected even in the serum after gene immunization. This revealed that the anti-human CCR7 antibody in the serum after immunization did not bind to the control cells.

From the above, it was possible to induce production of antibodies that specifically recognize an active human CCR7 extracellular domain in mouse serum by gene immunization with vector pCI-hCCR7.GroEL.

(7) Preparation of Anti-Human CCR7 Monoclonal Antibodies

Six mice that were gene-immunized in the same procedure as in the above (5) were boostered. The spleen was extirpated after three days from the booster immunization to prepare spleen cells. The spleen cells ($1 \times 10^8$ cells) and BALB/C mouse-derived HAT-selective myeloma SP2/0 cells ($1 \times 10^7$ cells) were fused by a PEG method (cell fusion). The population of the fused cells (hybridoma) was suspended in a RPMI culture medium, and then cultured in each well of fourteen 96-well micro plates. In this stage, about 990 kinds of hybridomas were obtained.

For two weeks from the next day of the cell fusion, the culture medium in the micro plate was replaced with a RPMI culture medium added with HAT Media Supplement (50×) (Sigma, Item number: H0262) once every three days.

An antibody binding evaluation was conducted in a similar manner as in the above (6) by flow cytometry to examine binding between the hCCR7 gene-introduced cells and the antibody in the hybridoma culture supernatant in each well. As a result, binding with antibody was observed in eight wells.

For eight kinds of hybridomas for which binding with antibody was observed, cloning by a limiting dilution method was conducted. That is, eight of hybridomas were cultured into a 96-well micro plate so that equal or less than one cell is contained in one well, and cultured. After two weeks, flow cytometry was conducted similarly to examine binding of the cloned antibody (anti-human CCR7 monoclonal antibody) in the culture supernatant. As a result, eight lines of hybridomas that produce anti-human CCR7 monoclonal antibody were cloned.

For each hybridoma, flask cultivation was conducted in 100 mL of a RPMI culture medium for two weeks. Each culture supernatant was purified and concentrated through a protein G column (Amersham Bioscience). About 20 mg each of the purified eight kinds of anti-human CCR7 monoclonal antibodies were obtained.

Each hybridoma was deposited to IPOD. Indication and Accession number of each hybridoma are as described above.

For each anti-human CCR7 monoclonal antibody (hereinafter, simply referred to as "anti-human CCR7 antibody"), the following test was conducted. In the following description, indication of hybridoma is also used as a name of an antibody.

(8) Evaluation of Binding to hCCR7 Gene-Introduced Cell by Flow Cytometry

Figure 10:
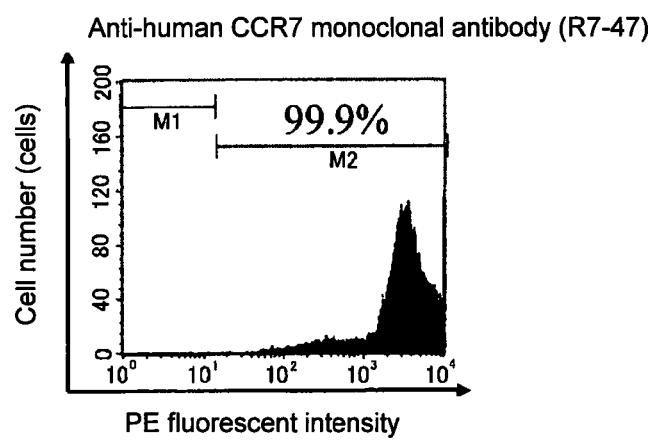
FIG. 10 A histogram showing an analytical result of interaction between human CCR7 gene-introduced cells and anti-human CCR7 antibody R7-47.

A 10 µg/mL solution of an anti-human CCR7 monoclonal antibody or mouse control IgG (Thermo, negative control) in PBS was prepared (hereinafter, referred to as "antibody solution"). After washing hCCR7 gene-introduced cells with PBS, the antibody solution was incubated together with the cells. Further, the cells were washed with PBS, and added with a phycoerythrin-labeled anti-mouse IgG antibody (Beckman Coulter) as a secondary antibody. Then interaction between the cells, and the anti-human CCR7 antibody or the mouse control IgG was analyzed by using a flow cytometer FACScalibur (Becton, Dickinson). The results are shown in FIGS. 9 and 10 and Table 2. FIG. 9 is a histogram showing an analytical result of interaction between hCCR7 gene-introduced cells, and mouse control IgG. FIG. 10 is a histogram showing an analytical result of interaction between a hCCR7 gene-introduced cell, and anti-human CCR7 antibody R7-47. Table 2 shows percentages of specifically binding cells calculated from analytical results of interaction between hCCR7 gene-introduced cells and respective anti-human CCR7 antibodies. In FIGS. 9 and 10, the vertical axis represents the number of cells, and the horizontal axis represents fluorescence intensity originating from phycoerythrin (PE). Of the two areas (M1, M2), the cell belonging to M2 (right area) indicates the cells that binds to the antibody. In Table 2, a percentage of specifically binding cells is represented by M2/(M1+M2).

As a result, when hCCR7 gene-introduced cells were used, a large number of cells were detected in the area of M2 (FIG. 10, Table 2). This demonstrated that each anti-human CCR7 antibody bound to the hCCR7 gene-introduced cells. In contrast, when mouse control IgG was used (FIG. 9), little cells were detected in the area of M2. This demonstrated that mouse control IgG failed to bind to the hCCR7 gene-introduced cells. From the foregoing, it was demonstrated that any of the obtained anti-human CCR7 antibodies specifically recognized an extracellular domain of active human CCR7.

TABLE 2

| Name of antibody | Percentage of specifically binding cells (M2/(M1 + M2)) |
|---|---|
| Control IgG | 0.7% |
| R7-01 | 99.8% |
| R7-02 | 100% |
| R7-05 | 100% |
| R7-09 | 100% |
| R7-11 | 100% |

TABLE 2-continued

| Name of antibody | Percentage of specifically binding cells M2/(M1 + M2) |
|---|---|
| R7-18 | 100% |
| R7-25 | 100% |
| R7-47 | 99.9% |

Figure 11:
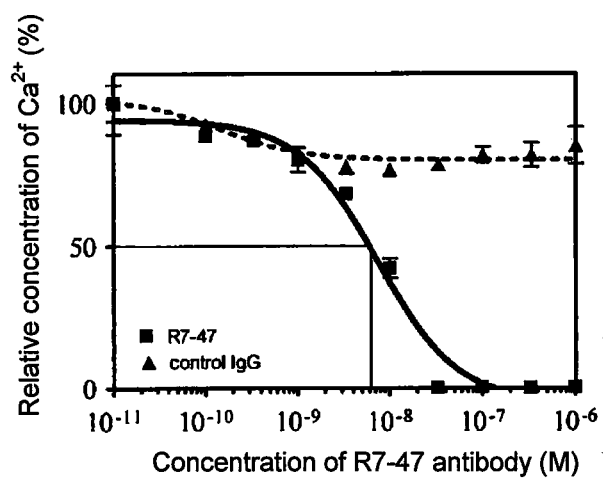
FIG. 11 A graph showing the relationship between an intracellular $Ca^{2+}$ concentration and a concentration of each additive.

(9) Evaluation of Intracellular $Ca^{2+}$ Signal Transduction Inhibiting Activity Human CCR7 gene-introduced cells were cultured all day and night in a 96-well micro titer plate at an initial cell concentration of $2\times10^4$ cells/100 μL. After completion of culture, each well was added with an anti-human CCR7 antibody in a concentration ranging from $10^{-6}$ to $10^{-11}$ M. As a control, a sample added similarly with mouse control IgG (Thermo, negative control) in a concentration ranging from $10^{-6}$ to $10^{-11}$ M was prepared. After one hour, the degree of an antibody concentration-dependent reduction in transient elevation of intracellular $Ca^{2+}$ concentration when the cells were stimulated by $1\times10^{-7}$ M CCL21 (R&D systems) was determined. The $Ca^{2+}$ concentration was determined by using a $Ca^{2+}$ signal analyzer (FLIPR; Molecular Devices) and an intracellular Ca staining kit (Ca3kit; Molecular Devices). The result when anti-human CCR7 antibody R7-47 was added is shown in FIG. 11. FIG. 11 is a graph showing the relation between an intracellular $Ca^{2+}$ concentration and a concentration of each of additives. As shown in FIG. 11, a decrease in intracellular $Ca^{2+}$ concentration that was dependent on a concentration of R7-47 was observed. This demonstrated that intracellular signal transduction was inhibited with a result that R7-47 competitively inhibits binding between CCL21 and human CCR7. 50% inhibition concentration (IC50) was calculated to be 7.4 nM for R7-47. Table 3 shows IC50 of anti-human CCR7 antibodies other than R7-47.

From these results, it was demonstrated that any of the obtained anti-human CCR7 antibodies was able to interfere with a CCR7-dependent intracellular signal transduction mechanism caused by a human CCR7 ligand.

TABLE 3

| Name of antibody | 50% inhibition concentration (IC50) |
|---|---|
| R7-01 | 340 nM |
| R7-02 | 46 nM |
| R7-05 | 94 nM |
| R7-09 | 32 nM |
| R7-11 | 16 nM |
| R7-18 | 11 nM |
| R7-25 | 22 nM |
| R7-47 | 7.4 nM |

(10) Isotype Analysis

Isotype of an anti-human CCR7 antibody was determined using a mouse monoclonal antibody isotyping kit (GE Healthcare). Detection was conducted by sandwich ELISA using a horseradish peroxidase-labeled mouse IgG antibody. The result is shown in Table 4.

TABLE 4

| Name of antibody | Immunoglobulin isotype |
|---|---|
| R7-01 | IgG1 κ |
| R7-02 | IgG2a λ |
| R7-05 | IgG2b λ |
| R7-09 | IgG2a λ |

TABLE 4-continued

| Name of antibody | Immunoglobulin isotype |
|---|---|
| R7-11 | IgG1 κ |
| R7-18 | IgG1 κ |
| R7-25 | IgG1 κ |
| R7-47 | IgG1 κ |

(11) cDNA Cloning of Antibody Variable Regions, and Determination of Complementarity Determining Regions (CDRs)

From the foregoing eight kinds of hybridomas, DNAs that encode variable regions of L chain and H chain of each antibody were cloned, and nucleotide sequences thereof were determined. Cloning was conducted in the following manner. First, RNA was isolated from the hybridoma by using RNEASYMINI Kit (QIAGEN). Then cDNA synthesis by a 5'-RACE method was conducted using "SMARTER-RACE CDNA AMPLIFICATION KIT" (TAKARA BIO) according to the manufacture's manual, and a PCR product was obtained. As a 3' side primer for PCR, the sequence of SEQ ID NO: 87 was used for the γ chain, the sequences of SEQ ID NOs: 88-90 were used for the κ chain, and the sequence of SEQ ID NO: 91 was used for the λ chain.

The obtained DNA fragment was inserted into pT7 BLUET VECTOR (Novagen) by using DNA Ligation kit ver. 2 (TAKARA BIO). XL10GOLD (Stratagene) was transformed by this vector. After inoculation on a plate containing X-gal, ampicillin, and IPTG, white colonies were picked up. After preparing plasmids from respectively five clones containing a normal size insert, the DNA sequences were determined by using an ABI PRISM 3130 type automatic sequencer. Since three clones showed the same sequence except that mutation possibly due to PCR error was observed in part of the determined sequences, the sequences were determined as the objective DNA sequences. The obtained nucleotide sequences and amino acid sequences corresponding thereto are shown in SEQ ID NO: 1 (VH of R7-01), SEQ ID NO: 3 (VL of R7-01), SEQ ID NO: 11 (VH of R7-02), SEQ ID NO: 13 (VL of R7-02), SEQ ID NO: 21 (VH of R7-05), SEQ ID NO: 23 (VL of R7-05), SEQ ID NO: 31 (VH of R7-09), SEQ ID NO: 33 (VL of R7-09), SEQ ID NOs: 41 (VH of R7-11) and 43 (VL of R7-11), SEQ ID NO: 51 (VH of R7-18), SEQ ID NO: 53 (VL of R7-18), SEQ ID NO: 61 (VH of R7-25), SEQ ID NO: 63 (VL of R7-25), SEQ ID NO: 71 (VH of R7-47), and SEQ ID NO: 73 (VL of R7-47).

Only amino acid sequences corresponding to respective nucleotide sequences are shown in SEQ ID NO: 2 (VH of R7-01), SEQ ID NO: 4 (VL of R7-01), SEQ ID NO: 12 (VH of R7-02), SEQ ID NO: 14 (VL of R7-02), SEQ ID NO: 22 (VH of R7-05), SEQ ID NO: 24 (VL of R7-05), SEQ ID NO: 32 (VH of R7-09), SEQ ID NO: 34 (VL of R7-09), SEQ ID NOs: 42 (VH of R7-11) and 44 (VL of R7-11), SEQ ID NO: 52 (VH of R7-18), SEQ ID NO: 54 (VL of R7-18), SEQ ID NO: 62 (VH of R7-25), SEQ ID NO: 64 (VL of R7-25), SEQ ID NO: 72 (VH of R7-47), and SEQ ID NO: 74 (VL of R7-47).

For each of VH and VL, CDRs 1-3 (SEQ ID NOs: 5-10, 15-20, 25-30, 35-40, 45-50, 55-60, 65-70, 75-80) were identified. See FIGS. 1 to 9 and Table 1.

(12) Confirmation of Binding of Anti-Human CCR7 Antibody Using Human Primary Culture Cells From peripheral blood of a healthy person, mononuclear cells (PBMC) were isolated using LYMPHOPREP (Axis-Shield) according to a routine method. The isolated PBMC were suspended in a phosphate buffered saline (PBS) solution containing 1 mg/mL human gamma-globulin (Jackson Immuno Research Laboratories), and blocked by incubation at room temperature for 30 minutes. The PBMC ($3\times10^5$ cells) after blocking were incubated together with each anti-human CCR7 antibody (0.5 µg) or isotype control antibody (0.5 µg) at 4° C. for one hour. Thereafter, PBMC were washed three times with a washing buffer (PBS solution containing 0.1% fetal bovine serum). Then, a fluorescein isothiocyanate (FITC)-labeled anti-mouse IgG antibody (Beckman Coulter) was added as secondary antibody, and incubated at 4° C. for 1 hour. PBMC were washed again three times with the washing buffer, and then analyzed by using a flow cytometer (Beckman Coulter).

Figure 12:
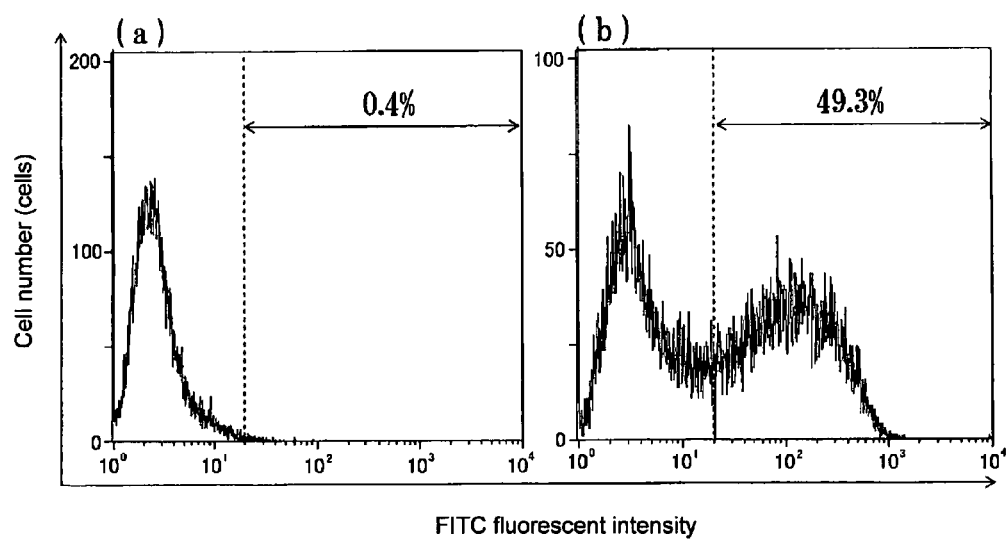
FIG. 12 (a) is a histogram showing the result of staining with an isotype control antibody and an FITC-labeled anti-mouse IgG antibody, and (b) is a histogram showing the result of staining with R7-47 and an FITC-labeled anti-mouse IgG antibody.

A result of flow cytometry when R7-47 is used is shown in FIG. 12. FIG. 12 (a) shows a result when staining is conducted by isotype control antibody and FITC-labeled anti-mouse IgG antibody. FIG. 12 (b) shows a result when staining is conducted by R7-47 and FITC-labeled anti-mouse IgG antibody. The part indicated by the double-headed arrow in FIG. 12 (a) and FIG. 12 (b) represents a cell population to which an isotype control antibody and R7-47 specifically bind, respectively. The number in the drawing represents a percentage of the cell population with respect to 100% of the cell number of analyzed PBMC.

A percentage of cells to which each anti-human CCR7 antibody specifically binds in PBMC is shown in Table 5.

TABLE 5

| Name of antibody | Percentage of specifically binding cells |
|---|---|
| R7-01 | 10.8% |
| R7-02 | 44.6% |
| R7-05 | 37.3% |
| R7-09 | 32.9% |
| R7-11 | 25.5% |
| R7-18 | 40.5% |
| R7-25 | 47.0% |
| R7-47 | 49.3% |

From these results, it was demonstrated that the anti-human CCR7 antibody recognized human native CCR7, and was able to bind to the human native CCR7.

(13) Confirmation of Functionality of Anti-Human CCR7 Antibody Using Human Primary Culture Cells PBMC ($1.6\times10^5$ cells) were cultured in an insert of a 24-well cell culture insert (Becton, Dickinson). Further, 10 µg/mL of each anti-human CCR7 antibody or isotype control IgG antibody was added, and allowed to react at room temperature for 5 minutes. Each well of the cell culture insert was added with human recombinant CCL21 (150 ng/mL). After placing the insert on a plate, the reaction was allowed at 37° C. for 1.5 hours. After the reaction, the insert was removed, and the number of cells migrated into each well was counted. Table 6 and Table 7 show the results of functional inhibition for CCL21-dependent cell migration by the antibody.

TABLE 6

| Added antibody | CCL21 addition | Number of migrated cells ($\times10^4$ cells/mL) |
|---|---|---|
| None | − | 50.7 ± 0.6 |
| None | + | 93.7 ± 11.4 |
| Isotype IgG1 | + | 91.2 ± 17.2 |
| R7-01 | + | 55.0 ± 5.6 |
| R7-11 | + | 49.7 ± 6.5 |

TABLE 6-continued

| Added antibody | CCL21 addition | Number of migrated cells ($\times10^4$ cells/mL) |
|---|---|---|
| R7-18 | + | 47.3 ± 10.7 |
| R7-25 | + | 56.3 ± 10.8 |
| R7-47 | + | 51.7 ± 2.3 |

(Mean value ± standard deviation)

TABLE 7

| Added antibody | CCL21 addition | Number of migrated cells ($\times10^4$ cells/mL) |
|---|---|---|
| None | − | 54.0 ± 12.2 |
| None | + | 98.7 ± 5.7 |
| Isotype IgG2 | + | 98.0 ± 3.0 |
| R7-02 | + | 59.0 ± 11.1 |
| R7-05 | + | 56.0 ± 1.0 |
| R7-09 | + | 60.3 ± 12.3 |

(Mean value ± standard deviation)

First, from the comparison between no addition of CCL21 and addition of CCL21, it was demonstrated that a part of cells of PBMC migrated CCL21-dependently. The addition of an isotype control (IgG1 or IgG2) antibody did not influence on the CCL21-dependent cell migration. In contrast, when the antibody was added, any of eight kinds of the antibodies significantly suppressed the CCL21-dependent cell migration. From these results, it was demonstrated that any of the anti-human CCR7 antibodies suppressed function of human native CCR7.

(14) Confirmation of Action of Anti-Human CCR7 Antibody of Inhibiting Tissue Fibrosis in Pulmonary Fibrosis Model A CD14 positive cells that express CCR7 in human PBMC are important cells for fibrosis in pulmonary fibrosis (Abe R, Donnelly S C, Peng T, Bucala R, Metz C N, "Peripheral blood fibrocytes: differentiation pathway and migration to wound sites." J Immunol. 2001 Jun. 15; 166 (12):7556-62; Curnow S J, Fairclough M, Schmutz C, Kissane S, Denniston A K, Nash K, Buckley C D, Lord J M, Salmon M, "Distinct types of fibrocyte can differentiate from mononuclear cells in the presence and absence of serum." PLoS One. 2010 Mar. 18; 5(3):e9730). Efficacy of an anti-human CCR7 antibody in pulmonary fibrosis can be elucidated by administering a stimulant that induces pulmonary fibrosis (for example, bleomycin) to an immunodeficient mouse (for example, SCID mouse), and examining migration of CD14-positive cells that express CCR7 derived from human into lung tissue when the cells are grafted.

PBMC were isolated from peripheral blood of a healthy person according to a routine method. The isolated PBMC were further brought into contact with human CD14-labeled magnetic beads (Miltenyi Biotec) to separate CD14-positive cells. The CD14-positive cells were used for cell grafting into a mouse. A T cell and B cell-deficient SCID mouse was administered transbronchially with bleomycin (Nippon Kayaku, product name: BLEO) dissolved in saline in an amount of 5 mg/kg to induce pulmonary fibrosis by a routine method. Based on day 0 on which bleomycin was administered, anti-human CCR7 antibody R7-11, R7-18, or R7-47 dissolved in saline was intraperitoneally administered in a dose of 20 mg/kg on four days prior to administration of bleomycin and on days 1, 4, 8 and 11 after administration of bleomycin. As a control, isotype control IgG was administered in a similar schedule. On day 4 after administration of bleomycin, human CD14-positive cells containing cells expressing CCR7 were isolated in the manner as described above, and fluorescence-labeled with a PKH26PCL red fluorescent cell linker kit (Sigma). The fluorescence-labeled cells were transferred in an amount of 1×10$^6$ cells per one mouse from tail vein. The mouse was autopsied after 15 days from administration of bleomycin. A lung tissue obtained was formalin-fixed according to a routine method to prepare pathological section. The pathological tissue was observed under a fluorescence microscope, and the number of cells derived from fluorescent labeled human cells was counted in the entire visual field of the right lung. As a result, in comparison with the mouse administered with isotype control IgG, the number of fluorescent labeled cells in the lung was reduced in any mouse administered with an anti-human CCR7 antibody.

Figure 13:
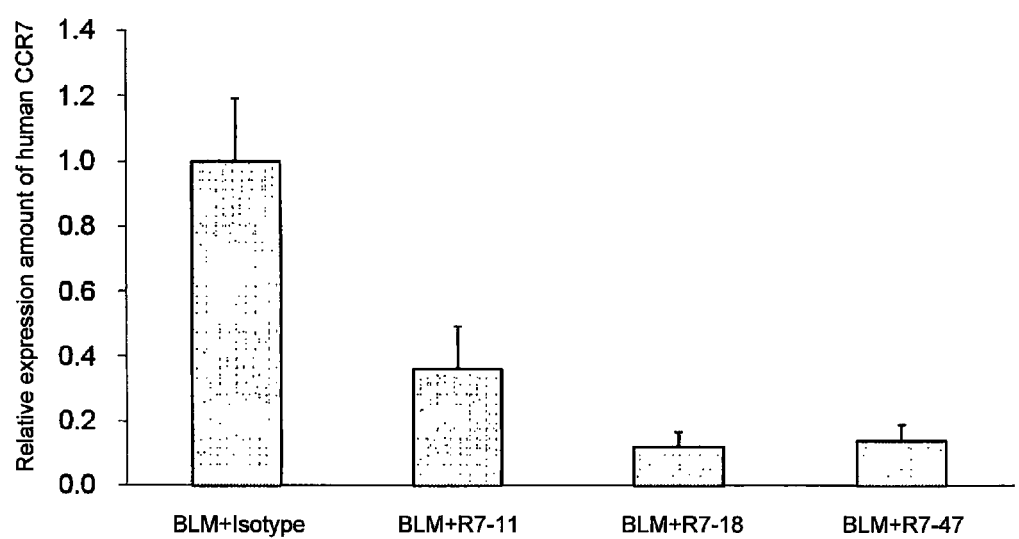
FIG. 13 A graph showing the result of an experiment in which a pulmonary fibrosis-induced mouse is administered with anti-human CCR7 antibody R7-11, R7-18, or R7-47.

From the left lung obtained by autopsy, total RNA of the tissue was extracted by a TRIZOL reagent (Invitrogen), and the extracted RNA was quantified by NANO DROP 1000 (Thermo Fisher Scientific). An RNA sample (2 µg) obtained from each mouse lung was subjected to reverse transcription using a High Capacity cDNA Reverse transcription kit (Applied Biosystems). For the obtained cDNA sample, an amount of mRNA of human CCR7 in the lung tissue was measured by a real time PCR method. Analysis by real time PCR was conducted by TAQMAN Gene Expression Assays system (Applied Biosystems). TAQMAN Ribosomal RNA Control Reagents (Applied Biosystems) was used as an internal standard. A probe set of Hs01013469_m1 (Applied Biosystems) was used for detection of human CCR7. The obtained data was analyzed by the ΔΔCt method, and evaluated as a relative expression amount, with reference to the group administered with an isotype control. As a result, in comparison with the mouse administered with isotype control IgG, the amount of mRNA of human CCR7 was reduced in any mouse administered with anti-human CCR7 antibody R7-11, R7-18, or R7-47 (FIG. 13). This result reflected that the anti-human CCR7 antibody suppressed invasion of cells into the lung tissue that was important for fibrosis in pulmonary fibrosis. From these results, it was demonstrated that the anti-CCR7 antibody was useful for therapy of pulmonary fibrosis.

(15) Production of Anti-Human CCR7 Antibody by Gene Recombination Technique

A gene of the full-length of a heavy chain of a mouse antibody containing DNA represented by SEQ ID NO: 11 was cloned, and introduced into secretory expression vector pSecTag2 (Invitrogen). This vector was named pSecTag2-R702HC. Likewise, a gene of the full-length of a heavy chain of a mouse antibody containing DNA represented by SEQ ID NO: 41 was cloned, and introduced into secretory expression vector pSecTag2. This vector was named pSecTag2-R711HC. Likewise, a gene of the entire length of a heavy chain of a mouse antibody containing DNA represented by SEQ ID NO: 51 was cloned, and introduced into secretory expression vector pSecTag2. This vector was named pSecTag2-R718HC.

A gene of the full-length of a light chain of a mouse antibody containing DNA represented by SEQ ID NO: 13 was cloned, and introduced into secretory expression vector pSecTag2. This vector was named pSecTag2-R702LC. Likewise, a gene of the full-length of a light chain of a mouse antibody containing DNA represented by SEQ ID NO: 43 was cloned, and introduced into secretory expression vector pSecTag2. This vector was named pSecTag2-R711LC. Likewise, a gene of the full-length of a light chain of a mouse antibody containing DNA represented by SEQ ID NO: 53 was cloned, and introduced into secretory expression vector pSecTag2. This vector was named pSecTag2-R718LC.

pSecTag2-R702HC and pSecTag2-R702LC were introduced into HEK293 cells using LIPOFECTAMINE 2000 (Invitrogen). The cells were cultured for two days. The culture supernatant was subjected to a Protein-G column to prepare a recombinant anti-human CCR7 antibody derived from hybridoma R7-02. Likewise, pSecTag2-R711HC and pSecTag2-R711LC were introduced into HEK293 cells using LIPOFECTAMINE2000. The cells were cultured for two days. The culture supernatant was subjected to a Protein-G column to prepare a recombinant anti-human CCR7 antibody derived from hybridoma R7-11. Likewise, pSecTag2-R718HC and pSecTag2-R718LC were introduced into HEK293 cells using LIPOFECTAMINE2000. The cells were cultured for two days. The culture supernatant was subjected to a Protein-G column to prepare a recombinant anti-human CCR7 antibody derived from hybridoma R7-18.

Figure 14:
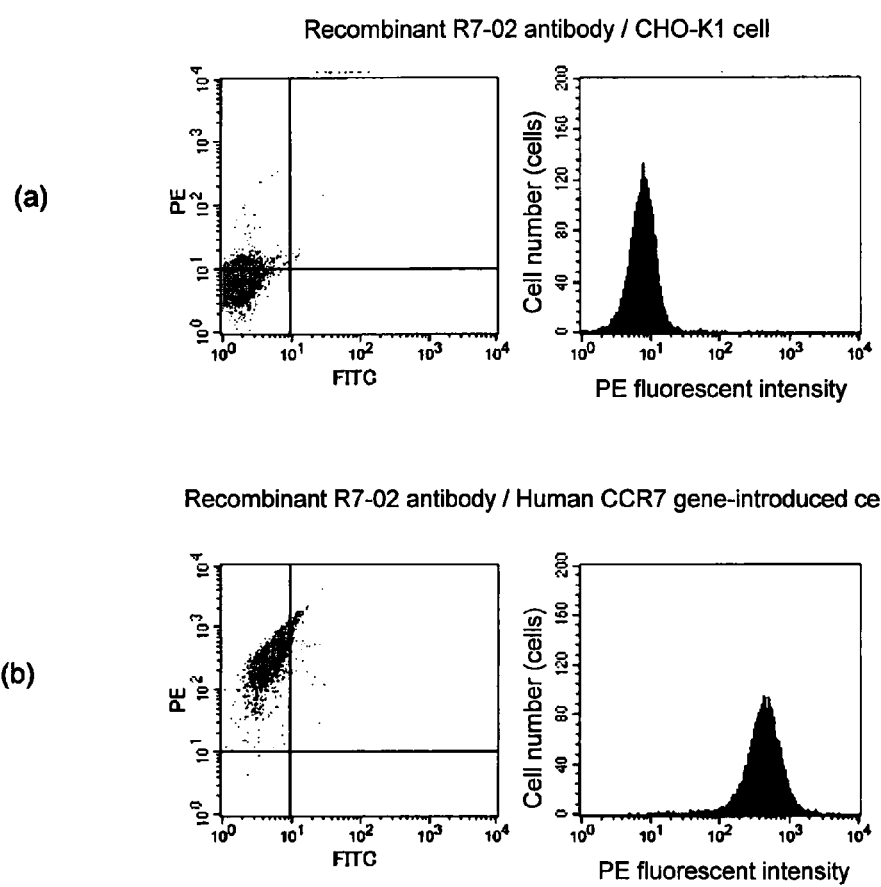
FIG. 14 (a) is a two-dimensional dot diagram and a histogram showing an analytical result of interaction between CHO-K1 cells and the recombinant anti-human CCR7 antibody derived from hybridoma R7-02, and (b) is a two-dimensional dot diagram and a histogram showing an analytical result of interaction between human CCR7 gene-introduced cells and the recombinant anti-human CCR7 antibody derived from hybridoma R7-02.
Figure 15:
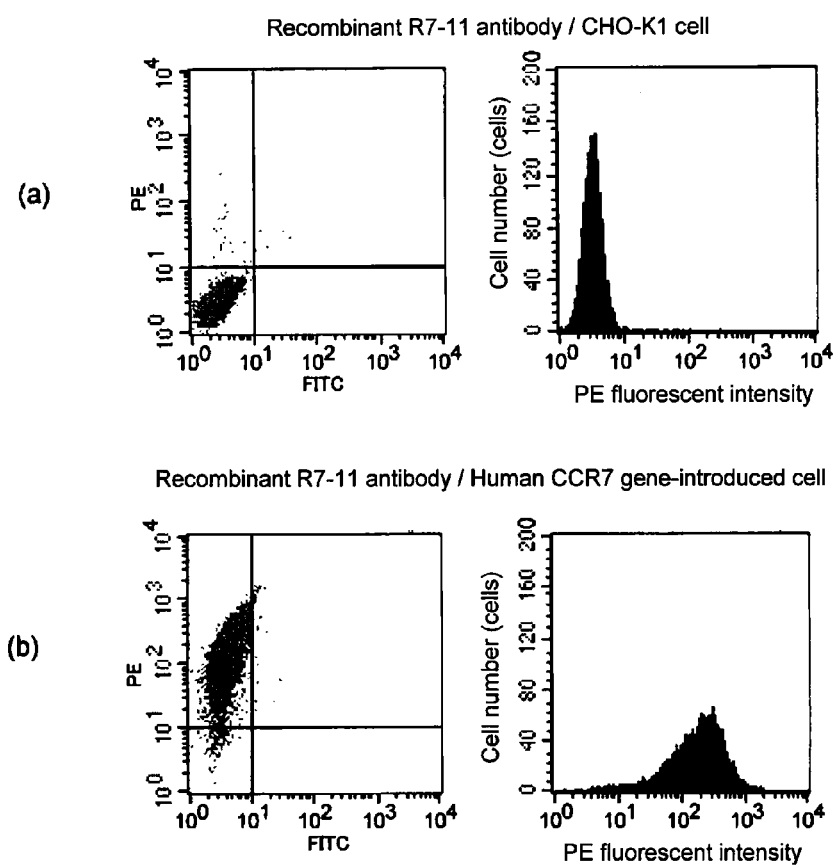
FIG. 15 (a) is a two-dimensional dot diagram and a histogram showing an analytical result of interaction between CHO-K1 cells and the recombinant anti-human CCR7 antibody derived from hybridoma R7-11, and (b) is a two-dimensional dot diagram and a histogram showing an analytical result of interaction between human CCR7 gene-introduced cells and the recombinant anti-human CCR7 antibody derived from hybridoma R7-11.
Figure 16:
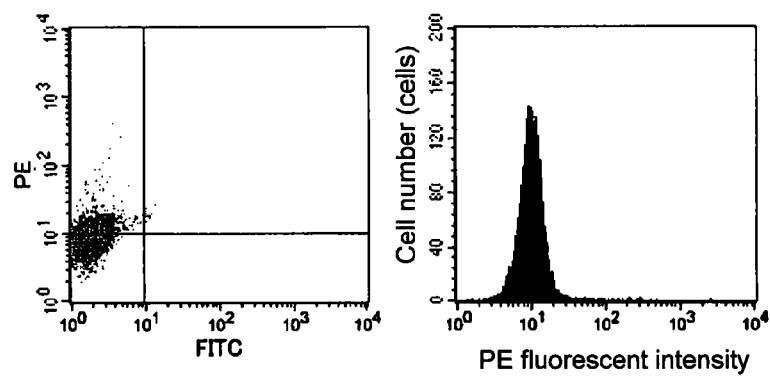
FIG. 16 (a) is a two-dimensional dot diagram and a histogram showing an analytical result of interaction between CHO-K1 cells and the recombinant anti-human CCR7 antibody derived from hybridoma R7-18, and (b) is a two-dimensional dot diagram and a histogram showing an analytical result of interaction between human CCR7 gene-introduced cells and the recombinant anti-human CCR7 antibody derived from hybridoma R7-18.
Figure 16:
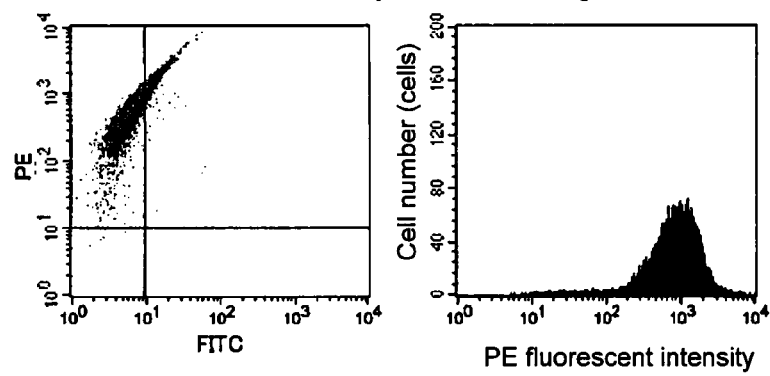

Similarly to the above (6), it was examined using a flow cytometer whether 10 µg/mL of each recombinant anti-human CCR7 antibody bound to hCCR7 gene-introduced cells and a CHO-K1 cells (negative control). Interaction between each cell and each recombinant anti-human CCR7 antibody was analyzed using a phycoerythrin-labeled anti-mouse IgG antibody (Beckman Coulter) as a fluorescent secondary antibody and FACSCALIBUR (Becton, Dickinson) as a flow cytometer. The results are shown in FIGS. 14 to 16. FIG. 14 shows a result using the recombinant anti-human CCR7 antibody derived from hybridoma R7-02. FIG. 15 shows a result using the recombinant anti-human CCR7 antibody derived from hybridoma R7-11. FIG. 16 shows a result using the recombinant anti-human CCR7 antibody derived from hybridoma R7-18. In FIGS. 14 to 16, (a) shows a two-dimensional dot chart (left) and a histogram (right) when the CHO-K1 cells were used, (b) shows a two-dimensional dot chart (left) and a histogram (right) when the hCCR7 gene-introduced cells were used. In each of the two-dimensional dot charts, the vertical axis represents fluorescent intensity originating from phycoerythrin (PE), and the horizontal axis represents fluorescent intensity originating from fluorescein isothiocyanate (FITC). That is, it was demonstrated that any recombinant anti-human CCR7 antibody bound to the hCCR7 gene-introduced cells, but not to the CHO-K1 cells. These results revealed that the antibody of the present invention was able to be produced in the forms of mouse-type antibody, chimeric antibody, humanized antibody, functional fragment of antibody and the like by using gene recombination techniques.

The invention claimed is:

1. A nucleic acid encoding a heavy chain variable region or a light chain variable region of an anti-human-CC-motif-receptor-7 (anti-human-CCR7) antibody capable of specifically binding to an extracellular domain of human CCR7,
the antibody being produced by a hybridoma FERM BP-11369, FERM BP-11404, FERM BP-11371, FERM BP-11372, FERM BP-11373, FERM BP-11374, FERM BP-11375, or FERM BP-11376, and
wherein the antibody is capable of interfering with a CCR7-dependent intracellular signal transduction mechanism caused by CCR7 ligand stimulation, without relying on complement-dependent cell lysis action or antibody-dependent cell-mediated cytotoxicity.

2. The nucleic acid according to claim 1, wherein the anti-human-CCR7 antibody is a humanized antibody or a chimeric antibody.

3. The nucleic acid according to claim 2, wherein the anti-human-CCR7 antibody is an antibody fragment, a single-chain antibody or a diabody.

4. A vector comprising the nucleic acid according to claim 1.

5. A cell into which the vector according to claim 4 has been introduced.

6. A nucleic acid encoding a heavy chain variable region or a light chain variable region of an anti-human-CC-motif-receptor-7 (anti-human-CCR7) antibody capable of specifically binding to an extracellular domain of human CCR7,
wherein the antibody comprises heavy chain complementarity determining regions 1 to 3 (heavy chain CDRs 1-3) and light chain complementarity determining regions 1 to 3 (light chain CDRs 1-3) of any one of the following (B1) to (B8):

(B1) comprising a heavy chain CDR1 containing an amino acid sequence represented by SEQ ID NO: 5, a heavy chain CDR2 containing an amino acid sequence represented by SEQ ID NO: 6, a heavy chain CDR3 containing an amino acid sequence represented by SEQ ID NO: 7, a light chain CDR1 containing an amino acid sequence represented by SEQ ID NO: 8, a light chain CDR2 containing an amino acid sequence represented by SEQ ID NO: 9, and a light chain CDR3 containing an amino acid sequence represented by SEQ ID NO: 10, (B2) comprising a heavy chain CDR1 containing an amino acid sequence represented by SEQ ID NO: 15, a heavy chain CDR2 containing an amino acid sequence represented by SEQ ID NO: 16, a heavy chain CDR3 containing an amino acid sequence represented by SEQ ID NO: 17, a light chain CDR1 containing an amino acid sequence represented by SEQ ID NO: 18, a light chain CDR2 containing an amino acid sequence represented by SEQ ID NO: 19, and a light chain CDR3 containing an amino acid sequence represented by SEQ ID NO: 20, (B3) comprising a heavy chain CDR1 containing an amino acid sequence represented by SEQ ID NO: 25, a heavy chain CDR2 containing an amino acid sequence represented by SEQ ID NO: 26, a heavy chain CDR3 containing an amino acid sequence represented by SEQ ID NO: 27, a light chain CDR1 containing an amino acid sequence represented by SEQ ID NO: 28, a light chain CDR2 containing an amino acid sequence represented by SEQ ID NO: 29, and a light chain CDR3 containing an amino acid sequence represented by SEQ ID NO: 30, (B4) comprising a heavy chain CDR1 containing an amino acid sequence represented by SEQ ID NO: 35, a heavy chain CDR2 containing an amino acid sequence represented by SEQ ID NO: 36, a heavy chain CDR3 containing an amino acid sequence represented by SEQ ID NO: 37, a light chain CDR1 containing an amino acid sequence represented by SEQ ID NO: 38, a light chain CDR2 containing an amino acid sequence represented by SEQ ID NO: 39, and a light chain CDR3 containing an amino acid sequence represented by SEQ ID NO: 40, (B5) comprising a heavy chain CDR1 containing an amino acid sequence represented by SEQ ID NO: 45, a heavy chain CDR2 containing an amino acid sequence represented by SEQ ID NO: 46, a heavy chain CDR3 containing an amino acid sequence represented by SEQ ID NO: 47, a light chain CDR1 containing an amino acid sequence represented by SEQ ID NO: 48, a light chain CDR2 containing an amino acid sequence represented by SEQ ID NO: 49, and a light chain CDR3 containing an amino acid sequence represented by SEQ ID NO: 50, (B6) comprising a heavy chain CDR1 containing an amino acid sequence represented by SEQ ID NO: 55, a heavy chain CDR2 containing an amino acid sequence represented by SEQ ID NO: 56, a heavy chain CDR3 containing an amino acid sequence represented by SEQ ID NO: 57, a light chain CDR1 containing an amino acid sequence represented by SEQ ID NO: 58, a light chain CDR2 containing an amino acid sequence represented by SEQ ID NO: 59, and a light chain CDR3 containing an amino acid sequence represented by SEQ ID NO: 60, (B7) comprising a heavy chain CDR1 containing an amino acid sequence represented by SEQ ID NO: 65, a heavy chain CDR2 containing an amino acid sequence represented by SEQ ID NO: 66, a heavy chain CDR3 containing an amino acid sequence represented by SEQ ID NO: 67, a light chain CDR1 containing an amino acid sequence represented by SEQ ID NO: 68, a light chain CDR2 containing an amino acid sequence represented by SEQ ID NO: 69, and a light chain CDR3 containing an amino acid sequence represented by SEQ ID NO: 70, and (B8) comprising a heavy chain CDR1 containing an amino acid sequence represented by SEQ ID NO: 75, a heavy chain CDR2 containing an amino acid sequence represented by SEQ ID NO: 76, a heavy chain CDR3 containing an amino acid sequence represented by SEQ ID NO: 77, a light chain CDR1 containing an amino acid sequence represented by SEQ ID NO: 78, a light chain CDR2 containing an amino acid sequence represented by SEQ ID NO: 79, and a light chain CDR3 containing an amino acid sequence represented by SEQ ID NO: 80, wherein the antibody is capable of interfering with a CCR7-dependent intracellular signal transduction mechanism caused by CCR7 ligand stimulation, without relying on complement-dependent cell lysis action or antibody-dependent cell-mediated cytotoxicity.

7. The nucleic acid according to claim 6, wherein the anti-human-CCR7 antibody is a humanized antibody or a chimeric antibody.

8. The nucleic acid according to claim 7, wherein the anti-human-CCR7 antibody is an antibody fragment, a single-chain antibody or a diabody.

9. The nucleic acid according to claim 6, wherein the antibody comprises a heavy chain variable region and a light chain variable region of any one of the following (C1) to (C8):

(C1) comprising a heavy chain variable region containing an amino acid sequence represented by SEQ ID NO: 2, and a light chain variable region containing an amino acid sequence represented by SEQ ID NO: 4, (C2) comprising a heavy chain variable region containing an amino acid sequence represented by SEQ ID NO: 12, and a light chain variable region containing an amino acid sequence represented by SEQ ID NO: 14, (C3) comprising a heavy chain variable region containing an amino acid sequence represented by SEQ ID NO: 22, and a light chain variable region containing an amino acid sequence represented by SEQ ID NO: 24, (C4) comprising a heavy chain variable region containing an amino acid sequence represented by SEQ ID NO: 32, and a light chain variable region containing an amino acid sequence represented by SEQ ID NO: 34, (C5) comprising a heavy chain variable region containing an amino acid sequence represented by SEQ ID NO: 42, and a light chain variable region containing an amino acid sequence represented by SEQ ID NO: 44, (C6) comprising a heavy chain variable region containing an amino acid sequence represented by SEQ ID NO: 52, and a light chain variable region containing an amino acid sequence represented by SEQ ID NO: 54, (C7) comprising a heavy chain variable region containing an amino acid sequence represented by SEQ ID NO: 62, and a light chain variable region containing an amino acid sequence represented by SEQ ID NO: 64, and (C8) comprising a heavy chain variable region containing an amino acid sequence represented by SEQ ID NO: 72, and a light chain variable region containing an amino acid sequence represented by SEQ ID NO: 74.

10. The nucleic acid according to claim 9, wherein the anti-human-CCR7 antibody is a humanized antibody or a chimeric antibody.

11. The nucleic acid according to claim 10, wherein the anti-human-CCR7 antibody is an antibody fragment, a single-chain antibody or a diabody.

12. The nucleic acid according to claim 6, comprising a nucleotide sequence selected from the group consisting of SEQ ID NO: 1, SEQ ID NO: 3, SEQ ID NO: 11, SEQ ID NO: 13, SEQ ID NO: 21, SEQ ID NO: 23, SEQ ID NO: 31, SEQ ID NO: 33, SEQ ID NO: 41, SEQ ID NO: 43, SEQ ID NO: 51, SEQ ID NO: 53, SEQ ID NO: 61, SEQ ID NO: 63, SEQ ID NO: 71, and SEQ ID NO: 73.

13. A vector comprising the nucleic acid according to claim 6.

14. A cell into which the vector according to claim 13 has been introduced.

* * * * *

SEQUENCE LISTING

<160> NUMBER OF SEQ ID NOS: 91

<210> SEQ ID NO 1
<211> LENGTH: 390
<212> TYPE: DNA

```
<213> ORGANISM: Mus musculus
<220> FEATURE:
<221> NAME/KEY: CDS
<222> LOCATION: (1)..(390)
<223> OTHER INFORMATION:

<400> SEQUENCE: 1 gag gtt cag ctt cag cag tct gga cct gaa ctg gtg aag cct ggg act       48
Glu Val Gln Leu Gln Gln Ser Gly Pro Glu Leu Val Lys Pro Gly Thr
1               5                   10                  15 tca gtg aag atg tcc tgt aag ggt tct gga tac aca ttc act gac tac       96
Ser Val Lys Met Ser Cys Lys Gly Ser Gly Tyr Thr Phe Thr Asp Tyr
            20                  25                  30 tac ata aac tgg gtg agg cag agt cat gga aag agc ctt gag tgg att      144
Tyr Ile Asn Trp Val Arg Gln Ser His Gly Lys Ser Leu Glu Trp Ile
        35                  40                  45 gga cgt gtt aat cct ggc aat ggt ggt act agt tac aac cag agg ttc      192
Gly Arg Val Asn Pro Gly Asn Gly Gly Thr Ser Tyr Asn Gln Arg Phe
    50                  55                  60 aag ggc aag gcc aca ttg aca gta gac aaa ttc ctc agc aca gcc ttc      240
Lys Gly Lys Ala Thr Leu Thr Val Asp Lys Phe Leu Ser Thr Ala Phe
65                  70                  75                  80 atg cag ctc aac agc ctg aca tct gag gac tct gcg gtc tat ttc tgt      288
Met Gln Leu Asn Ser Leu Thr Ser Glu Asp Ser Ala Val Tyr Phe Cys
                85                  90                  95 gca aga acg ggg act tac tat aat tac gac agg ggt gga ttt gct tac      336
Ala Arg Thr Gly Thr Tyr Tyr Asn Tyr Asp Arg Gly Gly Phe Ala Tyr
            100                 105                 110 tgg ggc cac ggg act ctg gtc act gtc tct gca gcc aaa aca aca ccc      384
Trp Gly His Gly Thr Leu Val Thr Val Ser Ala Ala Lys Thr Thr Pro
        115                 120                 125 cca tct                                                              390
Pro Ser
    130

<210> SEQ ID NO 2
<211> LENGTH: 130
<212> TYPE: PRT
<213> ORGANISM: Mus musculus

<400> SEQUENCE: 2

Glu Val Gln Leu Gln Gln Ser Gly Pro Glu Leu Val Lys Pro Gly Thr
1               5                   10                  15

Ser Val Lys Met Ser Cys Lys Gly Ser Gly Tyr Thr Phe Thr Asp Tyr
            20                  25                  30

Tyr Ile Asn Trp Val Arg Gln Ser His Gly Lys Ser Leu Glu Trp Ile
        35                  40                  45

Gly Arg Val Asn Pro Gly Asn Gly Gly Thr Ser Tyr Asn Gln Arg Phe
    50                  55                  60

Lys Gly Lys Ala Thr Leu Thr Val Asp Lys Phe Leu Ser Thr Ala Phe
65                  70                  75                  80

Met Gln Leu Asn Ser Leu Thr Ser Glu Asp Ser Ala Val Tyr Phe Cys
                85                  90                  95

Ala Arg Thr Gly Thr Tyr Tyr Asn Tyr Asp Arg Gly Gly Phe Ala Tyr
            100                 105                 110

Trp Gly His Gly Thr Leu Val Thr Val Ser Ala Ala Lys Thr Thr Pro
        115                 120                 125

Pro Ser
    130
```

```
<210> SEQ ID NO 3
<211> LENGTH: 324
<212> TYPE: DNA
<213> ORGANISM: Mus musculus
<220> FEATURE:
<221> NAME/KEY: CDS
<222> LOCATION: (1)..(324)
<223> OTHER INFORMATION:

<400> SEQUENCE: 3 gat gtt ttg ctg acc caa agt cca gtc tcc ctg cct gtc agt ctt gga        48
Asp Val Leu Leu Thr Gln Ser Pro Val Ser Leu Pro Val Ser Leu Gly
1               5                   10                  15 gat caa gcc tcc atc tct tgc aga tgt agt cag aac att gtg cat att        96
Asp Gln Ala Ser Ile Ser Cys Arg Cys Ser Gln Asn Ile Val His Ile
            20                  25                  30 aat gga aac acc tat tta gaa tgg ttc ctg cag aaa cca ggc cag tct       144
Asn Gly Asn Thr Tyr Leu Glu Trp Phe Leu Gln Lys Pro Gly Gln Ser
        35                  40                  45 cca aag ctc ctg atc tac aaa gtt tcc aac cga ttt tct ggg gtc cca       192
Pro Lys Leu Leu Ile Tyr Lys Val Ser Asn Arg Phe Ser Gly Val Pro
    50                  55                  60 gac agg ttc agt ggc agt gga tca ggg aca gat ttc aca ctc aaa atc       240
Asp Arg Phe Ser Gly Ser Gly Ser Gly Thr Asp Phe Thr Leu Lys Ile
65                  70                  75                  80 aga aga gtg gag gct gag gat ctg gga gtt tat tac tgc ttt caa ggt       288
Arg Arg Val Glu Ala Glu Asp Leu Gly Val Tyr Tyr Cys Phe Gln Gly
                85                  90                  95 tca cat gtt cct cac acg ttc ggc tcg ggg aca aag                       324
Ser His Val Pro His Thr Phe Gly Ser Gly Thr Lys
                100                 105

<210> SEQ ID NO 4
<211> LENGTH: 108
<212> TYPE: PRT
<213> ORGANISM: Mus musculus

<400> SEQUENCE: 4

Asp Val Leu Leu Thr Gln Ser Pro Val Ser Leu Pro Val Ser Leu Gly
1               5                   10                  15

Asp Gln Ala Ser Ile Ser Cys Arg Cys Ser Gln Asn Ile Val His Ile
            20                  25                  30

Asn Gly Asn Thr Tyr Leu Glu Trp Phe Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Arg Arg Val Glu Ala Glu Asp Leu Gly Val Tyr Tyr Cys Phe Gln Gly
                85                  90                  95

Ser His Val Pro His Thr Phe Gly Ser Gly Thr Lys
                100                 105

<210> SEQ ID NO 5
<211> LENGTH: 9
<212> TYPE: PRT
<213> ORGANISM: Mus musculus

<400> SEQUENCE: 5

Tyr Thr Phe Thr Asp Tyr Tyr Ile Asn
1               5
```

```
<210> SEQ ID NO 6
<211> LENGTH: 17
<212> TYPE: PRT
<213> ORGANISM: Mus musculus

<400> SEQUENCE: 6

Arg Val Asn Pro Gly Asn Gly Gly Thr Ser Tyr Asn Gln Arg Phe Lys
1               5                   10                  15
Gly

<210> SEQ ID NO 7
<211> LENGTH: 16
<212> TYPE: PRT
<213> ORGANISM: Mus musculus

<400> SEQUENCE: 7

Ala Arg Thr Gly Thr Tyr Tyr Asn Tyr Asp Arg Gly Gly Phe Ala Tyr
1               5                   10                  15

<210> SEQ ID NO 8
<211> LENGTH: 16
<212> TYPE: PRT
<213> ORGANISM: Mus musculus

<400> SEQUENCE: 8

Arg Cys Ser Gln Asn Ile Val His Ile Asn Gly Asn Thr Tyr Leu Glu
1               5                   10                  15

<210> SEQ ID NO 9
<211> LENGTH: 14
<212> TYPE: PRT
<213> ORGANISM: Mus musculus

<400> SEQUENCE: 9

Lys Val Ser Asn Arg Phe Ser Gly Val Pro Asp Arg Phe Ser
1               5                   10

<210> SEQ ID NO 10
<211> LENGTH: 9
<212> TYPE: PRT
<213> ORGANISM: Mus musculus

<400> SEQUENCE: 10

Phe Gln Gly Ser His Val Pro His Thr
1               5

<210> SEQ ID NO 11
<211> LENGTH: 423
<212> TYPE: DNA
<213> ORGANISM: Mus musculus
<220> FEATURE:
<221> NAME/KEY: CDS
<222> LOCATION: (1)..(423)
<223> OTHER INFORMATION:

<400> SEQUENCE: 11 ttg cat gcc tgc agg tcg act cta gag gat cta cta gtc ata tgg att    48
Leu His Ala Cys Arg Ser Thr Leu Glu Asp Leu Leu Val Ile Trp Ile
1               5                   10                  15 cag gtt cag ctg cag caa tct ggg gct gag ctt gag agg cca ggg gcc    96
Gln Val Gln Leu Gln Gln Ser Gly Ala Glu Leu Glu Arg Pro Gly Ala
                20                  25                  30 tca gtc aaa ctg tcc tgc aca gct tct ggc ttt aac att aga gac gac    144
```

```
Ser Val Lys Leu Ser Cys Thr Ala Ser Gly Phe Asn Ile Arg Asp Asp
         35                  40                  45 tat gta cac tgg gtg aag cag agg cct gaa cag ggc ctg gag tgg att      192
Tyr Val His Trp Val Lys Gln Arg Pro Glu Gln Gly Leu Glu Trp Ile
         50                  55                  60 ggg agg att gat cct gcg aat ggt aat act aaa tat ggc ccg aag ttc      240
Gly Arg Ile Asp Pro Ala Asn Gly Asn Thr Lys Tyr Gly Pro Lys Phe
65                  70                  75                  80 cag gcc aag gcc act tta act gca gac aca tcc tcc aac aca gcc tac      288
Gln Ala Lys Ala Thr Leu Thr Ala Asp Thr Ser Ser Asn Thr Ala Tyr
                 85                  90                  95 ctg cag ctc ggc agc ctg aca tct gaa gac act gcc gtc tat tac tgt      336
Leu Gln Leu Gly Ser Leu Thr Ser Glu Asp Thr Ala Val Tyr Tyr Cys
             100                 105                 110 act aga tcc ttc tat gat tac gac ttg ttt gtt ccc tgg ggc caa ggg      384
Thr Arg Ser Phe Tyr Asp Tyr Asp Leu Phe Val Pro Trp Gly Gln Gly
             115                 120                 125 act ctg gtc act gtc tct gca gcc aaa aca aca ccc cca                  423
Thr Leu Val Thr Val Ser Ala Ala Lys Thr Thr Pro Pro
        130                 135                 140

<210> SEQ ID NO 12
<211> LENGTH: 141
<212> TYPE: PRT
<213> ORGANISM: Mus musculus

<400> SEQUENCE: 12

Leu His Ala Cys Arg Ser Thr Leu Glu Asp Leu Leu Val Ile Trp Ile
1               5                   10                  15

Gln Val Gln Leu Gln Gln Ser Gly Ala Glu Leu Glu Arg Pro Gly Ala
            20                  25                  30

Ser Val Lys Leu Ser Cys Thr Ala Ser Gly Phe Asn Ile Arg Asp Asp
        35                  40                  45

Tyr Val His Trp Val Lys Gln Arg Pro Glu Gln Gly Leu Glu Trp Ile
        50                  55                  60

Gly Arg Ile Asp Pro Ala Asn Gly Asn Thr Lys Tyr Gly Pro Lys Phe
65                  70                  75                  80

Gln Ala Lys Ala Thr Leu Thr Ala Asp Thr Ser Ser Asn Thr Ala Tyr
                85                  90                  95

Leu Gln Leu Gly Ser Leu Thr Ser Glu Asp Thr Ala Val Tyr Tyr Cys
            100                 105                 110

Thr Arg Ser Phe Tyr Asp Tyr Asp Leu Phe Val Pro Trp Gly Gln Gly
            115                 120                 125

Thr Leu Val Thr Val Ser Ala Ala Lys Thr Thr Pro Pro
        130                 135                 140

<210> SEQ ID NO 13
<211> LENGTH: 315
<212> TYPE: DNA
<213> ORGANISM: Mus musculus
<220> FEATURE:
<221> NAME/KEY: CDS
<222> LOCATION: (1)..(315)
<223> OTHER INFORMATION:

<400> SEQUENCE: 13 gat gct gtt gtg act cag gaa tct gca ctc acc aca tca cct ggt gaa      48
Asp Ala Val Val Thr Gln Glu Ser Ala Leu Thr Thr Ser Pro Gly Glu
1               5                   10                  15 aca gtc aca ctc act tgt cgc tca agt act ggg gct gtt aca aaa aat      96
```

```
                Thr Val Thr Leu Thr Cys Arg Ser Ser Thr Gly Ala Val Thr Lys Asn
                                 20                  25                  30 aac ttt gcc aac tgg gtc caa gaa aaa cca gat cat tta ttc act ggt           144
Asn Phe Ala Asn Trp Val Gln Glu Lys Pro Asp His Leu Phe Thr Gly
             35                  40                  45 cta ata ggt ggt aac aac atc cga gct cca ggt gtt ccg gcc aga ttc           192
Leu Ile Gly Gly Asn Asn Ile Arg Ala Pro Gly Val Pro Ala Arg Phe
 50                  55                  60 tca ggt tcc ctg att gga gac aag gct gcc ctc agt atc aca ggg gca           240
Ser Gly Ser Leu Ile Gly Asp Lys Ala Ala Leu Ser Ile Thr Gly Ala
 65                  70                  75                  80 cag act gag gat gag gca ata tat ttc tgt gct cta tgg tac agc aac           288
Gln Thr Glu Asp Glu Ala Ile Tyr Phe Cys Ala Leu Trp Tyr Ser Asn
                 85                  90                  95 cat tgg gtg ttc ggt gga gga acc aaa                                       315
His Trp Val Phe Gly Gly Gly Thr Lys
                100                 105

<210> SEQ ID NO 14
<211> LENGTH: 105
<212> TYPE: PRT
<213> ORGANISM: Mus musculus

<400> SEQUENCE: 14

Asp Ala Val Val Thr Gln Glu Ser Ala Leu Thr Thr Ser Pro Gly Glu
 1               5                  10                  15

Thr Val Thr Leu Thr Cys Arg Ser Ser Thr Gly Ala Val Thr Lys Asn
                 20                  25                  30

Asn Phe Ala Asn Trp Val Gln Glu Lys Pro Asp His Leu Phe Thr Gly
             35                  40                  45

Leu Ile Gly Gly Asn Asn Ile Arg Ala Pro Gly Val Pro Ala Arg Phe
 50                  55                  60

Ser Gly Ser Leu Ile Gly Asp Lys Ala Ala Leu Ser Ile Thr Gly Ala
 65                  70                  75                  80

Gln Thr Glu Asp Glu Ala Ile Tyr Phe Cys Ala Leu Trp Tyr Ser Asn
                 85                  90                  95

His Trp Val Phe Gly Gly Gly Thr Lys
                100                 105

<210> SEQ ID NO 15
<211> LENGTH: 9
<212> TYPE: PRT
<213> ORGANISM: Mus musculus

<400> SEQUENCE: 15

Phe Asn Ile Arg Asp Asp Tyr Val His
 1               5

<210> SEQ ID NO 16
<211> LENGTH: 17
<212> TYPE: PRT
<213> ORGANISM: Mus musculus

<400> SEQUENCE: 16

Arg Ile Asp Pro Ala Asn Gly Asn Thr Lys Tyr Gly Pro Lys Phe Gln
 1               5                  10                  15

Ala

<210> SEQ ID NO 17
<211> LENGTH: 12
```

```
<212> TYPE: PRT
<213> ORGANISM: Mus musculus

<400> SEQUENCE: 17

Thr Arg Ser Phe Tyr Asp Tyr Asp Leu Phe Val Pro
1               5                   10

<210> SEQ ID NO 18
<211> LENGTH: 14
<212> TYPE: PRT
<213> ORGANISM: Mus musculus

<400> SEQUENCE: 18

Arg Ser Ser Thr Gly Ala Val Thr Lys Asn Asn Phe Ala Asn
1               5                   10

<210> SEQ ID NO 19
<211> LENGTH: 7
<212> TYPE: PRT
<213> ORGANISM: Mus musculus

<400> SEQUENCE: 19

Gly Asn Asn Ile Arg Ala Pro
1               5

<210> SEQ ID NO 20
<211> LENGTH: 9
<212> TYPE: PRT
<213> ORGANISM: Mus musculus

<400> SEQUENCE: 20

Ala Leu Trp Tyr Ser Asn His Trp Val
1               5

<210> SEQ ID NO 21
<211> LENGTH: 384
<212> TYPE: DNA
<213> ORGANISM: Mus musculus
<220> FEATURE:
<221> NAME/KEY: CDS
<222> LOCATION: (1)..(384)
<223> OTHER INFORMATION:

<400> SEQUENCE: 21 ata tgg att gag gtc cag ctc cag cag tct ggg gct gaa ctt gtg agg        48
Ile Trp Ile Glu Val Gln Leu Gln Gln Ser Gly Ala Glu Leu Val Arg
1               5                   10                  15 cca ggg gcc tca gtc aag ttg tcc tgc aca gct tct ggc ttt aac att        96
Pro Gly Ala Ser Val Lys Leu Ser Cys Thr Ala Ser Gly Phe Asn Ile
            20                  25                  30 aaa gac gac tat ata cac tgg gtg aag cag agg cct gaa cag ggc ctg       144
Lys Asp Asp Tyr Ile His Trp Val Lys Gln Arg Pro Glu Gln Gly Leu
        35                  40                  45 gac tgg att gga agg gtt gat cct gcg gat ggt aat act aaa tat gcc       192
Asp Trp Ile Gly Arg Val Asp Pro Ala Asp Gly Asn Thr Lys Tyr Ala
    50                  55                  60 cca aac ttc cac gac aag gcc act gta act gca gac aca tcc tcc aac       240
Pro Asn Phe His Asp Lys Ala Thr Val Thr Ala Asp Thr Ser Ser Asn
65                  70                  75                  80 aca gcc tac ctg caa ctc agc agc ctg aca tct gag gac act gcc gtc       288
Thr Ala Tyr Leu Gln Leu Ser Ser Leu Thr Ser Glu Asp Thr Ala Val
                85                  90                  95 tat tac tgt gct aga tcc ttc tat gat tac gac ttg ttt gct tcc tgg       336
Tyr Tyr Cys Ala Arg Ser Phe Tyr Asp Tyr Asp Leu Phe Ala Ser Trp
```

```
                        100                 105                 110
ggc caa ggg act ctg gtc act gtc tct gca gcc aaa aca aca ccc cca         384
Gly Gln Gly Thr Leu Val Thr Val Ser Ala Ala Lys Thr Thr Pro Pro
            115                 120                 125

<210> SEQ ID NO 22
<211> LENGTH: 128
<212> TYPE: PRT
<213> ORGANISM: Mus musculus

<400> SEQUENCE: 22

Ile Trp Ile Glu Val Gln Leu Gln Gln Ser Gly Ala Glu Leu Val Arg
1               5                   10                  15

Pro Gly Ala Ser Val Lys Leu Ser Cys Thr Ala Ser Gly Phe Asn Ile
            20                  25                  30

Lys Asp Asp Tyr Ile His Trp Val Lys Gln Arg Pro Glu Gln Gly Leu
        35                  40                  45

Asp Trp Ile Gly Arg Val Asp Pro Ala Asp Gly Asn Thr Lys Tyr Ala
    50                  55                  60

Pro Asn Phe His Asp Lys Ala Thr Val Thr Ala Asp Thr Ser Ser Asn
65                  70                  75                  80

Thr Ala Tyr Leu Gln Leu Ser Ser Leu Thr Ser Glu Asp Thr Ala Val
                85                  90                  95

Tyr Tyr Cys Ala Arg Ser Phe Tyr Asp Tyr Asp Leu Phe Ala Ser Trp
            100                 105                 110

Gly Gln Gly Thr Leu Val Thr Val Ser Ala Ala Lys Thr Thr Pro Pro
            115                 120                 125

<210> SEQ ID NO 23
<211> LENGTH: 315
<212> TYPE: DNA
<213> ORGANISM: Mus musculus
<220> FEATURE:
<221> NAME/KEY: CDS
<222> LOCATION: (1)..(315)
<223> OTHER INFORMATION:

<400> SEQUENCE: 23 gat gct gtt gtg act cag gaa tct gca ctc acc aca tca cct ggt gaa         48
Asp Ala Val Val Thr Gln Glu Ser Ala Leu Thr Thr Ser Pro Gly Glu
1               5                   10                  15 aca gtc aca ctc act tgt cgc tca agt act ggg gct gtt aca act agt         96
Thr Val Thr Leu Thr Cys Arg Ser Ser Thr Gly Ala Val Thr Thr Ser
            20                  25                  30 aac ttt gcc aac tgg gtc caa gaa aaa cca gat cat tta ttc act ggt         144
Asn Phe Ala Asn Trp Val Gln Glu Lys Pro Asp His Leu Phe Thr Gly
        35                  40                  45 ctg ata agt agt aac aac aaa cga gct cca ggt gtt cct gcc aga ttc         192
Leu Ile Ser Ser Asn Asn Lys Arg Ala Pro Gly Val Pro Ala Arg Phe
    50                  55                  60 tca ggc tcc ctg att gga gac aag gct gcc ctc agt atc aca ggg gca         240
Ser Gly Ser Leu Ile Gly Asp Lys Ala Ala Leu Ser Ile Thr Gly Ala
65                  70                  75                  80 cag act gag gat gag gca ata tat ttc tgt gct cta tgg tac agc aac         288
Gln Thr Glu Asp Glu Ala Ile Tyr Phe Cys Ala Leu Trp Tyr Ser Asn
                85                  90                  95 cat tgg gtg ttc ggt gga gga acc aaa                                      315
His Trp Val Phe Gly Gly Gly Thr Lys
            100                 105
```

```
<210> SEQ ID NO 24
<211> LENGTH: 105
<212> TYPE: PRT
<213> ORGANISM: Mus musculus

<400> SEQUENCE: 24

Asp Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Phe Ala Asn Trp Val Gln Glu Lys Pro Asp His Leu Phe Thr Gly
        35                  40                  45

Leu Ile Ser Ser Asn Asn Lys Arg Ala Pro Gly Val Pro Ala Arg Phe
    50                  55                  60

Ser Gly Ser Leu Ile Gly Asp Lys Ala Ala Leu Ser Ile Thr Gly Ala
65                  70                  75                  80

Gln Thr Glu Asp Glu Ala Ile Tyr Phe Cys Ala Leu Trp Tyr Ser Asn
                85                  90                  95

His Trp Val Phe Gly Gly Gly Thr Lys
            100                 105

<210> SEQ ID NO 25
<211> LENGTH: 9
<212> TYPE: PRT
<213> ORGANISM: Mus musculus

<400> SEQUENCE: 25

Phe Asn Ile Lys Asp Tyr Ile His
1               5

<210> SEQ ID NO 26
<211> LENGTH: 17
<212> TYPE: PRT
<213> ORGANISM: Mus musculus

<400> SEQUENCE: 26

Arg Val Asp Pro Ala Asp Gly Asn Thr Lys Tyr Ala Pro Asn Phe His
1               5                   10                  15

Asp

<210> SEQ ID NO 27
<211> LENGTH: 12
<212> TYPE: PRT
<213> ORGANISM: Mus musculus

<400> SEQUENCE: 27

Ala Arg Ser Phe Tyr Asp Tyr Asp Leu Phe Ala Ser
1               5                   10

<210> SEQ ID NO 28
<211> LENGTH: 14
<212> TYPE: PRT
<213> ORGANISM: Mus musculus

<400> SEQUENCE: 28

Arg Ser Ser Thr Gly Ala Val Thr Thr Ser Asn Phe Ala Asn
1               5                   10

<210> SEQ ID NO 29
<211> LENGTH: 7
<212> TYPE: PRT
<213> ORGANISM: Mus musculus
```

<400> SEQUENCE: 29

Ser Asn Asn Lys Arg Ala Pro
1               5

<210> SEQ ID NO 30
<211> LENGTH: 9
<212> TYPE: PRT
<213> ORGANISM: Mus musculus

<400> SEQUENCE: 30

Ala Leu Trp Tyr Ser Asn His Trp Val
1               5

<210> SEQ ID NO 31
<211> LENGTH: 378
<212> TYPE: DNA
<213> ORGANISM: Mus musculus
<220> FEATURE:
<221> NAME/KEY: CDS
<222> LOCATION: (1)..(378)
<223> OTHER INFORMATION:

<400> SEQUENCE: 31 att gag gtt cag ctc cag cag tct ggg act gaa ctt gtg agg cca ggg      48
Ile Glu Val Gln Leu Gln Gln Ser Gly Thr Glu Leu Val Arg Pro Gly
1               5                   10                  15 gcc tca gtc aag ttg tcc tgc aca gct tct ggc ttt aac att aaa gac      96
Ala Ser Val Lys Leu Ser Cys Thr Ala Ser Gly Phe Asn Ile Lys Asp
            20                  25                  30 gac tat ata cac tgg gtg aag cag agg cct gac cag ggc ctg gag tgg     144
Asp Tyr Ile His Trp Val Lys Gln Arg Pro Asp Gln Gly Leu Glu Trp
        35                  40                  45 att gga agg att gat cct gcg aat ggt aat act aaa tat gcc ccg aag     192
Ile Gly Arg Ile Asp Pro Ala Asn Gly Asn Thr Lys Tyr Ala Pro Lys
    50                  55                  60 ttc cag gac aag gcc act ata act tca gac aca tcc tcc aac aca gcc     240
Phe Gln Asp Lys Ala Thr Ile Thr Ser Asp Thr Ser Ser Asn Thr Ala
65                  70                  75                  80 tac ctg caa ctc agc agc ctg aca tct gag gac act gcc gtc tat tac     288
Tyr Leu Gln Leu Ser Ser Leu Thr Ser Glu Asp Thr Ala Val Tyr Tyr
                85                  90                  95 tgt gct aga tcc ttc tat gat tac gac ttg ttt gct tcc tgg ggc caa     336
Cys Ala Arg Ser Phe Tyr Asp Tyr Asp Leu Phe Ala Ser Trp Gly Gln
            100                 105                 110 ggg act ctg gtc tct gtc tct gca gcc aaa aca aca ccc cca             378
Gly Thr Leu Val Ser Val Ser Ala Ala Lys Thr Thr Pro Pro
        115                 120                 125

<210> SEQ ID NO 32
<211> LENGTH: 126
<212> TYPE: PRT
<213> ORGANISM: Mus musculus

<400> SEQUENCE: 32

Ile Glu Val Gln Leu Gln Gln Ser Gly Thr Glu Leu Val Arg Pro Gly
1               5                   10                  15

Ala Ser Val Lys Leu Ser Cys Thr Ala Ser Gly Phe Asn Ile Lys Asp
            20                  25                  30

Asp Tyr Ile His Trp Val Lys Gln Arg Pro Asp Gln Gly Leu Glu Trp
        35                  40                  45

Ile Gly Arg Ile Asp Pro Ala Asn Gly Asn Thr Lys Tyr Ala Pro Lys

```
                50                  55                  60
Phe Gln Asp Lys Ala Thr Ile Thr Ser Asp Thr Ser Ser Asn Thr Ala
 65                  70                  75                  80

Tyr Leu Gln Leu Ser Ser Leu Thr Ser Glu Asp Thr Ala Val Tyr Tyr
                 85                  90                  95

Cys Ala Arg Ser Phe Tyr Asp Tyr Asp Leu Phe Ala Ser Trp Gly Gln
                100                 105                 110

Gly Thr Leu Val Ser Val Ser Ala Ala Lys Thr Thr Pro Pro
            115                 120                 125

<210> SEQ ID NO 33
<211> LENGTH: 315
<212> TYPE: DNA
<213> ORGANISM: Mus musculus
<220> FEATURE:
<221> NAME/KEY: CDS
<222> LOCATION: (1)..(315)
<223> OTHER INFORMATION:

<400> SEQUENCE: 33 gat gct gtt gtg act cag gaa tct gca ctc acc aca tca cct ggt gga        48
Asp Ala Val Val Thr Gln Glu Ser Ala Leu Thr Thr Ser Pro Gly Gly
 1               5                  10                  15 aca gtc ata ctc act tgt cgc tca agt act ggg gct gtt aca act agt        96
Thr Val Ile Leu Thr Cys Arg Ser Ser Thr Gly Ala Val Thr Thr Ser
                20                  25                  30 aac ttt gcc aac tgg gtc caa gaa aaa cca gat cat tta ttc tct ggt       144
Asn Phe Ala Asn Trp Val Gln Glu Lys Pro Asp His Leu Phe Ser Gly
             35                  40                  45 cta ata agt ggt aac aac aaa cga gct cca ggt gtt ccc gcc aga ttc       192
Leu Ile Ser Gly Asn Asn Lys Arg Ala Pro Gly Val Pro Ala Arg Phe
         50                  55                  60 tca ggc tcc ctg att gga gac aag gct gcc ctc agt atc acc ggg gca       240
Ser Gly Ser Leu Ile Gly Asp Lys Ala Ala Leu Ser Ile Thr Gly Ala
 65                  70                  75                  80 cag act gag gat gag gca atg tat ttc tgt gct cta tgg tac aac aac       288
Gln Thr Glu Asp Glu Ala Met Tyr Phe Cys Ala Leu Trp Tyr Asn Asn
                 85                  90                  95 cat tgg gtg ttc ggt gga gga acc aaa                                   315
His Trp Val Phe Gly Gly Gly Thr Lys
            100                 105

<210> SEQ ID NO 34
<211> LENGTH: 105
<212> TYPE: PRT
<213> ORGANISM: Mus musculus

<400> SEQUENCE: 34

Asp Ala Val Val Thr Gln Glu Ser Ala Leu Thr Thr Ser Pro Gly Gly
 1               5                  10                  15

Thr Val Ile Leu Thr Cys Arg Ser Ser Thr Gly Ala Val Thr Thr Ser
                20                  25                  30

Asn Phe Ala Asn Trp Val Gln Glu Lys Pro Asp His Leu Phe Ser Gly
             35                  40                  45

Leu Ile Ser Gly Asn Asn Lys Arg Ala Pro Gly Val Pro Ala Arg Phe
         50                  55                  60

Ser Gly Ser Leu Ile Gly Asp Lys Ala Ala Leu Ser Ile Thr Gly Ala
 65                  70                  75                  80

Gln Thr Glu Asp Glu Ala Met Tyr Phe Cys Ala Leu Trp Tyr Asn Asn
                 85                  90                  95
```

His Trp Val Phe Gly Gly Gly Thr Lys
            100                 105

<210> SEQ ID NO 35
<211> LENGTH: 9
<212> TYPE: PRT
<213> ORGANISM: Mus musculus

<400> SEQUENCE: 35

Phe Asn Ile Lys Asp Asp Tyr Ile His
1               5

<210> SEQ ID NO 36
<211> LENGTH: 17
<212> TYPE: PRT
<213> ORGANISM: Mus musculus

<400> SEQUENCE: 36

Arg Ile Asp Pro Ala Asn Gly Asn Thr Lys Tyr Ala Pro Lys Phe Gln
1               5                   10                  15

Asp

<210> SEQ ID NO 37
<211> LENGTH: 12
<212> TYPE: PRT
<213> ORGANISM: Mus musculus

<400> SEQUENCE: 37

Ala Arg Ser Phe Tyr Asp Tyr Asp Leu Phe Ala Ser
1               5                   10

<210> SEQ ID NO 38
<211> LENGTH: 14
<212> TYPE: PRT
<213> ORGANISM: Mus musculus

<400> SEQUENCE: 38

Arg Ser Ser Thr Gly Ala Val Thr Thr Ser Asn Phe Ala Asn
1               5                   10

<210> SEQ ID NO 39
<211> LENGTH: 7
<212> TYPE: PRT
<213> ORGANISM: Mus musculus

<400> SEQUENCE: 39

Gly Asn Asn Lys Arg Ala Pro
1               5

<210> SEQ ID NO 40
<211> LENGTH: 9
<212> TYPE: PRT
<213> ORGANISM: Mus musculus

<400> SEQUENCE: 40

Ala Leu Trp Tyr Asn Asn His Trp Val
1               5

<210> SEQ ID NO 41
<211> LENGTH: 378
<212> TYPE: DNA
<213> ORGANISM: Mus musculus
<220> FEATURE:
<221> NAME/KEY: CDS

```
<222> LOCATION: (1)..(378)
<223> OTHER INFORMATION:

<400> SEQUENCE: 41 tgg att gag gtt cag ctt cag cag tct gga cct gac ctg gtg atg cct    48
Trp Ile Glu Val Gln Leu Gln Gln Ser Gly Pro Asp Leu Val Met Pro
1               5                   10                  15 ggg gct tca gtg agg ata tcc tgc aag gct tct ggt tac tct ttc act    96
Gly Ala Ser Val Arg Ile Ser Cys Lys Ala Ser Gly Tyr Ser Phe Thr
            20                  25                  30 gcc tac tac atg cac tgg gtg aag cag agc cat gga ttg agc ctt gag    144
Ala Tyr Tyr Met His Trp Val Lys Gln Ser His Gly Leu Ser Leu Glu
        35                  40                  45 tgg att gga cgt gtt aat cct aac aat ggt ggt act agc tac aac cgg    192
Trp Ile Gly Arg Val Asn Pro Asn Asn Gly Gly Thr Ser Tyr Asn Arg
    50                  55                  60 aaa ttc aag gac aag gcc ata tta act gta gac agg tca tcc agc aca    240
Lys Phe Lys Asp Lys Ala Ile Leu Thr Val Asp Arg Ser Ser Ser Thr
65                  70                  75                  80 gcc ttc atg gag ctc cgc agc ctg aca tct gag gac tct gcg gtc tat    288
Ala Phe Met Glu Leu Arg Ser Leu Thr Ser Glu Asp Ser Ala Val Tyr
                85                  90                  95 tac tgt gca aga tcg gag agt gac cat ttc tat gct atg gac tcc tgg    336
Tyr Cys Ala Arg Ser Glu Ser Asp His Phe Tyr Ala Met Asp Ser Trp
            100                 105                 110 ggt caa gga aat tct gtc tcc gtc tcc tca gcc aaa aca aca             378
Gly Gln Gly Asn Ser Val Ser Val Ser Ser Ala Lys Thr Thr
        115                 120                 125

<210> SEQ ID NO 42
<211> LENGTH: 126
<212> TYPE: PRT
<213> ORGANISM: Mus musculus

<400> SEQUENCE: 42

Trp Ile Glu Val Gln Leu Gln Gln Ser Gly Pro Asp Leu Val Met Pro
1               5                   10                  15

Gly Ala Ser Val Arg Ile Ser Cys Lys Ala Ser Gly Tyr Ser Phe Thr
            20                  25                  30

Ala Tyr Tyr Met His Trp Val Lys Gln Ser His Gly Leu Ser Leu Glu
        35                  40                  45

Trp Ile Gly Arg Val Asn Pro Asn Asn Gly Gly Thr Ser Tyr Asn Arg
    50                  55                  60

Lys Phe Lys Asp Lys Ala Ile Leu Thr Val Asp Arg Ser Ser Ser Thr
65                  70                  75                  80

Ala Phe Met Glu Leu Arg Ser Leu Thr Ser Glu Asp Ser Ala Val Tyr
                85                  90                  95

Tyr Cys Ala Arg Ser Glu Ser Asp His Phe Tyr Ala Met Asp Ser Trp
            100                 105                 110

Gly Gln Gly Asn Ser Val Ser Val Ser Ser Ala Lys Thr Thr
        115                 120                 125

<210> SEQ ID NO 43
<211> LENGTH: 324
<212> TYPE: DNA
<213> ORGANISM: Mus musculus
<220> FEATURE:
<221> NAME/KEY: CDS
<222> LOCATION: (1)..(324)
<223> OTHER INFORMATION:
```

```
<400> SEQUENCE: 43 gac att gtg atg acc caa act cca ctc tcc ctg cct gtc agt ctt gga      48
Asp Ile Val Met Thr Gln Thr Pro Leu Ser Leu Pro Val Ser Leu Gly
1               5                   10                  15 gat caa gtt ttc atc tct tgc aga tct agt cag agc ctt gta cac agc      96
Asp Gln Val Phe Ile Ser Cys Arg Ser Ser Gln Ser Leu Val His Ser
            20                  25                  30 aat gga aac acc tat tta tgt tgg ttc ctg cag aag cca ggc cag tct      144
Asn Gly Asn Thr Tyr Leu Cys Trp Phe Leu Gln Lys Pro Gly Gln Ser
        35                  40                  45 cca aag ctc ctg atc tac agg gtt tcc aac cga ttt tct ggg gtc cca      192
Pro Lys Leu Leu Ile Tyr Arg Val Ser Asn Arg Phe Ser Gly Val Pro
    50                  55                  60 gac agg ttc agt ggc agt gga tca ggg aca gat ttc aca ctc aag atc      240
Asp Arg Phe Ser Gly Ser Gly Ser Gly Thr Asp Phe Thr Leu Lys Ile
65                  70                  75                  80 agc aga gtg gag gct gag gat ctg gga gtt tat ttc tgc ttt caa ggt      288
Ser Arg Val Glu Ala Glu Asp Leu Gly Val Tyr Phe Cys Phe Gln Gly
                85                  90                  95 tca cat gtt cct cat acg ttc gga tcg ggg acc aag                      324
Ser His Val Pro His Thr Phe Gly Ser Gly Thr Lys
            100                 105

<210> SEQ ID NO 44
<211> LENGTH: 108
<212> TYPE: PRT
<213> ORGANISM: Mus musculus

<400> SEQUENCE: 44

Asp Ile Val Met Thr Gln Thr Pro Leu Ser Leu Pro Val Ser Leu Gly
1               5                   10                  15

Asp Gln Val Phe Ile Ser Cys Arg Ser Ser Gln Ser Leu Val His Ser
            20                  25                  30

Asn Gly Asn Thr Tyr Leu Cys Trp Phe Leu Gln Lys Pro Gly Gln Ser
        35                  40                  45

Pro Lys Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Phe Gln Gly
                85                  90                  95

Ser His Val Pro His Thr Phe Gly Ser Gly Thr Lys
            100                 105

<210> SEQ ID NO 45
<211> LENGTH: 9
<212> TYPE: PRT
<213> ORGANISM: Mus musculus

<400> SEQUENCE: 45

Tyr Ser Phe Thr Ala Tyr Tyr Met His
1               5

<210> SEQ ID NO 46
<211> LENGTH: 17
<212> TYPE: PRT
<213> ORGANISM: Mus musculus

<400> SEQUENCE: 46

Arg Val Asn Pro Asn Asn Gly Gly Thr Ser Tyr Asn Arg Lys Phe Lys
```

Asp

<210> SEQ ID NO 47
<211> LENGTH: 13
<212> TYPE: PRT
<213> ORGANISM: Mus musculus

<400> SEQUENCE: 47

Cys Ala Arg Ser Glu Ser Asp His Phe Tyr Ala Met Asp
1               5                   10

<210> SEQ ID NO 48
<211> LENGTH: 16
<212> TYPE: PRT
<213> ORGANISM: Mus musculus

<400> SEQUENCE: 48

Arg Ser Ser Gln Ser Leu Val His Ser Asn Gly Asn Thr Tyr Leu Cys
1               5                   10                  15

<210> SEQ ID NO 49
<211> LENGTH: 7
<212> TYPE: PRT
<213> ORGANISM: Mus musculus

<400> SEQUENCE: 49

Arg Val Ser Asn Arg Phe Ser
1               5

<210> SEQ ID NO 50
<211> LENGTH: 9
<212> TYPE: PRT
<213> ORGANISM: Mus musculus

<400> SEQUENCE: 50

Phe Gln Gly Ser His Val Pro His Thr
1               5

<210> SEQ ID NO 51
<211> LENGTH: 387
<212> TYPE: DNA
<213> ORGANISM: Mus musculus
<220> FEATURE:
<221> NAME/KEY: CDS
<222> LOCATION: (1)..(387)
<223> OTHER INFORMATION:

<400> SEQUENCE: 51

```
ata tgg att gag gtc cag ctg cag cag tct gga cct gac ctg gtg aag      48
Ile Trp Ile Glu Val Gln Leu Gln Gln Ser Gly Pro Asp Leu Val Lys
1               5                   10                  15 cct ggg gct tca gtg aag ata tcc tgc aag gct tct ggt tac tca ttc      96
Pro Gly Ala Ser Val Lys Ile Ser Cys Lys Ala Ser Gly Tyr Ser Phe
            20                  25                  30 act ggc tac tac atg cac tgg gtg aag cag agc cat gga aag agc ctt     144
Thr Gly Tyr Tyr Met His Trp Val Lys Gln Ser His Gly Lys Ser Leu
        35                  40                  45 gag tgg att gga cgt gtt aat cct aac aat ggt gga act agt tac aac     192
Glu Trp Ile Gly Arg Val Asn Pro Asn Asn Gly Gly Thr Ser Tyr Asn
    50                  55                  60 aag aag ttc aag gtc aag gcc ata tta act gtt gac agg tca tcc agc     240
Lys Lys Phe Lys Val Lys Ala Ile Leu Thr Val Asp Arg Ser Ser Ser
65                  70                  75                  80
```

```
aca gcc tac atg gaa ttc cgc agc ctg aca ctc gag gac tct gcg gtc      288
Thr Ala Tyr Met Glu Phe Arg Ser Leu Thr Leu Glu Asp Ser Ala Val
            85                  90                  95 tat tat tgt gca aga tcg gag agt aac aat ttc tat gct atg gac tat      336
Tyr Tyr Cys Ala Arg Ser Glu Ser Asn Asn Phe Tyr Ala Met Asp Tyr
            100                 105                 110 tgg ggc caa gga aag tct gtc acc gtc tct tca gcc aaa aca aca ccc      384
Trp Gly Gln Gly Lys Ser Val Thr Val Ser Ser Ala Lys Thr Thr Pro
        115                 120                 125 cca                                                                  387
Pro

<210> SEQ ID NO 52
<211> LENGTH: 129
<212> TYPE: PRT
<213> ORGANISM: Mus musculus

<400> SEQUENCE: 52

Ile Trp Ile Glu Val Gln Leu Gln Gln Ser Gly Pro Asp Leu Val Lys
1               5                   10                  15

Pro Gly Ala Ser Val Lys Ile Ser Cys Lys Ala Ser Gly Tyr Ser Phe
            20                  25                  30

Thr Gly Tyr Tyr Met His Trp Val Lys Gln Ser His Gly Lys Ser Leu
        35                  40                  45

Glu Trp Ile Gly Arg Val Asn Pro Asn Asn Gly Gly Thr Ser Tyr Asn
    50                  55                  60

Lys Lys Phe Lys Val Lys Ala Ile Leu Thr Val Asp Arg Ser Ser Ser
65                  70                  75                  80

Thr Ala Tyr Met Glu Phe Arg Ser Leu Thr Leu Glu Asp Ser Ala Val
            85                  90                  95

Tyr Tyr Cys Ala Arg Ser Glu Ser Asn Asn Phe Tyr Ala Met Asp Tyr
            100                 105                 110

Trp Gly Gln Gly Lys Ser Val Thr Val Ser Ser Ala Lys Thr Thr Pro
        115                 120                 125

Pro

<210> SEQ ID NO 53
<211> LENGTH: 324
<212> TYPE: DNA
<213> ORGANISM: Mus musculus
<220> FEATURE:
<221> NAME/KEY: CDS
<222> LOCATION: (1)..(324)
<223> OTHER INFORMATION:

<400> SEQUENCE: 53 gat att ttg atg acc caa act cca ctc tcc ctg cct gtc agt ctt gga      48
Asp Ile Leu Met Thr Gln Thr Pro Leu Ser Leu Pro Val Ser Leu Gly
1               5                   10                  15 gat caa gtt tcc atc tct tgc aga tct agt cag agc ctt gta cac agc      96
Asp Gln Val Ser Ile Ser Cys Arg Ser Ser Gln Ser Leu Val His Ser
            20                  25                  30 aat gga aac acc tat tta tgt tgg tac ctg cag aag cca ggc cag tct     144
Asn Gly Asn Thr Tyr Leu Cys Trp Tyr Leu Gln Lys Pro Gly Gln Ser
        35                  40                  45 cca aag ctc ctg atc tac agg gtt tcc aac cga ttt tct ggg gtc ccg     192
Pro Lys Leu Leu Ile Tyr Arg Val Ser Asn Arg Phe Ser Gly Val Pro
    50                  55                  60 gac agg ttc agt ggc agt gga tca ggg aca gat ttc aca ctc aag atc     240
```

```
Asp Arg Phe Ser Gly Ser Gly Ser Gly Thr Asp Phe Thr Leu Lys Ile
65                  70                  75                  80 agc aga gtg gag gct gag gat ctg gga gtt tat ttc tgc ttt caa ggt    288
Ser Arg Val Glu Ala Glu Asp Leu Gly Val Tyr Phe Cys Phe Gln Gly
                85                  90                  95 tca cat gtt cct cat acg ttc gga tcg ggg acc aag                    324
Ser His Val Pro His Thr Phe Gly Ser Gly Thr Lys
            100                 105
```

<210> SEQ ID NO 54
<211> LENGTH: 108
<212> TYPE: PRT
<213> ORGANISM: Mus musculus

<400> SEQUENCE: 54

```
Asp Ile Leu Met Thr Gln Thr Pro Leu Ser Leu Pro Val Ser Leu Gly
1               5                   10                  15

Asp Gln Val Ser Ile Ser Cys Arg Ser Ser Gln Ser Leu Val His Ser
                20                  25                  30

Asn Gly Asn Thr Tyr Leu Cys Trp Tyr Leu Gln Lys Pro Gly Gln Ser
            35                  40                  45

Pro Lys Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Phe Gln Gly
                85                  90                  95

Ser His Val Pro His Thr Phe Gly Ser Gly Thr Lys
            100                 105
```

<210> SEQ ID NO 55
<211> LENGTH: 9
<212> TYPE: PRT
<213> ORGANISM: Mus musculus

<400> SEQUENCE: 55

```
Tyr Ser Phe Thr Gly Tyr Tyr Met His
1               5
```

<210> SEQ ID NO 56
<211> LENGTH: 17
<212> TYPE: PRT
<213> ORGANISM: Mus musculus

<400> SEQUENCE: 56

```
Arg Val Asn Pro Asn Asn Gly Gly Thr Ser Tyr Asn Lys Lys Phe Lys
1               5                   10                  15

Val
```

<210> SEQ ID NO 57
<211> LENGTH: 13
<212> TYPE: PRT
<213> ORGANISM: Mus musculus

<400> SEQUENCE: 57

```
Cys Ala Arg Ser Glu Ser Asn Asn Phe Tyr Ala Met Asp
1               5                   10
```

<210> SEQ ID NO 58
<211> LENGTH: 16
<212> TYPE: PRT

```
<213> ORGANISM: Mus musculus

<400> SEQUENCE: 58

Arg Ser Ser Gln Ser Leu Val His Ser Asn Gly Asn Thr Tyr Leu Cys
1               5                   10                  15

<210> SEQ ID NO 59
<211> LENGTH: 7
<212> TYPE: PRT
<213> ORGANISM: Mus musculus

<400> SEQUENCE: 59

Arg Val Ser Asn Arg Phe Ser
1               5

<210> SEQ ID NO 60
<211> LENGTH: 9
<212> TYPE: PRT
<213> ORGANISM: Mus musculus

<400> SEQUENCE: 60

Phe Gln Gly Ser His Val Pro His Thr
1               5

<210> SEQ ID NO 61
<211> LENGTH: 387
<212> TYPE: DNA
<213> ORGANISM: Mus musculus
<220> FEATURE:
<221> NAME/KEY: CDS
<222> LOCATION: (1)..(387)
<223> OTHER INFORMATION:

<400> SEQUENCE: 61 ata tgg att gag gtg atg gtg gtg gag tca gga cct ggc ctg atg aaa     48
Ile Trp Ile Glu Val Met Val Val Glu Ser Gly Pro Gly Leu Met Lys
1               5                   10                  15 cct tct cag tca ctt tcc ctc acc tgc gct gtc act ggc tat tcc atc     96
Pro Ser Gln Ser Leu Ser Leu Thr Cys Ala Val Thr Gly Tyr Ser Ile
            20                  25                  30 acc agt ggt tat gac tgg cac tgg atc cga cat ttt cca gga aac ata    144
Thr Ser Gly Tyr Asp Trp His Trp Ile Arg His Phe Pro Gly Asn Ile
        35                  40                  45 ctg gag tgg atg ggc tac ata aac tac agt ggt agc act aac tac aaa    192
Leu Glu Trp Met Gly Tyr Ile Asn Tyr Ser Gly Ser Thr Asn Tyr Lys
    50                  55                  60 cca tcc ctc aag agt cga atc tcc atc act ctt gac aca tct aag aac    240
Pro Ser Leu Lys Ser Arg Ile Ser Ile Thr Leu Asp Thr Ser Lys Asn
65                  70                  75                  80 cat ttc ttc ctg aag ttg agt tct gtg act act gaa gac aca gcc aca    288
His Phe Phe Leu Lys Leu Ser Ser Val Thr Thr Glu Asp Thr Ala Thr
                85                  90                  95 tat tac tgt gca aga ggg agt tac tat agt tat gag ttt gct tac tgg    336
Tyr Tyr Cys Ala Arg Gly Ser Tyr Tyr Ser Tyr Glu Phe Ala Tyr Trp
            100                 105                 110 ggc caa ggg act ctg gtc act gtc tct gca gcc aaa aca aca ccc cca    384
Gly Gln Gly Thr Leu Val Thr Val Ser Ala Ala Lys Thr Thr Pro Pro
        115                 120                 125 tct                                                                387
Ser

<210> SEQ ID NO 62
<211> LENGTH: 129
```

```
<212> TYPE: PRT
<213> ORGANISM: Mus musculus

<400> SEQUENCE: 62

Ile Trp Ile Glu Val Met Val Val Glu Ser Gly Pro Gly Leu Met Lys
1               5                   10                  15

Pro Ser Gln Ser Leu Ser Leu Thr Cys Ala Val Thr Gly Tyr Ser Ile
            20                  25                  30

Thr Ser Gly Tyr Asp Trp His Trp Ile Arg His Phe Pro Gly Asn Ile
        35                  40                  45

Leu Glu Trp Met Gly Tyr Ile Asn Tyr Ser Gly Ser Thr Asn Tyr Lys
    50                  55                  60

Pro Ser Leu Lys Ser Arg Ile Ser Ile Thr Leu Asp Thr Ser Lys Asn
65                  70                  75                  80

His Phe Phe Leu Lys Leu Ser Ser Val Thr Thr Glu Asp Thr Ala Thr
                85                  90                  95

Tyr Tyr Cys Ala Arg Gly Ser Tyr Tyr Ser Tyr Glu Phe Ala Tyr Trp
            100                 105                 110

Gly Gln Gly Thr Leu Val Thr Val Ser Ala Ala Lys Thr Thr Pro Pro
        115                 120                 125

Ser

<210> SEQ ID NO 63
<211> LENGTH: 324
<212> TYPE: DNA
<213> ORGANISM: Mus musculus
<220> FEATURE:
<221> NAME/KEY: CDS
<222> LOCATION: (1)..(324)
<223> OTHER INFORMATION:

<400> SEQUENCE: 63 gac att gtg atg tca cag tct cca tcc tcc cta gct gtg tca gtt gga     48
Asp Ile Val Met Ser Gln Ser Pro Ser Ser Leu Ala Val Ser Val Gly
1               5                   10                  15 gag aag gtt act atg agc tgc aag tcc agt cag aga ctt tta tat tat     96
Glu Lys Val Thr Met Ser Cys Lys Ser Ser Gln Arg Leu Leu Tyr Tyr
            20                  25                  30 agc act caa aag aac tac ttg gcc tgg tac cag cag aaa cca ggg cag    144
Ser Thr Gln Lys Asn Tyr Leu Ala Trp Tyr Gln Gln Lys Pro Gly Gln
        35                  40                  45 tct cct aaa ctg ctg att ttc tgg gca tcc act agg gaa tct ggg gtc    192
Ser Pro Lys Leu Leu Ile Phe Trp Ala Ser Thr Arg Glu Ser Gly Val
    50                  55                  60 cct aat cgc ttc aca ggc agt gga tct ggg aca gat ttc act ctc acc    240
Pro Asn Arg Phe Thr Gly Ser Gly Ser Gly Thr Asp Phe Thr Leu Thr
65                  70                  75                  80 atc aac agt gtg aag gct gaa gac ctg gca gtt tat tac tgt cag caa    288
Ile Asn Ser Val Lys Ala Glu Asp Leu Ala Val Tyr Tyr Cys Gln Gln
                85                  90                  95 tat tat acc tat cct acg ttc ggt gga ggg acc aag                    324
Tyr Tyr Thr Tyr Pro Thr Phe Gly Gly Gly Thr Lys
            100                 105

<210> SEQ ID NO 64
<211> LENGTH: 108
<212> TYPE: PRT
<213> ORGANISM: Mus musculus

<400> SEQUENCE: 64
```

```
Asp Ile Val Met Ser Gln Ser Pro Ser Ser Leu Ala Val Ser Val Gly
1               5                   10                  15

Glu Lys Val Thr Met Ser Cys Lys Ser Ser Gln Arg Leu Leu Tyr Tyr
                20                  25                  30

Ser Thr Gln Lys Asn Tyr Leu Ala Trp Tyr Gln Gln Lys Pro Gly Gln
            35                  40                  45

Ser Pro Lys Leu Leu Ile Phe Trp Ala Ser Thr Arg Glu Ser Gly Val
        50                  55                  60

Pro Asn Arg Phe Thr Gly Ser Gly Ser Gly Thr Asp Phe Thr Leu Thr
65                  70                  75                  80

Ile Asn Ser Val Lys Ala Glu Asp Leu Ala Val Tyr Tyr Cys Gln Gln
                85                  90                  95

Tyr Tyr Thr Tyr Pro Thr Phe Gly Gly Gly Thr Lys
            100                 105
```

<210> SEQ ID NO 65
<211> LENGTH: 12
<212> TYPE: PRT
<213> ORGANISM: Mus musculus

<400> SEQUENCE: 65

```
Tyr Ser Ile Thr Ser Gly Tyr Asp Trp His Trp Ile
1               5                   10
```

<210> SEQ ID NO 66
<211> LENGTH: 16
<212> TYPE: PRT
<213> ORGANISM: Mus musculus

<400> SEQUENCE: 66

```
Tyr Ile Asn Tyr Ser Gly Ser Thr Asn Tyr Lys Pro Ser Leu Lys Ser
1               5                   10                  15
```

<210> SEQ ID NO 67
<211> LENGTH: 12
<212> TYPE: PRT
<213> ORGANISM: Mus musculus

<400> SEQUENCE: 67

```
Ala Arg Gly Ser Tyr Tyr Ser Tyr Glu Phe Ala Tyr
1               5                   10
```

<210> SEQ ID NO 68
<211> LENGTH: 17
<212> TYPE: PRT
<213> ORGANISM: Mus musculus

<400> SEQUENCE: 68

```
Lys Ser Ser Gln Arg Leu Leu Tyr Tyr Ser Thr Gln Lys Asn Tyr Leu
1               5                   10                  15
Ala
```

<210> SEQ ID NO 69
<211> LENGTH: 7
<212> TYPE: PRT
<213> ORGANISM: Mus musculus

<400> SEQUENCE: 69

```
Trp Ala Ser Thr Arg Glu Ser
1               5
```

```
<210> SEQ ID NO 70
<211> LENGTH: 8
<212> TYPE: PRT
<213> ORGANISM: Mus musculus

<400> SEQUENCE: 70

Gln Gln Tyr Tyr Thr Tyr Pro Thr
1               5

<210> SEQ ID NO 71
<211> LENGTH: 387
<212> TYPE: DNA
<213> ORGANISM: Mus musculus
<220> FEATURE:
<221> NAME/KEY: CDS
<222> LOCATION: (1)..(387)
<223> OTHER INFORMATION:

<400> SEQUENCE: 71 gag gtt cag ctg cag cag tct gga cct gac ctg gtg aag cct ggg acg        48
Glu Val Gln Leu Gln Gln Ser Gly Pro Asp Leu Val Lys Pro Gly Thr
1               5                   10                  15 tca gtt aag ata tcc tgc aag gcc tct ggg tac aaa ttt act gac ttc        96
Ser Val Lys Ile Ser Cys Lys Ala Ser Gly Tyr Lys Phe Thr Asp Phe
            20                  25                  30 aat atg gac tgg gtg agg cag aga cat gga aag agc ctt gag tgg att       144
Asn Met Asp Trp Val Arg Gln Arg His Gly Lys Ser Leu Glu Trp Ile
        35                  40                  45 gga gat gtg aat cct cag aat ggt gag att ttt tac aac cag aaa ttc       192
Gly Asp Val Asn Pro Gln Asn Gly Glu Ile Phe Tyr Asn Gln Lys Phe
    50                  55                  60 agg ggc aag gcc aca ttg act gtg gtc aag tct tcc agc aca acc tac       240
Arg Gly Lys Ala Thr Leu Thr Val Val Lys Ser Ser Ser Thr Thr Tyr
65                  70                  75                  80 ttg gaa ctc cgc agc ctg aca tct gag gac act gca gtc tat ttc tgt       288
Leu Glu Leu Arg Ser Leu Thr Ser Glu Asp Thr Ala Val Tyr Phe Cys
                85                  90                  95 aca aga tta gaa ttt gat tat acc ggc agt aac gga ttt gct tac tgg       336
Thr Arg Leu Glu Phe Asp Tyr Thr Gly Ser Asn Gly Phe Ala Tyr Trp
            100                 105                 110 ggc caa ggg act ctg gtc acg gtc tct gca gcc aaa acg aca ccc cca       384
Gly Gln Gly Thr Leu Val Thr Val Ser Ala Ala Lys Thr Thr Pro Pro
        115                 120                 125 tct                                                                    387
Ser

<210> SEQ ID NO 72
<211> LENGTH: 129
<212> TYPE: PRT
<213> ORGANISM: Mus musculus

<400> SEQUENCE: 72

Glu Val Gln Leu Gln Gln Ser Gly Pro Asp Leu Val Lys Pro Gly Thr
1               5                   10                  15

Ser Val Lys Ile Ser Cys Lys Ala Ser Gly Tyr Lys Phe Thr Asp Phe
            20                  25                  30

Asn Met Asp Trp Val Arg Gln Arg His Gly Lys Ser Leu Glu Trp Ile
        35                  40                  45

Gly Asp Val Asn Pro Gln Asn Gly Glu Ile Phe Tyr Asn Gln Lys Phe
    50                  55                  60

Arg Gly Lys Ala Thr Leu Thr Val Val Lys Ser Ser Ser Thr Thr Tyr
65                  70                  75                  80
```

```
Leu Glu Leu Arg Ser Leu Thr Ser Glu Asp Thr Ala Val Tyr Phe Cys
            85                  90                  95

Thr Arg Leu Glu Phe Asp Tyr Thr Gly Ser Asn Gly Phe Ala Tyr Trp
        100                 105                 110

Gly Gln Gly Thr Leu Val Thr Val Ser Ala Ala Lys Thr Thr Pro Pro
        115                 120                 125

Ser

<210> SEQ ID NO 73
<211> LENGTH: 324
<212> TYPE: DNA
<213> ORGANISM: Mus musculus
<220> FEATURE:
<221> NAME/KEY: CDS
<222> LOCATION: (1)..(324)
<223> OTHER INFORMATION:

<400> SEQUENCE: 73 gac att ttg atg acc caa act cca ctc tcc ctg cct gtc agt ctt gga      48
Asp Ile Leu Met Thr Gln Thr Pro Leu Ser Leu Pro Val Ser Leu Gly
1               5                   10                  15 gat caa gcc tcc atc tct tgc aga tct agt cag acc ctt gta cat cgc      96
Asp Gln Ala Ser Ile Ser Cys Arg Ser Ser Gln Thr Leu Val His Arg
            20                  25                  30 aat gga aac acc tat tta gag tgg tac ctt cag aag cca ggc cag tct     144
Asn Gly Asn Thr Tyr Leu Glu Trp Tyr Leu Gln Lys Pro Gly Gln Ser
        35                  40                  45 cca aaa ctc ctg atc tac aaa gtt tcc aac cga ttt tct ggg gtc cca     192
Pro Lys Leu Leu Ile Tyr Lys Val Ser Asn Arg Phe Ser Gly Val Pro
    50                  55                  60 gac agg ttc agt ggc cgt gga tca ggg aca gat ttc aca ctc aag atc     240
Asp Arg Phe Ser Gly Arg Gly Ser Gly Thr Asp Phe Thr Leu Lys Ile
65                  70                  75                  80 agc aga gtg gag gct gag gat cag gga att tat tac tgc ttt caa ggt     288
Ser Arg Val Glu Ala Glu Asp Gln Gly Ile Tyr Tyr Cys Phe Gln Gly
                85                  90                  95 tca cat gat ccg tgg acg ttc ggt gga ggg acc aag                     324
Ser His Asp Pro Trp Thr Phe Gly Gly Gly Thr Lys
            100                 105

<210> SEQ ID NO 74
<211> LENGTH: 108
<212> TYPE: PRT
<213> ORGANISM: Mus musculus

<400> SEQUENCE: 74

Asp Ile Leu Met Thr Gln Thr Pro Leu Ser Leu Pro Val Ser Leu Gly
1               5                   10                  15

Asp Gln Ala Ser Ile Ser Cys Arg Ser Ser Gln Thr Leu Val His Arg
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Arg Gly Ser Gly Thr Asp Phe Thr Leu Lys Ile
65                  70                  75                  80

Ser Arg Val Glu Ala Glu Asp Gln Gly Ile Tyr Tyr Cys Phe Gln Gly
                85                  90                  95

Ser His Asp Pro Trp Thr Phe Gly Gly Gly Thr Lys
```

-continued

<210> SEQ ID NO 75
<211> LENGTH: 9
<212> TYPE: PRT
<213> ORGANISM: Mus musculus

<400> SEQUENCE: 75

Tyr Lys Phe Thr Asp Phe Asn Met Asp
1               5

<210> SEQ ID NO 76
<211> LENGTH: 17
<212> TYPE: PRT
<213> ORGANISM: Mus musculus

<400> SEQUENCE: 76

Asp Val Asn Pro Gln Asn Gly Glu Ile Phe Tyr Asn Gln Lys Phe Arg
1               5                   10                  15

Gly

<210> SEQ ID NO 77
<211> LENGTH: 14
<212> TYPE: PRT
<213> ORGANISM: Mus musculus

<400> SEQUENCE: 77

Cys Thr Arg Leu Glu Phe Asp Tyr Thr Gly Ser Asn Gly Phe
1               5                   10

<210> SEQ ID NO 78
<211> LENGTH: 16
<212> TYPE: PRT
<213> ORGANISM: Mus musculus

<400> SEQUENCE: 78

Arg Ser Ser Gln Thr Leu Val His Arg Asn Gly Asn Thr Tyr Leu Glu
1               5                   10                  15

<210> SEQ ID NO 79
<211> LENGTH: 7
<212> TYPE: PRT
<213> ORGANISM: Mus musculus

<400> SEQUENCE: 79

Lys Val Ser Asn Arg Phe Ser
1               5

<210> SEQ ID NO 80
<211> LENGTH: 9
<212> TYPE: PRT
<213> ORGANISM: Mus musculus

<400> SEQUENCE: 80

Phe Gln Gly Ser His Asp Pro Trp Thr
1               5

<210> SEQ ID NO 81
<211> LENGTH: 1137
<212> TYPE: DNA
<213> ORGANISM: Homo sapiens
<220> FEATURE:
<221> NAME/KEY: CDS
<222> LOCATION: (1)..(1137)
<223> OTHER INFORMATION:

<400> SEQUENCE: 81

```
atg gac ctg ggg aaa cca atg aaa agc gtg ctg gtg gtg gct ctc ctt        48
Met Asp Leu Gly Lys Pro Met Lys Ser Val Leu Val Val Ala Leu Leu
1               5                   10                  15 gtc att ttc cag gta tgc ctg tgt caa gat gag gtc acg gac gat tac        96
Val Ile Phe Gln Val Cys Leu Cys Gln Asp Glu Val Thr Asp Asp Tyr
            20                  25                  30 atc gga gac aac acc aca gtg gac tac act ttg ttc gag tct ttg tgc       144
Ile Gly Asp Asn Thr Thr Val Asp Tyr Thr Leu Phe Glu Ser Leu Cys
        35                  40                  45 tcc aag aag gac gtg cgg aac ttt aaa gcc tgg ttc ctc cct atc atg       192
Ser Lys Lys Asp Val Arg Asn Phe Lys Ala Trp Phe Leu Pro Ile Met
50                  55                  60 tac tcc atc att tgt ttc gtg ggc cta ctg ggc aat ggg ctg gtc gtg       240
Tyr Ser Ile Ile Cys Phe Val Gly Leu Leu Gly Asn Gly Leu Val Val
65                  70                  75                  80 ttg acc tat atc tat ttc aag agg ctc aag acc atg acc gat acc tac       288
Leu Thr Tyr Ile Tyr Phe Lys Arg Leu Lys Thr Met Thr Asp Thr Tyr
                85                  90                  95 ctg ctc aac ctg gcg gtg gca gac atc ctc ttc ctg acc ctt ccc           336
Leu Leu Asn Leu Ala Val Ala Asp Ile Leu Phe Leu Leu Thr Leu Pro
            100                 105                 110 ttc tgg gcc tac agc gcg gcc aag tcc tgg gtc ttc ggt gtc cac ttt       384
Phe Trp Ala Tyr Ser Ala Ala Lys Ser Trp Val Phe Gly Val His Phe
        115                 120                 125 tgc aag ctc atc ttt gcc atc tac aag atg agc ttc ttc agt ggc atg       432
Cys Lys Leu Ile Phe Ala Ile Tyr Lys Met Ser Phe Phe Ser Gly Met
130                 135                 140 ctc cta ctt ctt tgc atc agc att gac cgc tac gtg gcc atc gtc cag       480
Leu Leu Leu Leu Cys Ile Ser Ile Asp Arg Tyr Val Ala Ile Val Gln
145                 150                 155                 160 gct gtc tca gct cac cgc cac cgt gcc cgc gtc ctt ctc atc agc aag       528
Ala Val Ser Ala His Arg His Arg Ala Arg Val Leu Leu Ile Ser Lys
                165                 170                 175 ctg tcc tgt gtg ggc atc tgg ata cta gcc aca gtg ctc tcc atc cca       576
Leu Ser Cys Val Gly Ile Trp Ile Leu Ala Thr Val Leu Ser Ile Pro
            180                 185                 190 gag ctc ctg tac agt gac ctc cag agg agc agc agt gag caa gcg atg       624
Glu Leu Leu Tyr Ser Asp Leu Gln Arg Ser Ser Ser Glu Gln Ala Met
        195                 200                 205 cga tgc tct ctc atc aca gag cat gtg gag gcc ttt atc acc atc cag       672
Arg Cys Ser Leu Ile Thr Glu His Val Glu Ala Phe Ile Thr Ile Gln
210                 215                 220 gtg gcc cag atg gtg atc ggc ttt ctg gtc ccc ctg ctg gcc atg agc       720
Val Ala Gln Met Val Ile Gly Phe Leu Val Pro Leu Leu Ala Met Ser
225                 230                 235                 240 ttc tgt tac ctt gtc atc atc cgc acc ctg ctc cag gca cgc aac ttt       768
Phe Cys Tyr Leu Val Ile Ile Arg Thr Leu Leu Gln Ala Arg Asn Phe
                245                 250                 255 gag cgc aac aag gcc atc aag gtg atc atc gct gtg gtc gtg gtc ttc       816
Glu Arg Asn Lys Ala Ile Lys Val Ile Ile Ala Val Val Val Val Phe
            260                 265                 270 ata gtc ttc cag ctg ccc tac aat ggg gtg gtc ctg gcc cag acg gtg       864
Ile Val Phe Gln Leu Pro Tyr Asn Gly Val Val Leu Ala Gln Thr Val
        275                 280                 285 gcc aac ttc aac atc acc agt agc acc tgt gag ctc agt aag caa ctc       912
Ala Asn Phe Asn Ile Thr Ser Ser Thr Cys Glu Leu Ser Lys Gln Leu
290                 295                 300
```

```
aac atc gcc tac gac gtc acc tac agc ctg gcc tgc gtc cgc tgc tgc      960
Asn Ile Ala Tyr Asp Val Thr Tyr Ser Leu Ala Cys Val Arg Cys Cys
305                 310                 315                 320 gtc aac cct ttc ttg tac gcc ttc atc ggc gtc aag ttc cgc aac gat     1008
Val Asn Pro Phe Leu Tyr Ala Phe Ile Gly Val Lys Phe Arg Asn Asp
                325                 330                 335 ctc ttc aag ctc ttc aag gac ctg ggc tgc ctc agc cag gag cag ctc     1056
Leu Phe Lys Leu Phe Lys Asp Leu Gly Cys Leu Ser Gln Glu Gln Leu
            340                 345                 350 cgg cag tgg tct tcc tgt cgg cac atc cgg cgc tcc tcc atg agt gtg     1104
Arg Gln Trp Ser Ser Cys Arg His Ile Arg Arg Ser Ser Met Ser Val
        355                 360                 365 gag gcc gag acc acc acc acc ttc tcc cca tag                          1137
Glu Ala Glu Thr Thr Thr Thr Phe Ser Pro
370                 375
```

<210> SEQ ID NO 82
<211> LENGTH: 378
<212> TYPE: PRT
<213> ORGANISM: Homo sapiens

<400> SEQUENCE: 82

```
Met Asp Leu Gly Lys Pro Met Lys Ser Val Leu Val Val Ala Leu Leu
1               5                   10                  15

Val Ile Phe Gln Val Cys Leu Cys Gln Asp Glu Val Thr Asp Asp Tyr
            20                  25                  30

Ile Gly Asp Asn Thr Thr Val Asp Tyr Thr Leu Phe Glu Ser Leu Cys
        35                  40                  45

Ser Lys Lys Asp Val Arg Asn Phe Lys Ala Trp Phe Leu Pro Ile Met
    50                  55                  60

Tyr Ser Ile Ile Cys Phe Val Gly Leu Leu Gly Asn Gly Leu Val Val
65                  70                  75                  80

Leu Thr Tyr Ile Tyr Phe Lys Arg Leu Lys Thr Met Thr Asp Thr Tyr
                85                  90                  95

Leu Leu Asn Leu Ala Val Ala Asp Ile Leu Phe Leu Leu Thr Leu Pro
            100                 105                 110

Phe Trp Ala Tyr Ser Ala Ala Lys Ser Trp Val Phe Gly Val His Phe
        115                 120                 125

Cys Lys Leu Ile Phe Ala Ile Tyr Lys Met Ser Phe Phe Ser Gly Met
    130                 135                 140

Leu Leu Leu Leu Cys Ile Ser Ile Asp Arg Tyr Val Ala Ile Val Gln
145                 150                 155                 160

Ala Val Ser Ala His Arg His Arg Ala Arg Val Leu Leu Ile Ser Lys
                165                 170                 175

Leu Ser Cys Val Gly Ile Trp Ile Leu Ala Thr Val Leu Ser Ile Pro
            180                 185                 190

Glu Leu Leu Tyr Ser Asp Leu Gln Arg Ser Ser Glu Gln Ala Met
        195                 200                 205

Arg Cys Ser Leu Ile Thr Glu His Val Glu Ala Phe Ile Thr Ile Gln
    210                 215                 220

Val Ala Gln Met Val Ile Gly Phe Leu Val Pro Leu Leu Ala Met Ser
225                 230                 235                 240

Phe Cys Tyr Leu Val Ile Ile Arg Thr Leu Leu Gln Ala Arg Asn Phe
                245                 250                 255

Glu Arg Asn Lys Ala Ile Lys Val Ile Ile Ala Val Val Val Val Phe
            260                 265                 270
```

```
Ile Val Phe Gln Leu Pro Tyr Asn Gly Val Val Leu Ala Gln Thr Val
        275                 280                 285

Ala Asn Phe Asn Ile Thr Ser Ser Thr Cys Glu Leu Ser Lys Gln Leu
    290                 295                 300

Asn Ile Ala Tyr Asp Val Thr Tyr Ser Leu Ala Cys Val Arg Cys Cys
305                 310                 315                 320

Val Asn Pro Phe Leu Tyr Ala Phe Ile Gly Val Lys Phe Arg Asn Asp
                325                 330                 335

Leu Phe Lys Leu Phe Lys Asp Leu Gly Cys Leu Ser Gln Glu Gln Leu
            340                 345                 350

Arg Gln Trp Ser Ser Cys Arg His Ile Arg Arg Ser Ser Met Ser Val
        355                 360                 365

Glu Ala Glu Thr Thr Thr Thr Phe Ser Pro
    370                 375

<210> SEQ ID NO 83
<211> LENGTH: 15
<212> TYPE: DNA
<213> ORGANISM: Artificial
<220> FEATURE:
<223> OTHER INFORMATION: Linker

<400> SEQUENCE: 83
gtcgactagg aattc                                                    15

<210> SEQ ID NO 84
<211> LENGTH: 33
<212> TYPE: DNA
<213> ORGANISM: Artificial
<220> FEATURE:
<223> OTHER INFORMATION: Designed oligonucleotide primer for PCR

<400> SEQUENCE: 84
tggcgtcgac atggcagcta aagacgtaaa att                                33

<210> SEQ ID NO 85
<211> LENGTH: 37
<212> TYPE: DNA
<213> ORGANISM: Artificial
<220> FEATURE:
<223> OTHER INFORMATION: Designed oligonucleotide primer for PCR

<400> SEQUENCE: 85
tggcgcggcc gcctattaca tcatgccgcc catgcca                            37

<210> SEQ ID NO 86
<211> LENGTH: 1647
<212> TYPE: DNA
<213> ORGANISM: Escherichia coli

<400> SEQUENCE: 86
atggcagcta aagacgtaaa attcggtaac gacgctcgtg tgaaaatgct gcgcggcgta    60
aacgtactgg cagatgcagt gaaagttacc ctcggtccaa aaggccgtaa cgtagttctg   120
gataaatctt cggtgcacc gaccatcacc aaagatggtg tttccgttgc tcgtgaaatc   180
gaactggaag acaagttcga aaatatgggt gcgcagatgg tgaaagaagt tgcctctaaa   240
gcaaacgacg ctgcaggcga cggtaccacc actgcaaccg tactggctca ggctatcatc   300
actgaaggtc tgaaagctgt tgctgcgggc atgaacccga tggacctgaa acgtggtatc   360
gacaaagcgg ttaccgctgc agttgaagaa ctgaaagcgc tgtccgtacc atgctctgac   420
```

```
tctaaagcga ttgctcaggt tggtaccatc tccgctaact ccgacgaaac cgtaggtaaa      480
ctgatcgctg aagcgatgga caaagtcggt aaagaaggcg ttatcaccgt tgaagacggt      540
accggtctgc aggacgaact ggacgtggtt gaaggtatgc agttcgaccg tggctacctg      600
tctccttact tcatcaacaa gccggaaact ggcgcagtag aactggaaag cccgttcatc      660
ctgctggctg acaagaaaat ctccaacatc cgcgaaatgc tgccggttct ggaagctgtt      720
gccaaagcag gcaaaccgct gctgatcatc gctgaagatg tagaaggcga agcgctggca      780
actctggttg ttaacaccat gcgtggcatc gtgaaagtcg ctgcggttaa agcaccgggc      840
ttcggcgatc gtcgtaaagc tatgctgcag gatatcgcaa ccctgactgg cggtaccgtg      900
atctctgaag agatcggtat ggagctggaa aaagcaaccc tggaagacct gggtcaggct      960
aaacgtgttg tgatcaacaa agacaccacc actatcatcg atggcgtggg tgaagaagct     1020
gcaatccagg gccgtgttgc tcagatccgt cagcagattg aagaagcaac ttctgactac     1080
gaccgtgaaa aactgcagga acgcgtagcg aaactggcag cggcgttgc agttatcaaa      1140 gtgggtgctg ctaccgaagt tgaaatgaaa gagaaaaaag cacgcgttga agatgccctg     1200
cacgcgaccc gtgctgcggt agaagaaggc gtggttgctg gtggtggtgt tgcgctgatc     1260
cgcgtagcgt ctaaactggc tgacctgcgt ggtcagaacg aagaccagaa cgtgggtatc     1320
aaagttgcac tgcgtgcaat ggaagctccg ctgcgtcaga tcgtattgaa ctgcggcgaa     1380
gaaccgtctg ttgttgctaa caccgttaaa ggcggcgacg gcaactacgg ttacaacgca     1440
gcaaccgaag aatacggcaa catgatcgac atgggtatcc tggatccaac caaagtaact     1500
cgttctgctc tgcagtacgc agcttctgtg gctggcctga tgatcaccac cgaatgcatg     1560
gttaccgacc tgccgaaaaa cgatgcagct gacttaggcg ctgctggcgg tatgggcggc     1620
atgggtggca tgggcggcat gatgtaa                                          1647
```

<210> SEQ ID NO 87
<211> LENGTH: 22
<212> TYPE: DNA
<213> ORGANISM: Artificial
<220> FEATURE:
<223> OTHER INFORMATION: Designed oligonucleotide primer for PCR

<400> SEQUENCE: 87
cagatggggs tgtygttttg gc                                                22

<210> SEQ ID NO 88
<211> LENGTH: 21
<212> TYPE: DNA
<213> ORGANISM: Artificial
<220> FEATURE:
<223> OTHER INFORMATION: Designed oligonucleotide primer for PCR

<400> SEQUENCE: 88
tttkatttcc agyttggtcc c                                                 21

<210> SEQ ID NO 89
<211> LENGTH: 21
<212> TYPE: DNA
<213> ORGANISM: Artificial
<220> FEATURE:
<223> OTHER INFORMATION: Designed oligonucleotide primer for PCR

<400> SEQUENCE: 89
ttttatttcc aactttgtcc c                                                 21

```
<210> SEQ ID NO 90
<211> LENGTH: 21
<212> TYPE: DNA
<213> ORGANISM: Artificial
<220> FEATURE:
<223> OTHER INFORMATION: Designed oligonucleotide primer for PCR

<400> SEQUENCE: 90
tttcagctcc agcttggtcc c                                              21

<210> SEQ ID NO 91
<211> LENGTH: 19
<212> TYPE: DNA
<213> ORGANISM: Artificial
<220> FEATURE:
<223> OTHER INFORMATION: Designed oligonucleotide primer for PCR

<400> SEQUENCE: 91
cctaggacag tcagtttgg                                                 19
```